(12) United States Patent
Sandberg et al.

(10) Patent No.: US 11,158,062 B2
(45) Date of Patent: Oct. 26, 2021

(54) AUTOMATED IMPLANT MOVEMENT ANALYSIS SYSTEMS AND RELATED METHODS

(71) Applicant: Sectra AB, Linköping (SE)

(72) Inventors: Olof Sandberg, Linköping (SE); Claes Lundström, Linköping (SE)

(73) Assignee: Sectra AB, Linköping (SE)

( * ) Notice: Subject to any disclaimer, the term of this patent is extended or adjusted under 35 U.S.C. 154(b) by 131 days.

(21) Appl. No.: 16/752,799

(22) Filed: Jan. 27, 2020

(65) Prior Publication Data
US 2020/0258220 A1     Aug. 13, 2020

Related U.S. Application Data

(60) Provisional application No. 62/805,056, filed on Feb. 13, 2019, provisional application No. 62/824,598, filed on Mar. 27, 2019.

(51) Int. Cl.
*G06K 9/00* (2006.01)
*G06T 7/215* (2017.01)
(Continued)

(52) U.S. Cl.
CPC .............. *G06T 7/215* (2017.01); *A61B 34/10* (2016.02); *G06K 9/6201* (2013.01);
(Continued)

(58) Field of Classification Search
CPC ................................................ G06K 2209/05
See application file for complete search history.

(56) References Cited

U.S. PATENT DOCUMENTS 8,126,234 B1\* 2/2012 Edwards ................. G06T 19/20
382/128
2013/0211531 A1\* 8/2013 Steines ................. A61F 2/3859
623/20.35
(Continued)

FOREIGN PATENT DOCUMENTS

WO      2020123928 A1    6/2020

OTHER PUBLICATIONS

Penney et al. "Postoperative Calculation of Acetabular Cup Position Using 2-D-3-D Registration" IEEE Transactions on Biomedical Engineering, 54(7):1342-1348 (2007).
(Continued)

*Primary Examiner* — Hadi Akhavannik
(74) *Attorney, Agent, or Firm* — Myers Bigel, P.A.

(57) ABSTRACT

Methods, systems, workstations, and computer program products that provide automated implant analysis of batches of image data sets of a plurality of different patients having an implant coupled to bone using a first data set of a first patient from the batch of image data sets, the first data set comprising a first image stack and a second image stack and allowing a user to select parameter settings for implant movement analysis of the implant including selecting a first object of interest and a second reference object. Measurements of movement of the implant and/or coupled bone can be automatically calculated and selected parameter settings can be automatically propagated to other image data sets of other patients of the batch of image data sets and measurements for the batch of image data sets of others of the different patients can be automatically calculated.

23 Claims, 46 Drawing Sheets
(24 of 46 Drawing Sheet(s) Filed in Color)

(51) Int. Cl.
*G16H 30/20* (2018.01)
*G16H 20/40* (2018.01)
*G06T 7/00* (2017.01)
*G06T 7/11* (2017.01)
*G06T 7/30* (2017.01)
*G06K 9/62* (2006.01)
*G06T 7/174* (2017.01)
*A61B 34/10* (2016.01)
*G06T 7/38* (2017.01)

(52) U.S. Cl.
CPC .......... *G06T 7/0012* (2013.01); *G06T 7/0014* (2013.01); *G06T 7/11* (2017.01); *G06T 7/174* (2017.01); *G06T 7/30* (2017.01); *G06T 7/38* (2017.01); *G16H 20/40* (2018.01); *G16H 30/20* (2018.01); *A61B 2034/102* (2016.02); *G06T 2207/10028* (2013.01); *G06T 2207/10081* (2013.01); *G06T 2207/30008* (2013.01); *G06T 2207/30052* (2013.01)

(56) References Cited

U.S. PATENT DOCUMENTS

| | | | | |
|---|---|---|---|---|
| 2014/0228860 | A1* | 8/2014 | Steines | A61B 34/30 606/130 |
| 2014/0270459 | A1* | 9/2014 | Moll | G01N 21/6428 382/134 |
| 2015/0023575 | A1* | 1/2015 | Valadez | G06T 7/11 382/131 |
| 2015/0265291 | A1* | 9/2015 | Wilkinson | A61B 17/175 606/89 |
| 2016/0045317 | A1* | 2/2016 | Lang | G05B 19/4099 700/98 |
| 2016/0100909 | A1* | 4/2016 | Wollowick | G06T 7/33 600/424 |
| 2016/0157751 | A1* | 6/2016 | Mahfouz | A61B 5/062 600/409 |
| 2016/0275703 | A1* | 9/2016 | Mariampillai | A61B 5/055 |
| 2016/0302870 | A1* | 10/2016 | Wilkinson | A61B 17/157 |
| 2017/0076442 | A1* | 3/2017 | Schoenmeyer | G16H 30/40 |
| 2018/0098137 | A1* | 4/2018 | Saha | G06K 9/0063 |
| 2018/0132946 | A1* | 5/2018 | Kao | G06T 7/337 |
| 2018/0180693 | A1* | 6/2018 | Boernert | G01R 33/56 |
| 2019/0000631 | A1* | 1/2019 | Blankevoort | A61B 6/12 |

OTHER PUBLICATIONS

Dodin et al. "A fully automated human knee 3D MRI bone segmentation using the ray casting technique" Medical & Biological Engineering & Computing, 49(12):1413-1424 (2011).

Jain et al. "Information Retrieval using Cosine and Jaccard Similarity Measures in Vector Space Model" International Journal of Computer Applications, 164(6):28-30 (2017).

Kronman et al. "Anatomical structures segmentation by spherical 3D ray casting and gradient domain editing" Medical Image Computing and Computer-Assisted Intervention, 15(Pt. 2):363-370 (2012).

Litjens et al. "A Survey on Deep Learning in Medical Image Analysis" Medical Image Analysis, 42:60-88 (2017).

Olivecrona et al. "Acetabular Component Migration in Total Hip Arthroplastry Using CT and a Semiautomated Program for Volume Merging" Acta Radiologica, 43:517-527 (2002).

Olivecrona et al. "A CT method for following patients with both prosthetic replacement and implanted tantalum beads: preliminary analysis with a pelvic model and in seven patients" Journal of Orthopaedic Surgery and Research, 11(27):1-12 (2016).

Olivecrona et al. "A new technique for diagnosis of acetabular cup loosening using computed tomography Preliminary experience in 10 patients" Acta Orthopaedica, 79(3):346-353 (2008).

Olivecrona et al. "Assessing Wear of the Acetabular Cup Using Computed Tomography: an ex vivo Study" Acta Radiologica, 8:852-857 (2005).

Olivecrona et al. "Stability of Acetabular Axis After Total Hip Arthroplasty, Repeatability Using CT and a Semiautomated Program for Volume Fusion" Acta Radiologica, 44:653-661 (2003).

Sandgren et al. "Computed tomography vs. digital radiography assessment for detection of osteolysis in asymptomatic patients with uncemented cups: a proposal for a new classification system based on computer tomography" The Journal of Arthroplasty, 28(9):1608-1613 (2013).

Svedmark et al. "Motion analysis of total cervical disc replacements using computed tomography: Preliminary experience with nine patients and a model" Acta Radiologica, 52:1128-1137 (2011).

Wang et al. "CT scan range estimation using multiple body parts detection: let PACS learn the CT image content" International Journal of Computer Assisted Radiology and Surgery, 11(2):317-325 (2016).

Wong et al. "On Modeling of Information Retrieval Concepts in Vector Spaces" ACM Transactions on Database Systems, 12(2):299-321 (1987).

* cited by examiner

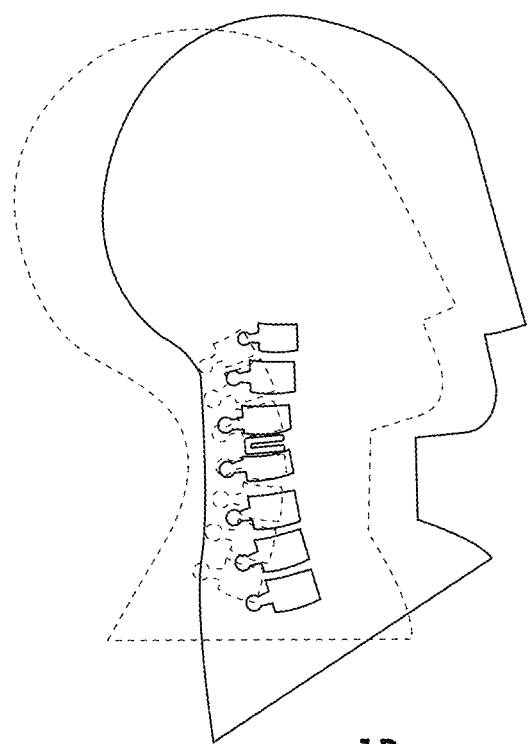
FIG. 1D
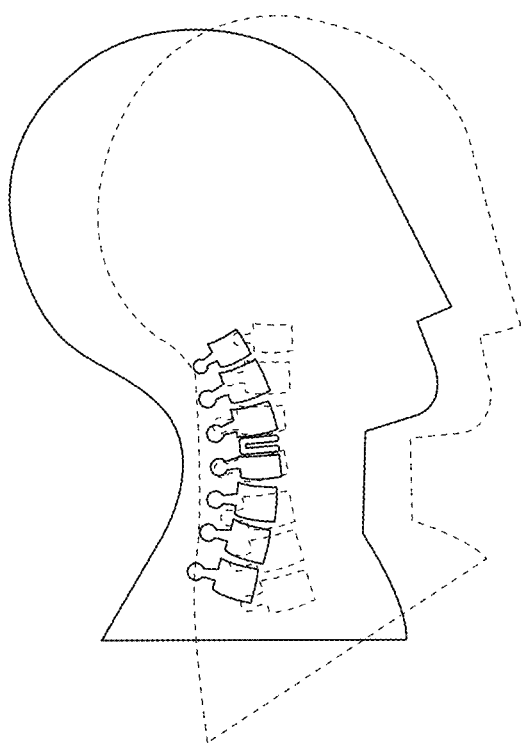
FIG. 1E

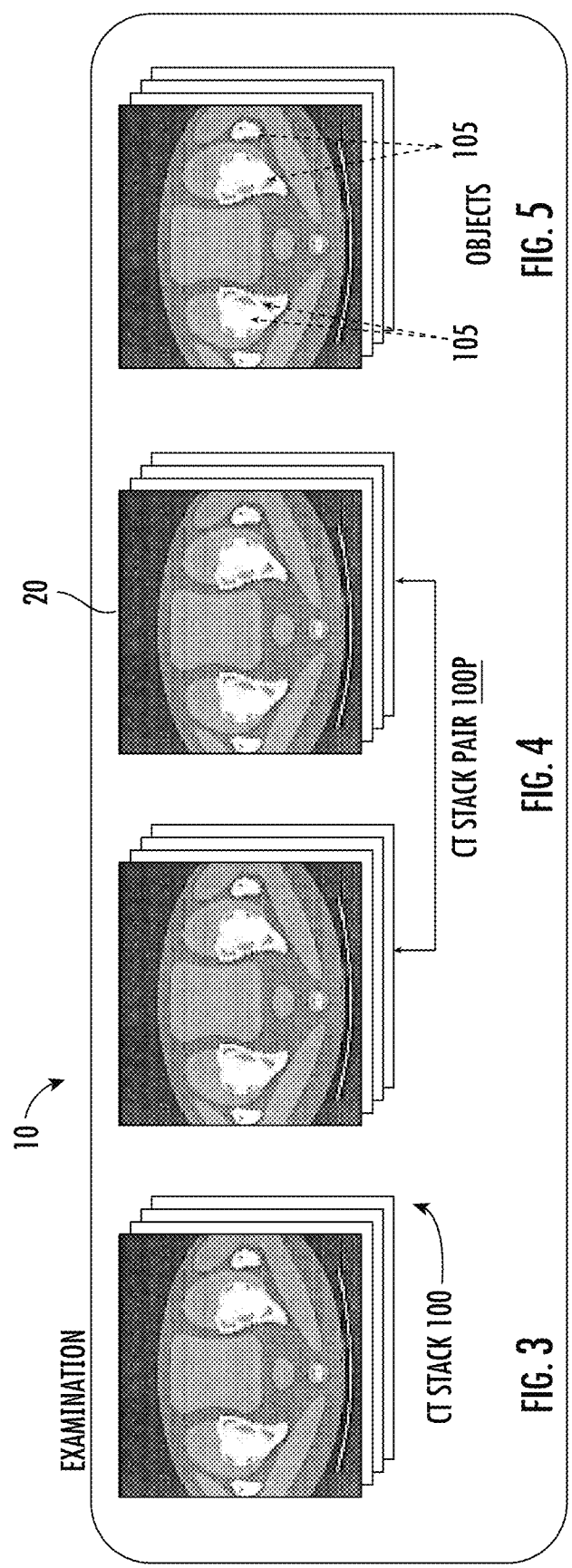
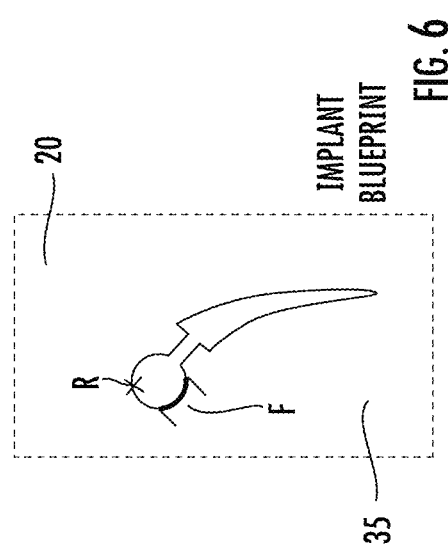

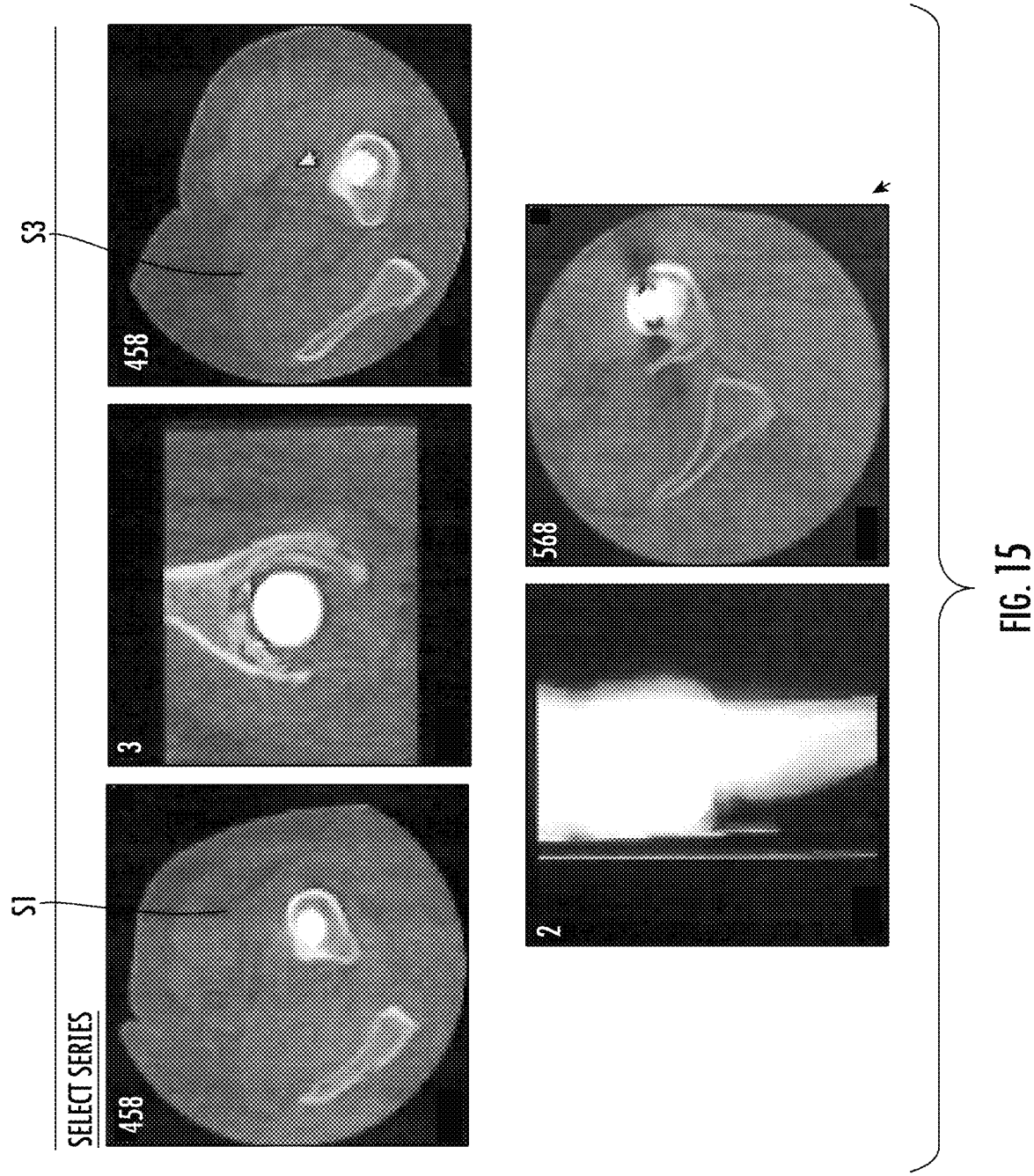

A REFERENCE POINT Rp (ILLUSTRATED BY CROSS) HAS BEEN ADDED TO AN IMPLANT BLUEPRINT

AN IMPLANT OF SAME MODEL AS BLUEPRINT HAS BEEN SEGMENTED IN A CT STACK

THE BLUEPRINT AND SEGMENTATION ARE REGISTERED

THANKS TO THE REGISTRATION, THE BLUEPRINT REFERENCE POINT IS CONNECTED TO A SPECIFIC POINT ON THE SEGMENTED IMPLANT

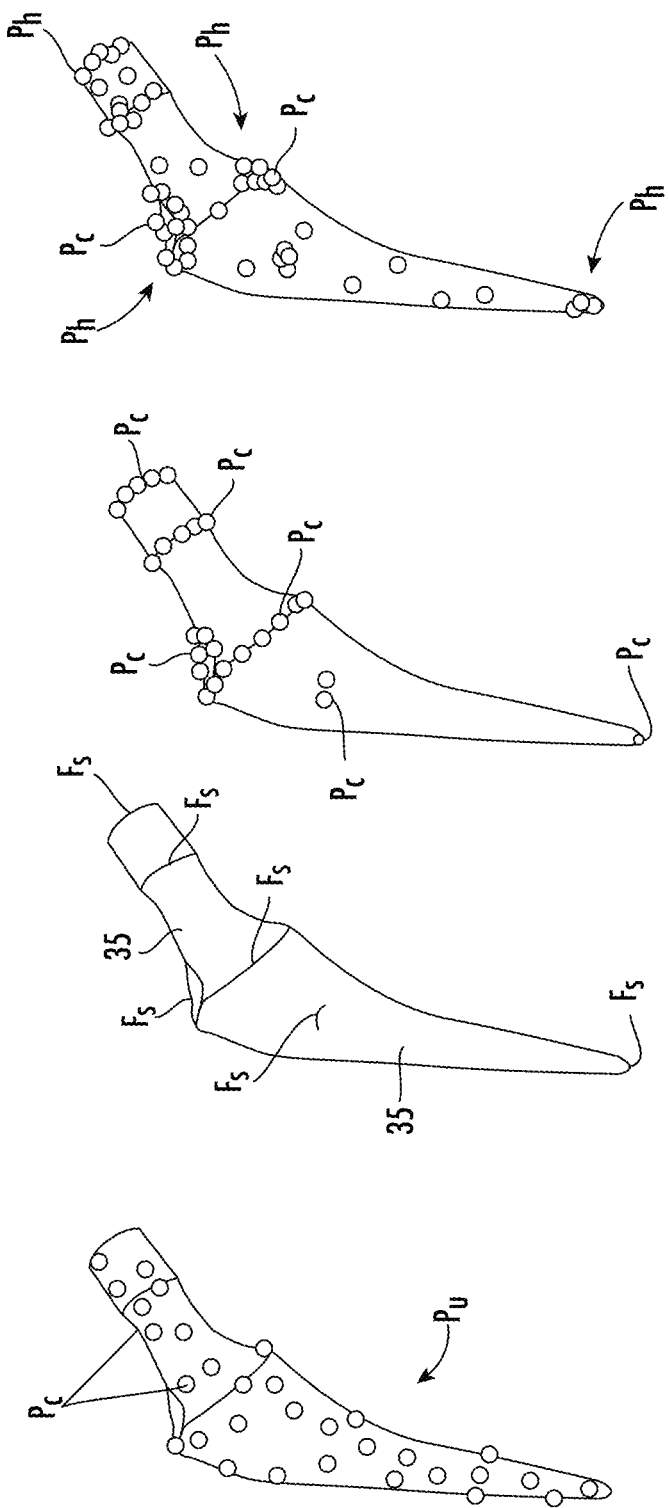

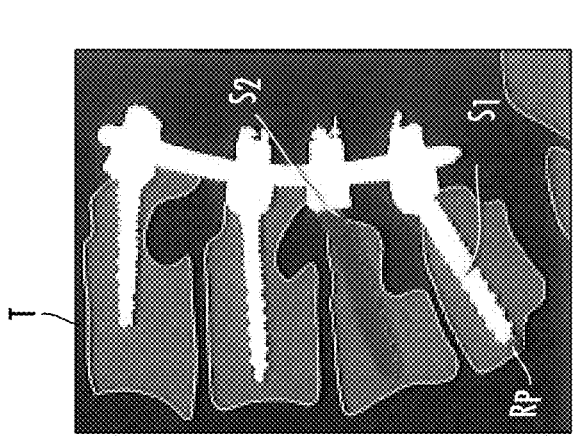

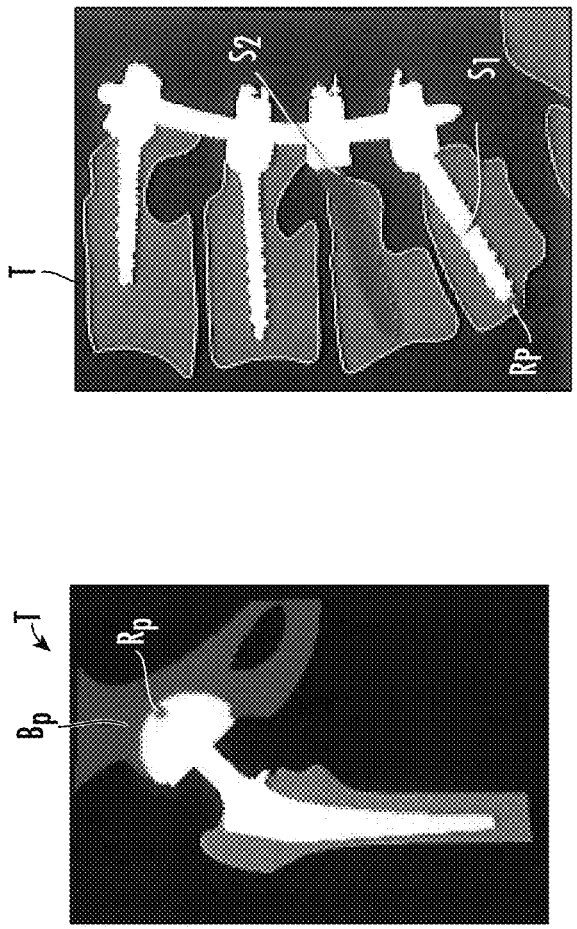

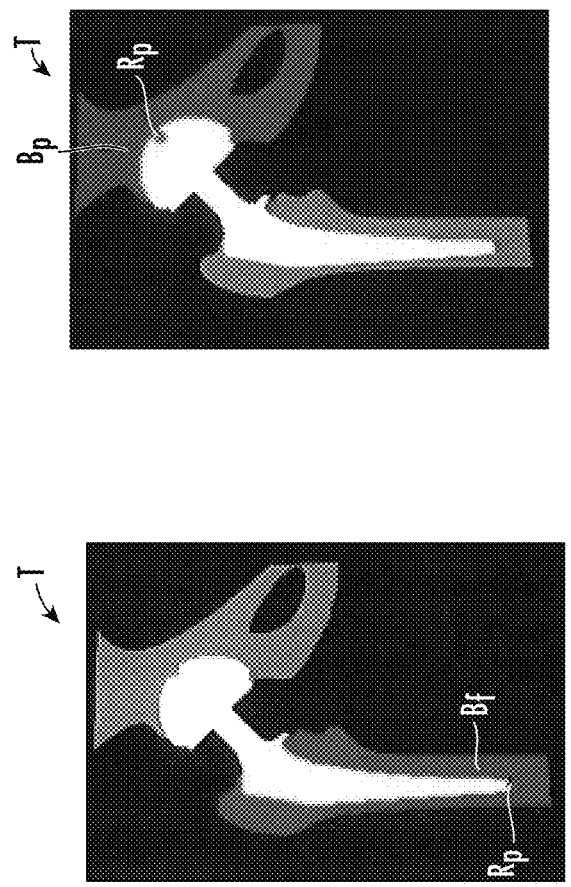

FIG. 30A

MEASUREMENT TARGET FOR HIP IMPLANT MOVEMENT, WHERE THE POINT TO MEASURE IS THE TIP OF THE IMPLANT STEM (RED) AND MOVEMENT IS RELATIVE TO THE REFERENCE OF THE FEMUR (GREEN)

FIG. 30B

MEASUREMENT TARGET FOR HIP IMPLANT MOVEMENT, WHERE THE POINT OF MEASURE IS AT THE TOP OF THE CUP OF THE IMPLANT (RED) AND MOVEMENT IS RELATIVE TO THE REFERENCE OF THE PELVIC BONE (GREEN)

FIG. 30C

MEASUREMENT TARGET FOR SPINE IMPLANT MOVEMENT, WHERE THE POINT OF MEASURE IS AT THE TIP OF THE LOWEST SCREW (RED) AND MOVEMENT IS RELATIVE TO THE REFERENCE OF THE SECOND LOWEST SCREW (GREEN)

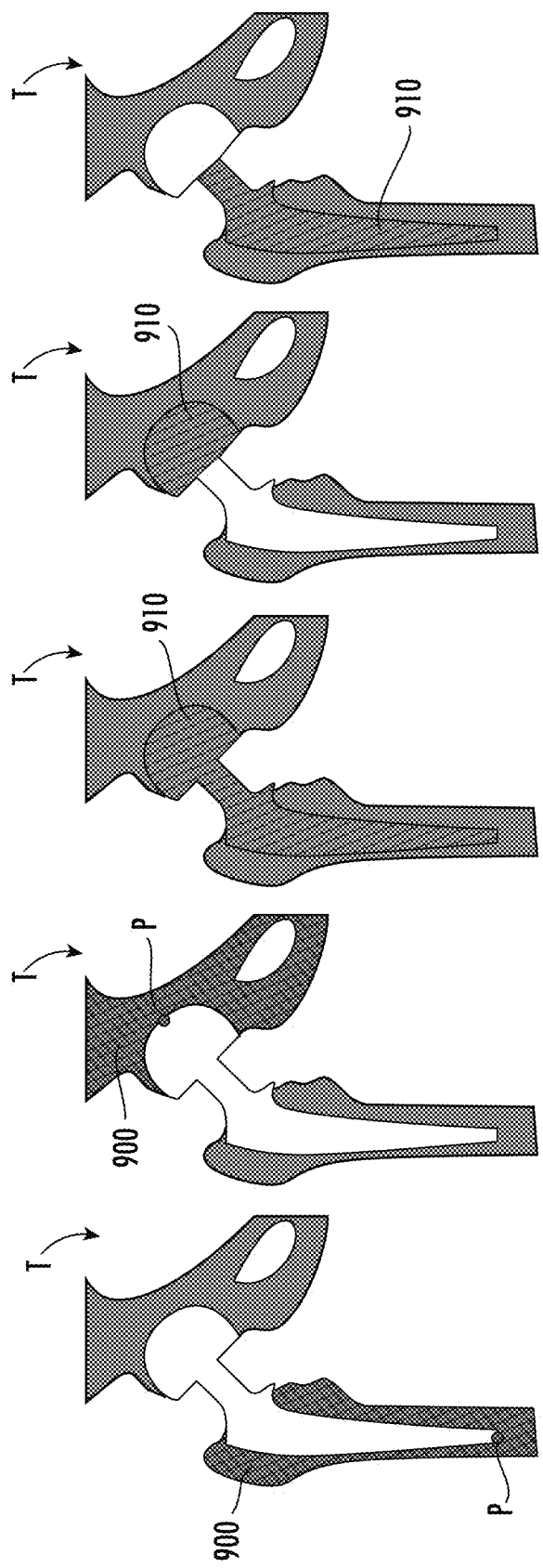

OBJECT WITH LOW RISK OF REGISTRATION ERROR DUE TO ASYMMETRY IN ALL DIMENSIONS

10

[10,10,10]

OBJECT WITH HIGH RISK OF ROTATIONAL REGISTRATION ERROR AROUND VERTICAL AXIS, BUT LOW RISK AROUND OTHER AXES

5

[1,9,9]

OBJECT WITH HIGH RISK OF ROTATIONAL REGISTRATION ERROR DUE TO SYMMETRY IN ALL DIMENSIONS

0

[0,0,0]

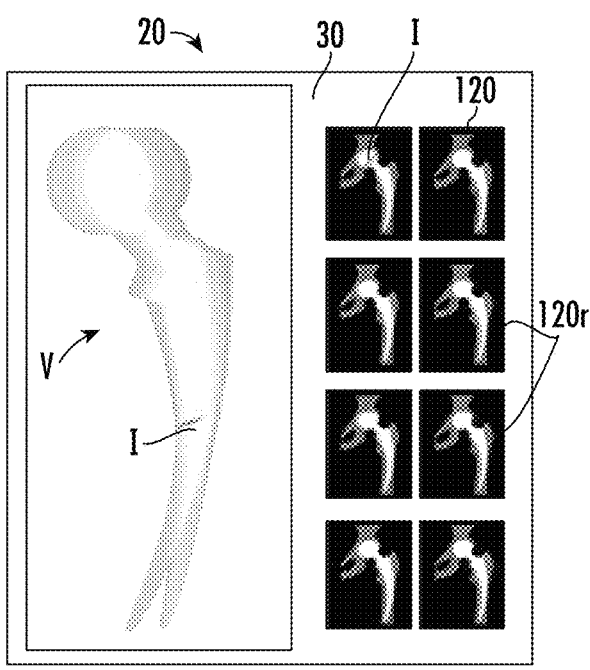

AGGREGATED VIEW TO THE LEFT, A THUMBNAIL IMAGE FOR EACH STACK TO THE RIGHT (WHERE EACH ROW IS A SEPARATE PATIENT)

FIG. 33A

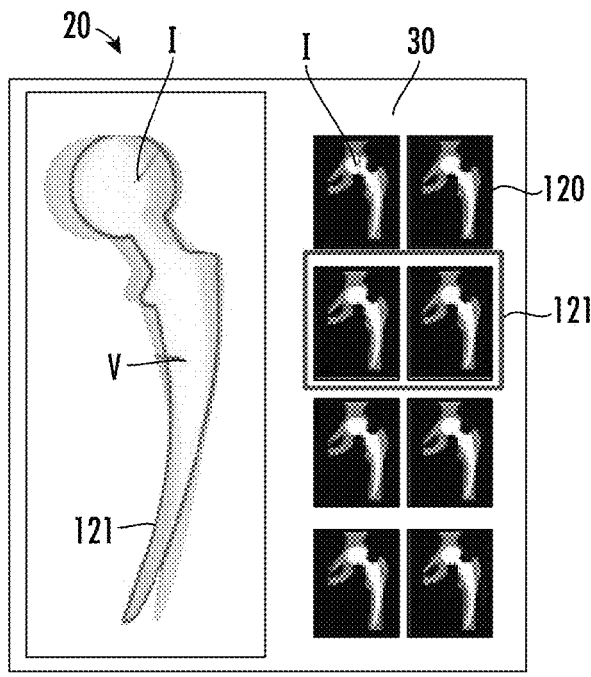

A SPECIFIC PATIENT HAS BEEN SELECTED, SHOWN IN RED BOTH IN AGGREGATED VIEW AND THUMBNAIL LIST. SELECTION CAN BE MADE IN BOTH AGGREGATED AND THUMBNAIL VIEWS

FIG. 33B

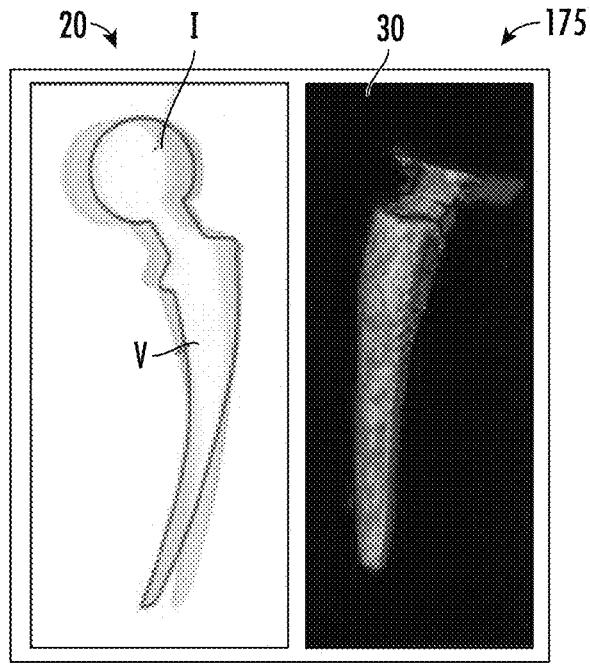

OTHER VIEWS CAN BE BROUGHT UP FOR THE SELECTED PATIENT, FOR INSTANCE THIS TO HIGHLIGHT REGISTRATION QUALITY

FIG. 33C

IMAGE WITH
SEGMENTED HIP IMPLANT

SEED POINTS (BLUE) FOR FEMUR
SEGMENTATION, AS DEFINED BY THEIR
SPATIAL RELATION TO THE IMPLANT

SEED POINTS ARE RETAINED (GREEN)
OR DISCARDED (RED) BASED ON THEIR
HOUNSFIELD VALUE

THE RESULTING SEGMENTATION
BASED ON THE RETAINED SEED POINTS

COORDINATE SYSTEM FOR MOVEMENT ANALYSIS DEFINED WITH IMPLANT AS REFERENCE

COORDINATE SYSTEM FOR MOVEMENT ANALYSIS DEFINED WITH PATIENT ANATOMY AS REFERENCE

EXAMPLE MEASUREMENT REFERENCE POINTS DEFINED AT FRONT (A), TOP (B), AND BACK (C) OF IMPLANT

AUTOMATED IMPLANT MOVEMENT ANALYSIS SYSTEMS AND RELATED METHODS

RELATED APPLICATIONS

This application claims the benefit of and priority to U.S. Provisional Application Ser. No. 62/805,056, filed Feb. 13, 2019 and U.S. Provisional Application Ser. No. 62/824,598, filed Mar. 27, 2019, the contents of which are hereby incorporated by reference as if recited in full herein.

FIELD OF THE INVENTION

The present invention is related to analysis of implanted medical devices.

BACKGROUND

Patients with pain or reduced function in their musculo-skeletal system (bone/tendon/musculature) can sometimes be treated with artificial implants, for instance joint replacement implants. These may or may not be successfully anchored in the surrounding bone. If they are not successfully anchored, they will eventually have to be replaced. The earlier this is performed the better since the surrounding bone can be destroyed (osteolysis) when adjacent to a loose implant. On the other hand, if there is no loosening, the replacement surgery (in medical terms: revision surgery) should be avoided since there is a patient safety risk from complications such as infections, and also because it would incur a substantial unnecessary cost.

However, to find out whether an implant is loose or unanchored or migrating has conventionally been difficult or, at least, error-prone, since only far-progressed loosening has been possible to reliably detect non-invasively. Thus, a surgeon makes the important decision as whether to perform implant revision or not based on unclear information.

A new diagnostic process which aids greatly in solving this diagnostic problem has been developed, by Sectra called Implant Movement Analysis (IMA). In IMA, two so-called provocation CT (Computed Tomography) scans can be taken of the patient; in one CT the joint under investigation is bent (provoked) in one direction, in the other CT the joint is bent in another direction (FIGS. 1A, 1B). The resulting CT images are then processed in software performing a rigid registration and overlaying the two CT images (FIG. 1C) so that the implant is held still on the screen while the doctor flicks back and forward (FIGS. 1D, 1E) between the two provocation CT images. Any small movement (typically down to at least 0.5 mm or 0.5 degrees) between implant and bone will be visible when switching between the two images, providing the requested early loosening detection.

The IMA method can also be used for other movement, migration or wear analyses. One example is movement between different parts of one or more implant, where movement could indicate an implant breakage/malfunction. Another example is longitudinal analysis of migration/wear, applied to two CT scans from different points in time (such as directly after surgery and months/years later) (FIGS. 2A-2C) instead of the provocation procedure typically of images taken at one time point, described above. A registration of the implant and migration-relevant bone can be generated with contours from different time points (FIG. 2D). Apart from the qualitative visual assessment described above, quantitative measures on the movements can be derived and presented as measures of migration over time in terms of translation and rotation (FIG. 2E).

Another implant movement analysis method developed and sold by Sectra is called CT implant Micromotion Analysis (CTMA). CTMA is a quantitative analysis of change in location and rotation of an object between two CT stacks. The change is reported relative to a secondary object, referred to as the reference object. Thus, one comparison involves at least two objects each represented in at least two CT stacks. The typical scenario for CTMA is to compare several time points, to see whether an implant is migrating in the body over time.

The basic movement analysis process is the result from many years of research from the Weidenhielm group at Karolinska Institute. Sectra has in recent years created motion analysis products, see https://sectra.com/medical/product/sectra-ima/. and for CTMA, see https://sectra.com/medical/product/sectra-ctma/).

It is also noted that Radiostereometric Analysis (RSA) has been used for evaluating implanted devices over time. Thus, for some applications RSA can be seen as an alternative to IMA and CTMA. However, RSA is mainly used as a research tool, rather than a clinical tool, due to its complexity and cost and the fact that patients need to be given special implants if they are to be a part of an RSA study, something which is not the case for patients included in IMA and CTMA studies.

Examples of articles describing implant analysis are listed in this paragraph and incorporated by reference as if recited in full herein. Acetabular component migration in total hip arthroplasty using CT and a semiautomated program for volume merging, Olivecrona et al, Acta Radiologica, 2002. Stability of acetabular axis after total hip arthroplasty, repeatability using CT and a semiautomated program for volume fusion, Olivecrona et al., Acta Radiologica, 2003. Assessing Wear of the Acetabular Cup Using Computed Tomography: an ex vivo Study, Olivecrona et al., Acta Radiologica, 2005. A new technique for diagnosis of acetabular cup loosening using computed tomography: Preliminary experience in 10 patients, Olivecrona et al., Acta Orthopaedica, 2008. Motion analysis of total cervical disc replacements using computed tomography: Preliminary experience with nine patients and a model, Svedmark et al., Acta Radiologica, 2011. Computed Tomography vs. Digital Radiography Assessment for Detection of Osteolysis in Asymptomatic Patients With Uncemented Cups: A Proposal for a New Classification System Based on Computer Tomography, Sandgren et al., The Journal of Arthroplasty, 2013. A CT method for following patients with both prosthetic replacement and implanted tantalum beads: preliminary analysis with a pelvic model and in seven patients, Olivecrona et al., Journal of Orthopaedic Surgery and Research, 2016.

SUMMARY OF EMBODIMENTS OF THE INVENTION

Embodiments of the invention provide systems, methods and/or image processing circuits that provide technological improvements to the conventional IMA/CTMA process which can make the systems more useful and reliable in clinical settings.

Embodiments of the invention provide technological improvements in automated implant analysis systems that can result in efficiency, making user handling as well as novice training faster, and providing precision in motion detection, increasing the quality of the decision support on possible revision surgery or on assessment on implant function.

Embodiments of the invention can provide automated analysis systems that can generate relevant measurements of implants across batches of patient images and provide quality assurance overview summaries to allow a user to review the analysis and confirm the measurements are done correctly.

Embodiments of the invention provide automated analysis systems and methods that can connect CT image stacks to be compared; tune parameters for segmenting bone and metallic implants in the images; and select which segmented objects, or parts of objects, that are used as registration and measurement targets.

Embodiments of the invention provide automated implant analysis methods that include: obtaining a batch of image data sets of a plurality of different patients having an implant coupled to bone; providing a first data set of a first patient from the batch of image data sets, the first data set comprising a first image stack and a second image stack; allowing a user to select parameter settings for implant movement analysis of the implant including selecting a first object of interest and a second reference object; segmenting the first image stack and the second image stack to identify corresponding object pairs of the first object and the second object; registering each of the identified object pairs; automatically calculating measurements of movement of the implant and/or coupled bone after the registration; automatically propagating the selected parameter settings to other image data sets of other patients of the batch of image data sets; and electronically automatically repeating the segmentation, registration and calculated measurements for the batch of image data sets of others of the different patients.

The first object can be a target study object. One of the first object and the second reference object can be the implant. The parameter settings can include relating a coordinate system to the reference object, and identifying which measurements are to be calculated such as rotation and location of selected points of interest of the target study object.

After the first data set is analyzed, for identifying the first and second objects in the image data sets of the others of the different patients before a respective registration, the implant and associated position can first be automatically electronically identified, then the second object can be identified using the implant position as guidance.

The method can further include automatically electronically defining a cohort analysis template based on the user selected parameter settings and the first object and the second reference object of the data set of the first patient. The cohort analysis template can be used to automatically propagate the selected parameter settings to the other image data sets thereby using identical parameter settings across all comparisons provided by the calculated measurements.

The method can further include providing a display of results of the calculated measurement of movement of the implant in the batch of image data sets.

The method can further include providing a visualization of an aggregated view of overlying registered images of image data sets of the different patients with overlapping regions visually deemphasized relative to outliers.

The overlapping regions can have a reduced optical opacity relative to the outliers or can be presented translucent or transparent.

The visualization can be presented with sub-regions shown with different opacities or contrast. Different sub-regions are shown with an opacity and/or contrast that is inversely proportional to a number of objects overlapping in a respective sub-region.

The method can further include displaying thumbnail images of registered objects of different patients, optionally sorted by amount of calculated measurement of movement.

The method can further include electronically linking thumbnail images to an aggregated view of all the registered objects of the different patients and allowing a user to navigate from a selected thumbnail image to the aggregated view, optionally with the selected thumbnail image visually emphasized in the aggregated view relative to other registered images of other thumbnail images.

The segmenting step can be carried out automatically. The method can further include automatically repeating the segmenting step using different tuning parameters before the registering step to thereby provide more accurate segmentation of the first and second objects.

The method can further include, before the segmenting step, automatically selecting relevant image stack pairs from the first and second patient image stacks. The image stack pairs can have the first and/or second object.

The method can further include providing an electronic implant blueprint corresponding to the implant. One or more of the segmenting, registering or calculating measurements can be carried out using the electronic implant blueprint.

The method can further include providing an electronic implant blueprint corresponding to the implant. The segmenting can be carried out a plurality of times for the first data set using a plurality of different threshold levels that varies noise levels to match the blueprint with the segmented first and/or second object.

The method can further include providing an electronic implant blueprint corresponding to the implant. The registration can include matching point clouds of points generated on one or more surfaces of the first and/or second object.

The method can further include: providing an electronic implant blueprint corresponding to the implant; defining points on the electronic implant blueprint where measurements are to be made; and transferring the defined points to an image-domain implant. The registration can be carried out using the defined points.

The method can further include: providing an electronic implant blueprint corresponding to the implant; electronically defining reference points on the electronic implant blueprint; then electronically translating the blueprint reference points to the segmented implant object. The automatically calculating measurements of movement of the implant and/or coupled bone after the registration can be carried out using the translated blueprint reference points.

The method can further include: providing an electronic implant blueprint corresponding to the implant; and electronically defining focus surface locations on the electronic implant blueprint. Before the registration, the method can include automatically electronically translating the blueprint focus surface locations to corresponding locations on segmented first and/or second object, then generating an unevenly distributed point cloud with higher concentration at focus surface locations, then performing the registration using the generated point cloud.

Before the registration, the method can include automatically electronically deriving shape characteristics across one or more surfaces of a segmented first and/or second object, then electronically defining high curvature locations as focus surface locations, then electronically generating an unevenly distributed point cloud with higher concentration at focus surface locations. The registration can be carried out by electronically performing the registration using the generated point cloud.

The method can further include: providing an electronic implant blueprint corresponding to the implant in the first patient; electronically comparing a segmented first or second reference object to the implant blueprint; and adjusting segmentation parameters and repeating the segmentation of the first data set.

A workstation with an image processing circuit or in communication with an image processing circuit configured to carry out any of the method steps described herein.

Embodiments of the invention are directed to automated implant analysis methods that: obtain first and second sets of patient image stacks of a patient having at least one implant coupled to bone; segment bone and/or the at least one implant in the first and second image stacks to define segmented whole objects and/or segmented parts of objects; automatically select which segmented whole objects and/or segmented parts of objects to use as registration and measurement targets; register the selected relevant image stack pairs from the first and second patient image stacks using the selected segmented whole objects and/or the segmented parts of objects; and use the registered selected segmented whole objects and/or parts of objects to display or automatically measure movement of the implant.

The segmenting can be carried out automatically.

The method can further include automatically repeating the segmenting step using different tuning parameters before the registering to thereby provide more accurate segmented whole objects and/or segmented parts of objects for the registration.

The segmenting bone and the at least one implant can be carried out a plurality of times using a plurality of different threshold levels that varies noise levels and amount of bone included in the defined segmented whole objects and/or the segmented parts of objects.

The method can further include, before the segmentation, automatically selecting relevant image stack pairs from the first and second patient image stacks. The image stack pairs typically have at least one common target object or part of a target object for analysis therein.

The automatic selection can be carried out to select an entire implant as one of the segmented whole objects as a registration target for the registration step.

The automatic selection of which segmented whole objects and/or segmented part of objects to use as registration and measurement targets can be carried out to select part of the implant as one of the segmented parts of objects as a registration target for the registration.

The automatic selection of which segmented objects and/or segmented part of objects to use as registration and measurement targets can be carried out by automatically electronically matching segmented whole and/or partial bone objects to pre-defined templates of target objects.

The automatic selection of which segmented objects and/or segmented part of objects to use as registration and measurement targets can include automatically electronically matching segmented whole and/or parts of implant objects to pre-defined templates of target whole and/or parts of objects, optionally aided by segmented bone objects.

The automatic selection of which segmented objects and/or segmented part of objects to use as registration and measurement targets can include automatically electronically creating a set of different analysis targets for movement analysis based on the selected segmented whole objects and/or segmented parts of objects matched to pre-defined templates of target whole and/or partial objects.

The method can further include automatically grouping matched objects according to pre-defined templates of target whole and/or partial object groups.

The method can further include automatically electronically creating a set of different analysis targets for movement analysis based on segmented whole objects and/or segmented parts of objects matched to pre-defined templates of target whole and/or partial objects.

The method can further include electronically removing or omitting a part of the anatomy of the patient in the relevant pairs of image stacks before the registration.

The method can further include, before the automatic selection, automatically removing or discarding non-relevant objects and/or parts of objects from a larger set of segmented objects and/or segmented parts of objects.

The method can further include providing an electronic implant blueprint corresponding to the implant in the patient. One or more of the segmentation, selection, registration or measurements can be carried out using the electronic implant blueprint.

The method can further include: providing an electronic implant blueprint corresponding to the implant in the patient; electronically defining reference points on the electronic implant blueprint; then electronically translating the blueprint reference points to the segmented implant object. The automatic calculation of measurements of movement of the implant and/or coupled bone after the registration can be carried out using the translated blueprint reference points.

The method can further include providing an electronic implant blueprint corresponding to the implant in the patient; and electronically defining focus surface locations on the electronic implant blueprint. Before the registration, the method can include automatically electronically translating the blueprint focus surface locations to corresponding locations on segmented implant objects and/or parts of objects, then generating unevenly distributed point cloud with higher concentration at focus surface locations, then performing the registration using the generated point cloud.

The method can include, before the registration, automatically electronically deriving shape characteristics across one or more surfaces of a segmented implant object and/or a segmented part of implant object as one or more of the segmented whole objects and/or segmented parts of objects, then electronically generating unevenly distributed point cloud with concentration varying according to shape curvature, then electronically performing the registration using the generated point cloud.

The method can include providing an electronic implant blueprint corresponding to the implant in the patient; electronically comparing a segmented implant object to the implant blueprint; and adjusting segmentation parameters and repeating the segmentation.

Other embodiments are directed to an automated implant analysis methods that includes: obtaining first and second sets of patient image stacks of a patient having at least one implant coupled to bone; automatically identifying objects as relevant analysis targets, each analysis target associated with at least one relevant stack pair; automatically performing movement analysis for each identified analysis target; electronically storing an analysis target set of different analysis targets and associated movement analysis results; allowing a user to select an analysis target from the analysis target set; and displaying the movement analysis result of the selected analysis target.

Yet other embodiments are directed to automated implant analysis methods that include: obtaining first and second sets of patient image stacks of a patient having at least one implant coupled to bone; segmenting bone and/or the at least one implant in the first and second image stacks to define segmented whole objects and/or segmented parts of objects; automatically electronically deriving shape characteristics for the segmented whole objects and/or segmented parts of objects; automatically electronically using the shape characteristics to calculate risk of registration errors; use the registration error risk for automatic or manual selection of segmented whole objects and/or segmented parts of objects to use as registration and measurement targets; registering the selected relevant image stack pairs from the first and second patient image stacks using the selected segmented whole objects and/or the segmented parts of objects; and using the registered selected segmented whole objects and/or parts of objects to display or automatically measure movement of the implant.

Still other embodiments are directed to automated orthopedic analysis methods that include: obtaining first and second sets of patient image stacks of a patient; segmenting bone in the first and second image stacks to define segmented whole objects and/or segmented parts of objects; automatically selecting which segmented whole objects and/or segmented parts of objects to use as registration and measurement targets; and registering the selected relevant image stack pairs from the first and second patient image stacks using the selected segmented whole objects and/or the segmented parts of objects; and using the registered selected segmented whole objects and/or parts of objects to display or automatically measure movement of the bone.

Embodiments of the invention are directed to workstations that can be configured to carry out any of the methods, or portions thereof, described herein.

Embodiments of the invention are directed to image processing circuits that are configured to carry out any of the methods, or portions thereof, described herein.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1D and 1E are images of different blendings of the two image stacks which can be shown serially and quickly to identify movement or small spatial differences of objects close to the implant.

FIG. 3 is an example image stack according to embodiments of the present invention.

FIG. 4 is an example image stack pair according to embodiments of the present invention.

FIG. 5 is an example of objects in a respective image stack pair according to embodiments of the present invention.

FIG. 6 is an example implant blueprint (e.g., CAD drawing) of an implant under analysis according to embodiments of the present invention.

FIG. 15 shows a display with a plurality of thumbnail images of CT stacks of a patient with an implant that can be automatically paired according to embodiments of the invention, where stack number S1 and S3 are relevant to pair together.

FIGS. 29A-29C are symbolic visualizations of example point cloud generation useful for representing a target object according to embodiments of the present invention.

FIGS. 30A-30C are illustrations of example templates for measurement objects according to embodiments of the present invention.

FIGS. 31A-31E are illustrations of an example target template collection according to embodiments of the present invention.

FIGS. 33A-33C are example illustrations of a user interface providing an aggregated view of different patient images according to embodiments of the present invention.

DETAILED DESCRIPTION OF EMBODIMENTS OF THE INVENTION

Figure 1A:
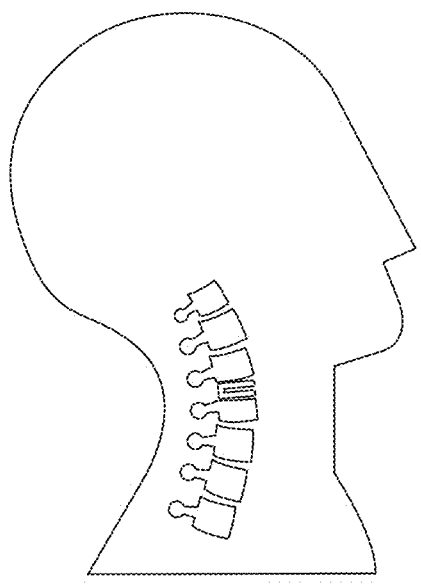
FIGS. 1A and 1B are schematic illustrations of examples of two images of a patient with an implant acquired with different physical provocations (with the stacks symbolically represented by a single 2D slice).

The present invention will now be described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise. The term "Fig." (whether in all capital letters or not) is used interchangeably with the word "Figure" as an abbreviation thereof in the specification and drawings. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. Like numbers refer to like elements throughout. In the figures, the thickness of certain lines, layers, components, elements or features may be exaggerated for clarity. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. The phrase "in communication with" refers to direct and indirect communication. Although described or shown with respect to one embodiment, the features so described or shown can apply to other embodiments.

The terms "circuit" and "module" are used interchangeably and refer to software embodiments or embodiments combining software and hardware aspects, features and/or components, including, for example, at least one processor and software associated therewith embedded therein and/or executable by the at least one processor and/or one or more Application Specific Integrated Circuits (ASICs), for programmatically directing and/or performing certain described actions, operations or method steps. The circuit or module can reside in one location or multiple locations, it may be integrated into one component or may be distributed, e.g., it may reside entirely in a workstation or single computer, partially in one workstation, cabinet, computer, or server and/or totally in a remote location away from a local display at a workstation. The circuit or module can communicate with a local display, computer and/or processor, over a LAN, WAN and/or internet to transmit images or analysis results.

The term "automatically" means that the operation can be substantially, and optionally entirely, carried out without human or manual input, and is typically programmatically directed and/or carried out. The term "electronically" includes both wireless and wired connections between components. The term "programmatically" means that the operation or step can be directed and/or carried out by a (digital signal) processor and/or computer program code. Similarly, the term "electronically" means that the step or operation can be carried out in an automated manner using electronic components rather than manually or using merely mental steps.

The term "clinician" refers to a physician or other personnel desiring to review medical data of a subject, which is typically a live human or animal patient.

The term "user" refers to a person, or device associated with that person, that uses the noted feature or component, such as a technician, orthopedic doctor or other clinician, researcher or expert.

The term "about" means that the recited parameter can vary from the noted value, typically by +/−20%.

The term "PACS" refers to PICTURE ARCHIVING AND Communication System.

The term "magnification" means the image resolution measured in micrometers per pixel, applicable both for the scanned image and the images displayed on screen. Higher magnification corresponds to a lower micrometer per pixel value than lower magnification and vice versa.

The term "semi-automated" refers to an image processing system, method, module or circuit that employs user (e.g., orthopaedic doctor) input to perform certain functions such as one or more of: initiate an analysis, select an implanted implant of interest, or review results of a single patient movement analysis or batch movement analysis of aggregate or individual analysis generated by automated systems.

As is well known to those of skill in the art, the term "registration" and/or "register" refers to an electronic process that aligns two or more images taken at different times from common or different imaging equipment and/or sensors, typically from different orientations and/or angles, to geometrically align the images and/or objects or features in the images for analysis.

Generally stated, the present invention provides technological improvements to conventional manual-based systems. The registration process can be automated in a manner that allows most of the problems associated with manual-based systems to be side-stepped or avoided. For example, embodiments of the present invention may provide automated analysis with fewer mistakes than a manual process. Techniques and systems described herein may increase precision and/or reduce mistakes by avoiding suboptimal, inconsistent, and/or incorrect segmentation parameters. Similarly, techniques and systems described herein may increase precision and/or reduce mistakes by avoiding a suboptimal, inconsistent, and/or incorrect definition of registration and/or measurement targets. Techniques and systems described herein may utilize an implant blueprint to increase accuracy and precision in implant movement measurement. Unlike manual processes, techniques and systems described herein may generate point clouds for representations of implants, which may increase precision in registration and thereby in movement measurement. Each automation step can be applied in isolation or in any combination.

Referring to FIGS. 3-6, examination inputs are provided to the automated image analysis system 10. The inputs include image stacks 100 which can be analyzed to identify stack pairs 100p and relevant objects in the relevant image stacks 105 can be automatically identified. The term "image stacks" refers to slices of images of a patient that can be provided in stacks as is well known to those of skill in the art. The objects 105 that can be identified include target anatomy and implants. The term "stack pairs" refers to a respective slice from one image that correlates to a respective corresponding slice from a second image to provide the stack pairs.

FIG. 6 illustrates that an implant blueprint 35 can also be provided as an input useful for movement analysis, registration and/or segmentation. The term "implant blueprint" refers to a digital model of an actual physical implant (often referred to as a computer-aided design "CAD" model), in 3D or 2D that can be a scaled image or CAD drawing with dimensional and shape data. As will be discussed further below, the implant blueprint 35 can comprise one or more defined reference points R and/or focus surface locations F that can be used for one or more of segmentation, registration or measurements according to embodiments of the present invention.

The automated image analysis system 10 may display the images 100, image stack pairs 100p and/or objects 105 in the image stacks or image stack pairs. The system 10 can perform a registration with one or more targeted implants, i.e., rotating and translating one of the stacks such that the implant is in the same location in the different image stacks when images are overlaid.

Figure 1B:
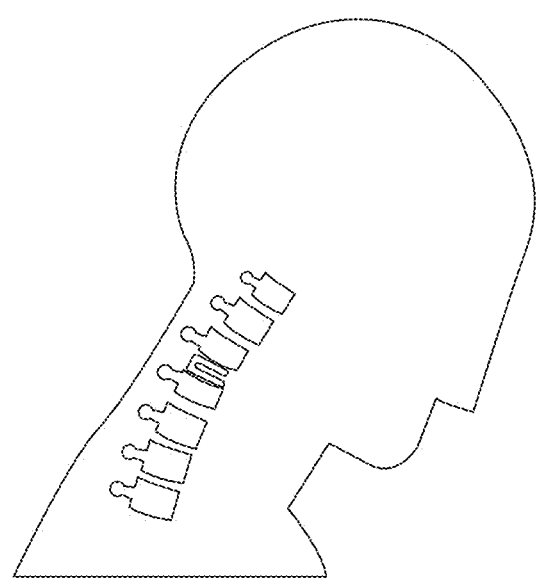
Figure 1C:
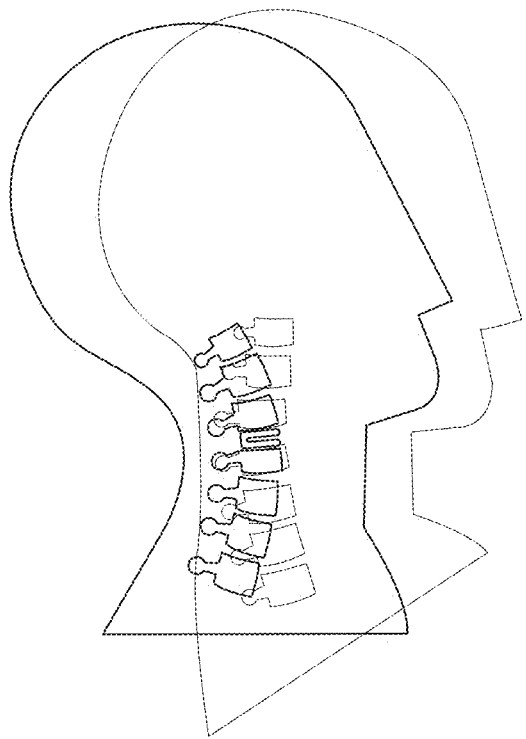
FIG. 1C is an example of the two image stacks being registered targeting the implant such that the implant is the same location when the images are overlaid.
Figure 2A:
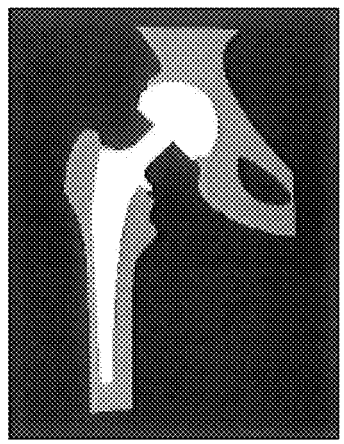
FIGS. 2A-2C are image stacks of a patient with an implant acquired at different time points (the stacks symbolically illustrated by a single 2-D slice).
Figure 2B:
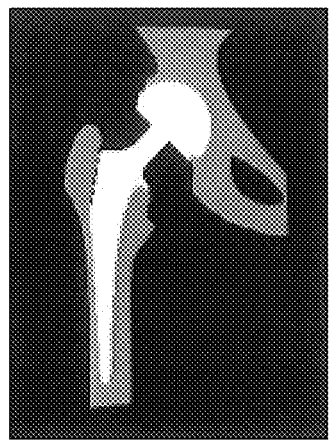
Figure 2C:
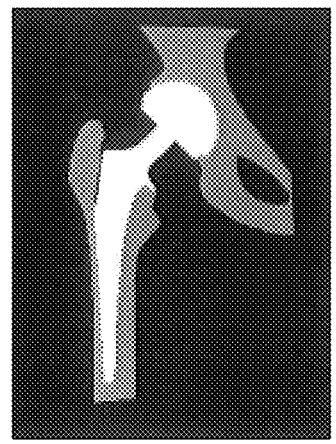
Figure 2D:
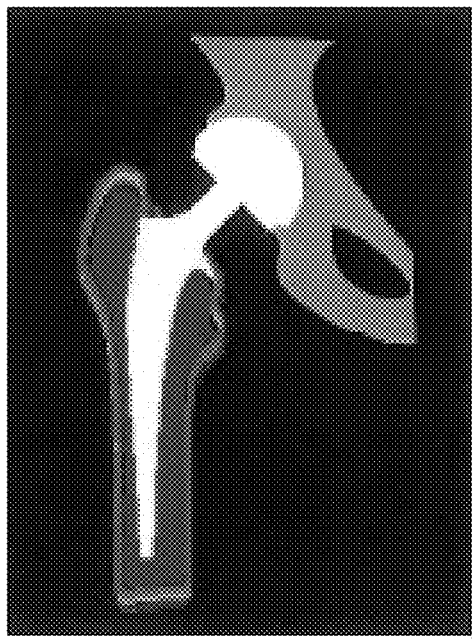
FIG. 2D is a visualization of a registration of the implant with contours in different colors representing different time points of the different images shown in FIGS. 2A-2C.
Figure 2E:
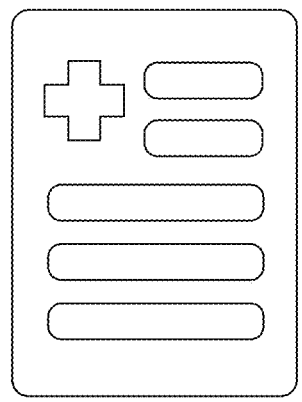
FIG. 2E is a report of quantitative measures of the migration over time in terms of translation and rotation and/or other movement according to embodiments of the present invention.

The system 10 can analyze CT image stacks that are acquired based on provocation or loading of a patient (FIGS. 1A, 1B) or CT image stacks acquired at several time points, typically months apart as shown in FIGS. 2A-2C. The stacks are symbolically represented by a single 2D slice. In this example, the implant stem can be a target object 105 (FIG. 5) that is analyzed and it is migrating down the bone (the bone is moving upwards). The system 10 can perform a registration of the implant and migration-relevant bone and provide a visualization that can identify movement of the implant shown with migration relevant bone (blue), optionally with contours of the migration relevant bone in different colors (i.e., green, orange and red) representing the time points of the implant in the different images. The system 10 can derive quantitative measures of the migration over time, in terms of translation and rotation, and present the results to a display 20.

While particularly suitable for analyzing CT images of CT image stacks, MRI images may also be evaluated by the automated system 10. Thus, while embodiments of the invention will be discussed with respect to CT stacks, MRI image stacks or slices may also be used.

Figure 7:
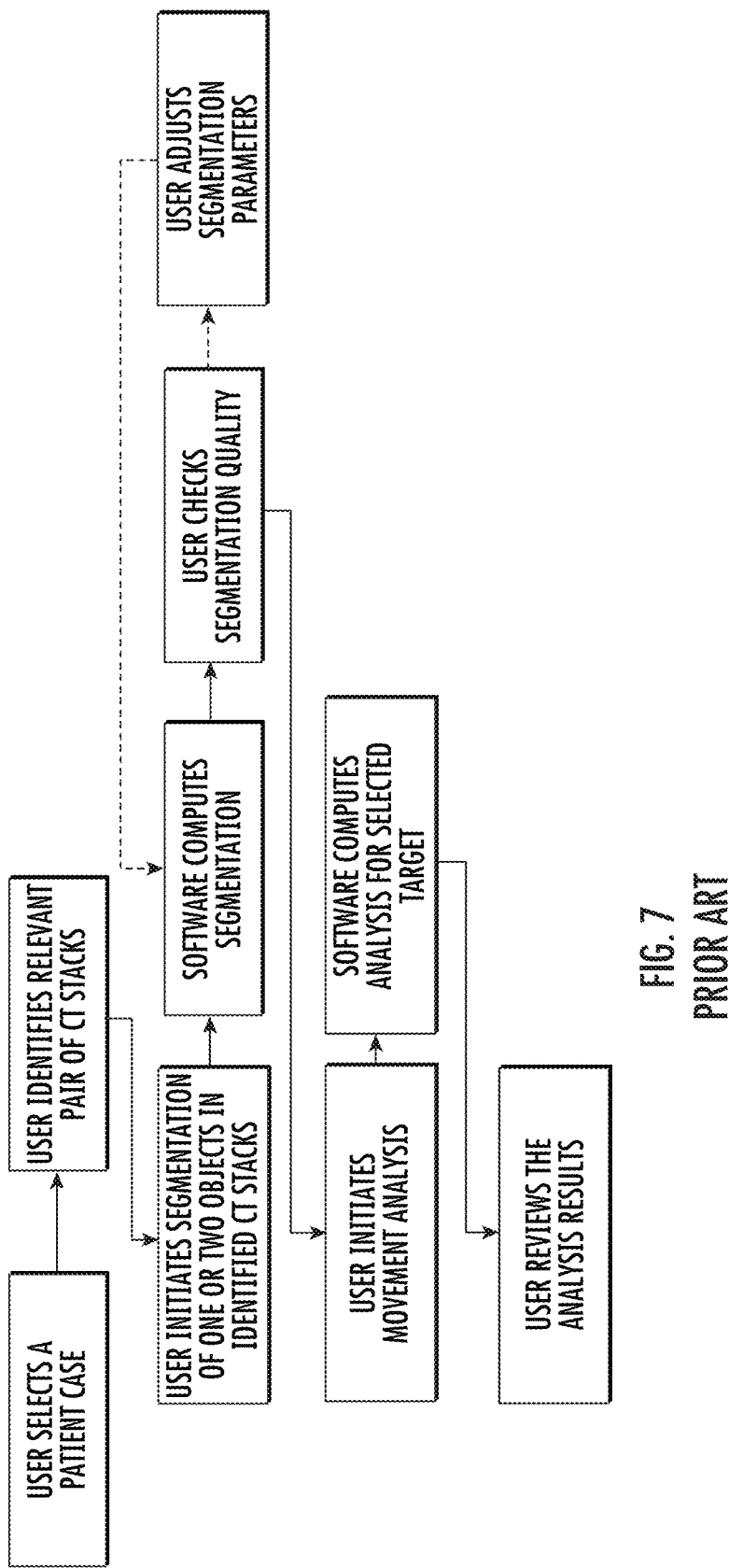
FIG. 7 is a flow chart of an overview of a prior art manual movement analysis method.
Figure 8:
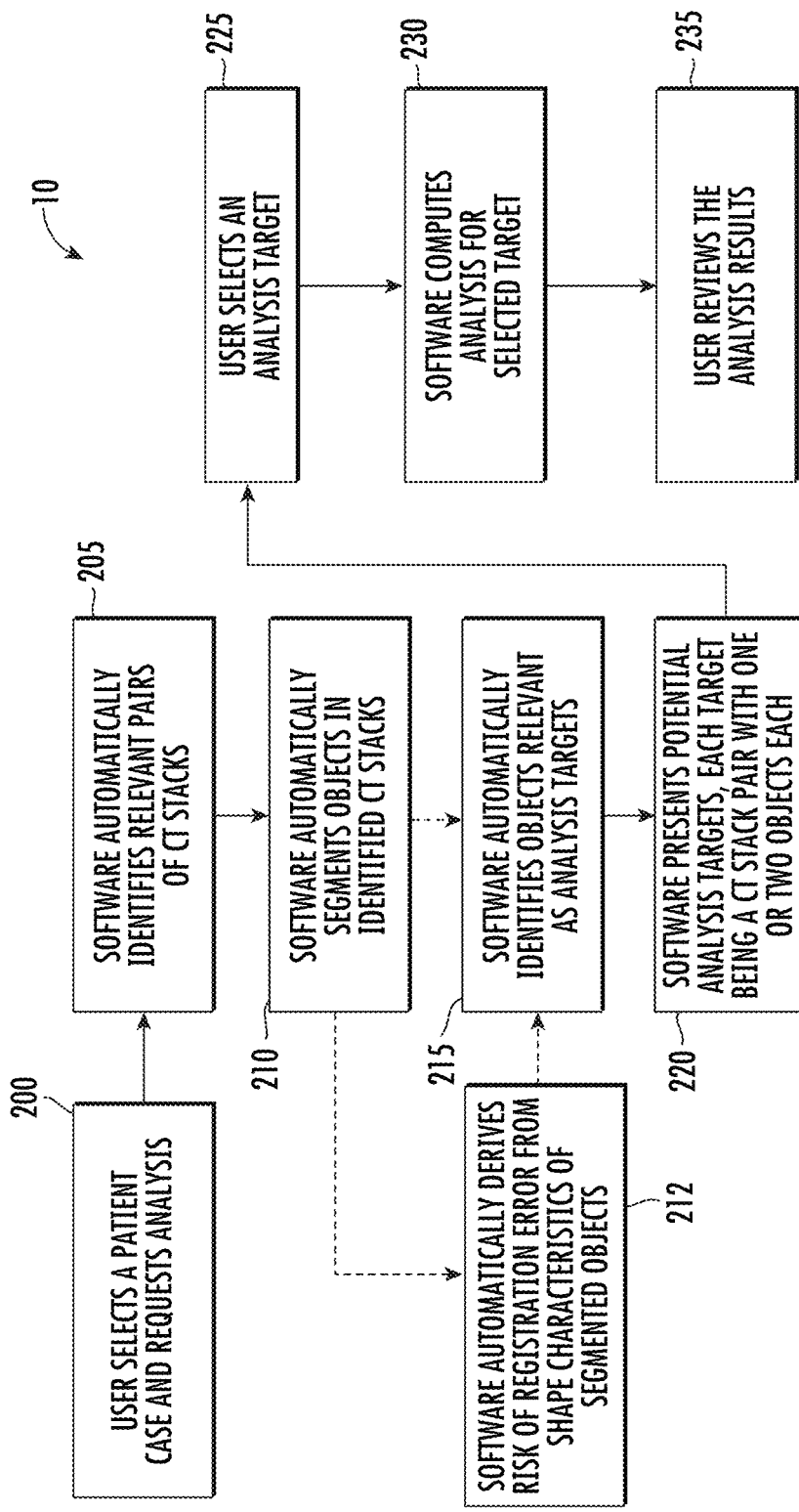
FIG. 8 is a flow chart of an automated movement analysis method according to embodiments of the present invention.

FIG. 7 illustrates an example overview of a prior art manual movement analysis system. Note the number of required user inputs. Each IMA process currently typically requires between 5-10 minutes of time to allow for manual settings and PC calculation time. In addition, the software requires relatively intensive training of 20+ hours of training for a new user (typically a radiologist or orthopaedic surgeon) to get to a proficient level at producing informative visualizations. Even after full training, the efficiency of the users in doing manual steps can vary. FIG. 8 is an overview of an example method provided by an automated movement analysis system 10. A user can select a patient case and request or initiate an automated analysis (block 200). Relevant pairs of CT stacks can be automatically identified (block 205). Objects in the identified CT stacks can be automatically segmented (block 210). Segmentation is well known to those of skill in the art. See, e.g., Digital Image Processing, Bernd Jähne, ISBN 3-540-67754-2, Springer-Verlag Berlin Heidelberg New York, the contents of which is hereby incorporated by reference as if recited in full herein.

Risk of error in subsequent registration of segmented objects can be automatically derived based on shape characteristics of the segmented objects (block 212).

Figure 32C:
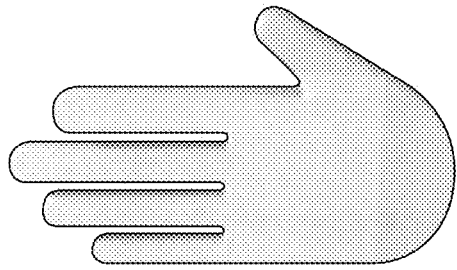
FIGS. 32A-32C are example symbolic shapes of objects representing differing degrees of registration risk according to embodiments of the present invention.
Figure 32B:
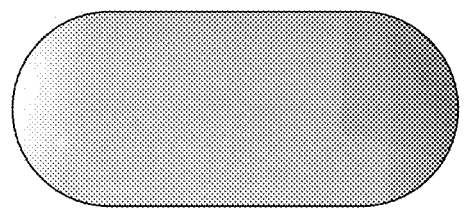
Figure 32A:
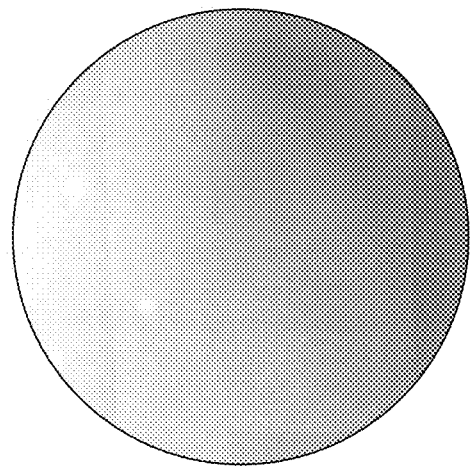

For example, the example method can provide the user with condition numbers, numbers which tell the user if it's likely a good registration can be achieved given the object's shape. For example, a sphere is associated with a poor condition number for rotation, while a shape that is asymmetrical in all dimensions can have a better condition number. FIGS. 32A-32C illustrate example target objects which will result in different condition numbers. FIG. 32A shows an object with a high risk of rotational registration error because of symmetry in all dimensions. An object with a high risk or rotational registration error around one axis (shown as a vertical axis in FIG. 32B) but low risk in other axes can be identified and this object may have a better condition number than the object shown in FIG. 32A. An object with a lower or lowest risk of registration error due to asymmetry in all dimensions can also be identified (FIG. 32C). These condition numbers can be generated during the automatic registration analysis and provided to a user (block 212). The condition numbers can be in a range of 0-10, 0-100 or other ranges, typically with the high end, such as "10", being associated with a high probability of good registration and a low end, such as "0", associated with a very low probability of good registration. The condition numbers can be a single number (shown as "0", "5" and "10" for FIGS. 32A, 32B, 32C, respectively) or provided as a set of numbers, one for each of the three axes, X, Y, Z (shown as "[0, 0, 0]", "[1, 9, 9]" and ["10, 10, 10"] for FIGS. 32A, 32B, 32C, respectively). Moreover, different condition numbers can be given for different parts of an object, such as a target implant object.

Objects in the segmented identified stacks can be automatically identified as relevant analysis targets (block 215). Potential analysis targets, each target being in a CT stack pair, typically with one or two (or more) objects for each target, can be automatically presented, typically on a display (block 220). A user can be allowed to select an analysis target from the potential analysis targets presented (block 225). The automated presentation can be via thumbnail images and the selection can be by touch screen input, mouse click or other user input. The computed analysis for selected targets can be carried out the results generated, optionally to a display screen (block 230). The analysis results can be provided to a user. A user can review the analysis results (block 235).

Figure 9:
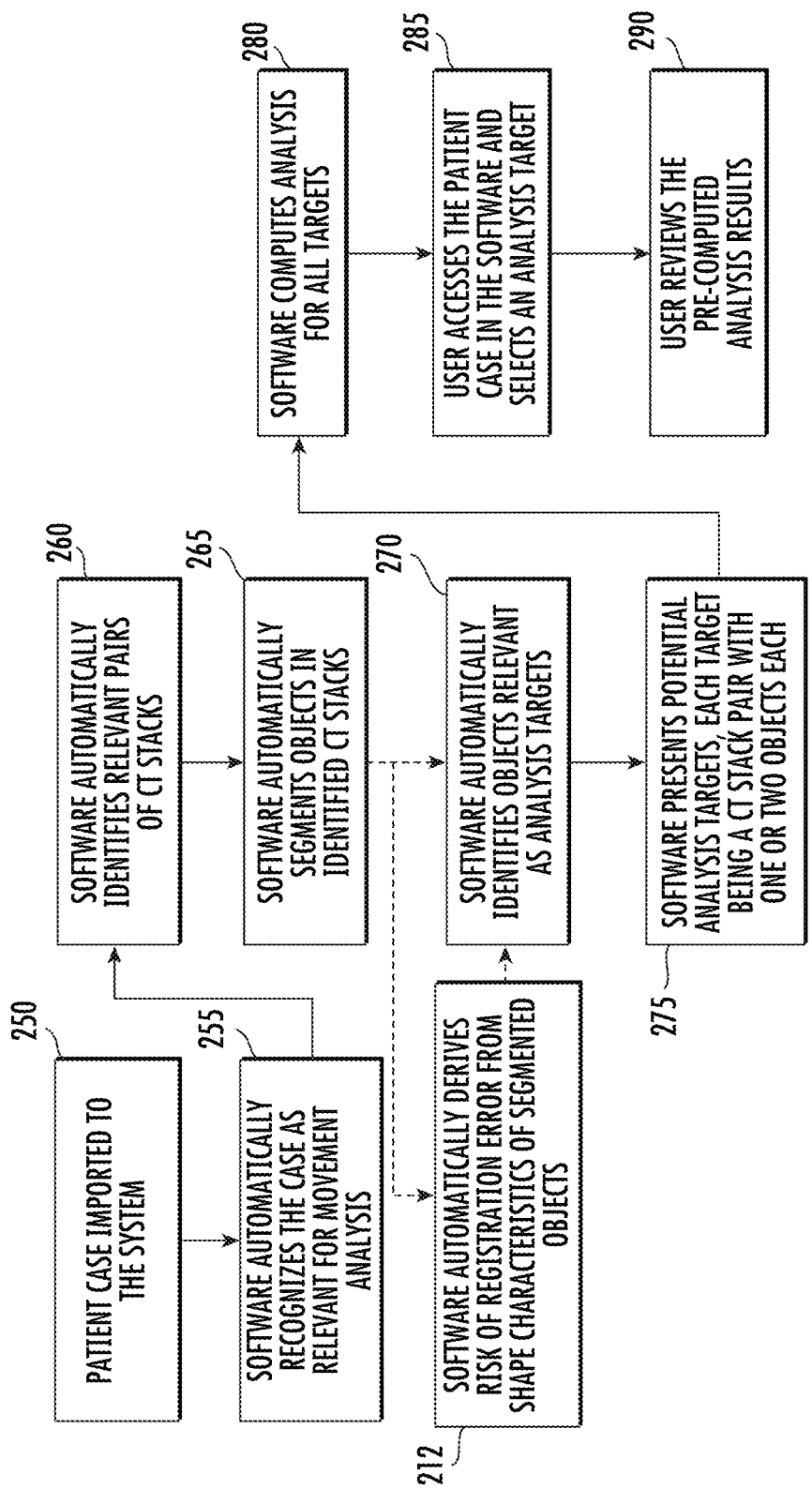
FIG. 9 is a flow chart of another automated movement analysis method according to embodiments of the present invention.

FIG. 9 is another example method that can be provided by an automated movement analysis system 10 according to embodiments of the present invention. A patient case can be imported or otherwise provided to the system (block 250). The case can be automatically recognized as relevant for movement analysis (block 255). Relevant pairs of CT stacks can be automatically identified (block 260). Objects in the identified pairs of CT stacks can be automatically segmented (block 265). As discussed above, a risk of error in subsequent registration of segmented objects can be automatically derived based on shape characteristics of the segmented objects (block 212). Objects relevant as analysis targets can be automatically identified (block 270). Potential analysis targets, each target being a CT stack pair with one or two objects each can be presented. Potential analysis targets, each target being in a CT stack pair, typically with one or two (or more) objects for each target, can be automatically identified (block 275). All potential analysis targets identified can be analyzed automatically to provide a set of pre-computed analysis results for the patient case (block 280). A user can be allowed to access the patient case and select an analysis target from one of the identified and analyzed potential analysis targets (block 285). The user can review the pre-computed analysis results for the selected target (block 290).

Figure 10:
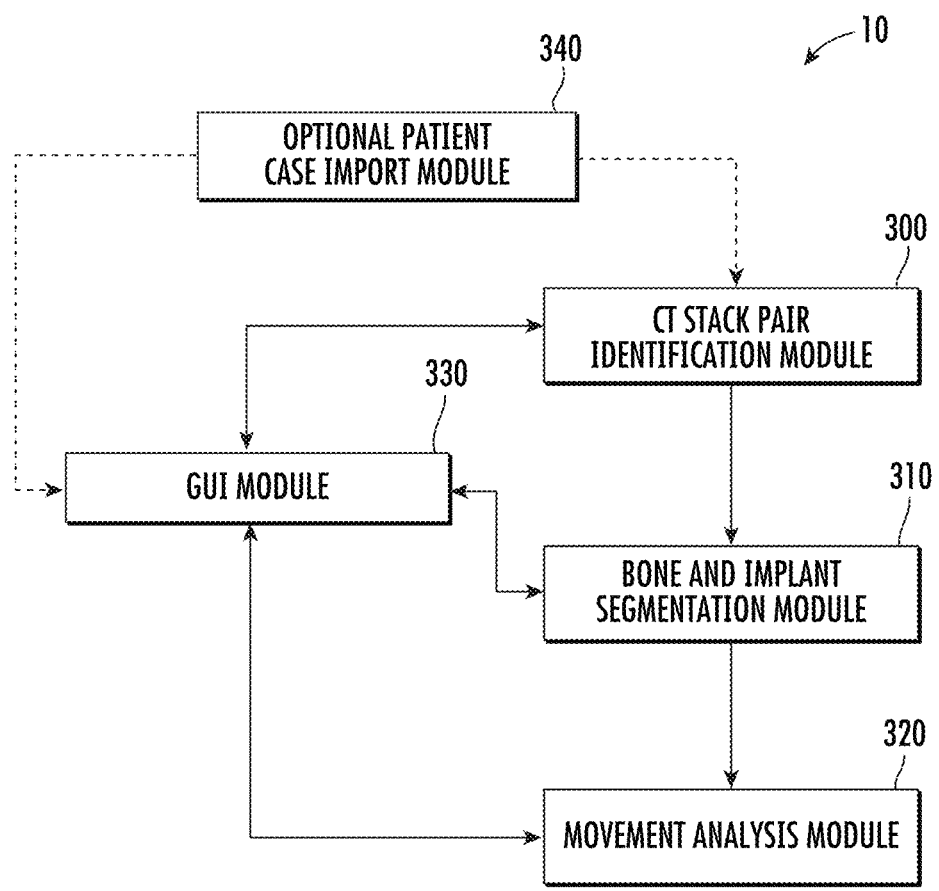
FIG. 10 is an example automated movement analysis system with modules according to embodiments of the present invention.

FIG. 10 is an example system 10 with a plurality of modules including a stack pair identification module 300, a bone and implant segmentation module 310, a movement analysis module 320, a GUI module 330 and optional patient case import module 340.

Figure 11:
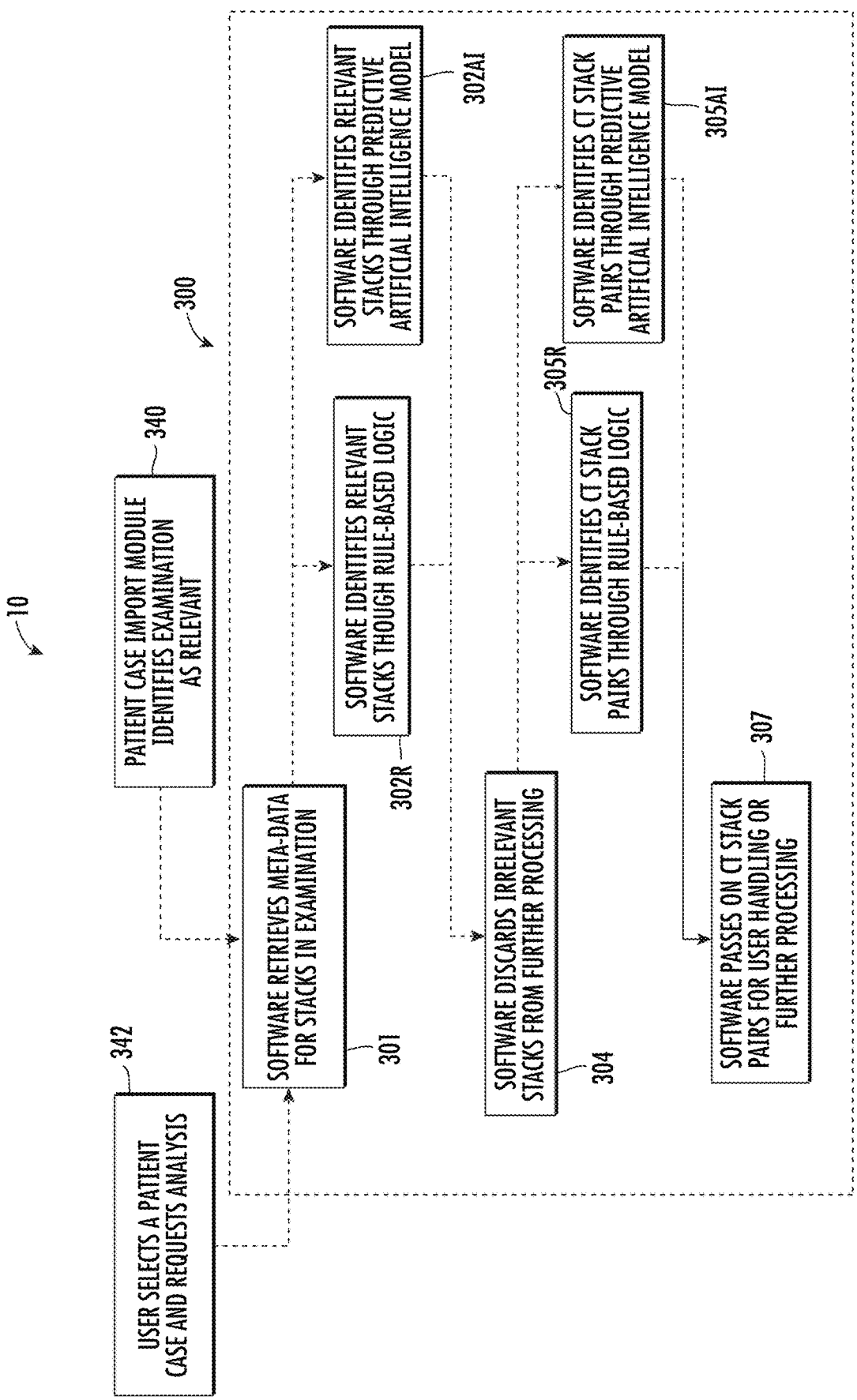
FIG. 11 is an example of a flow chart of an automated stack pair selection system according to embodiments of the present invention.

FIG. 11 illustrates that the system 10 can have an input 342 whereby a user selects a patient case and requests analysis and/or the patient case import module (block 340) identifies examination as relevant to initiate the analysis by the stack pair module (block 300).

The system 10, typically via the stack pair identification module 300, can be configured to retrieve meta-data for stacks in examination (block 301). Relevant stacks can be identified through rule-based logic (block 302R) and/or through a predictive artificial intelligence model (block 302AI).

In some embodiments, stack identification based on rule-based logic may utilize meta-data associated with the stacks, which may, for example, be elements in the DICOM standard format. Rules may be expressed as logical conditions, such as "if element A is equal to X and element B is equal to Y, the stack is suitable for processing." Rule-based pairing of stacks may also be based on conditions that certain elements are equal or similar between the two stacks.

In some embodiments, stack relevance and pairing may be done through artificial intelligence methods using meta-data such as, for example, DICOM elements. This could be done through document similarity methods based on vector space models, see, e.g., "Information Retrieval using Cosine and Jaccard Similarity Measures in Vector Space Model," Jain et al., International Journal of Computer Applications, Vol 164, April 2017, and "On modeling of information retrieval concepts in vector spaces," Wong et al., ACM Transactions on Database Systems, 1987, the contents of which are hereby incorporated by reference as if recited in full herein.

In some embodiments, an artificial intelligence model identifying relevant stacks may be based on predicting anatomic content from the image data, isolated from or in combination with the meta-data approach. Example methods for this purpose can be found in "CT scan range estimation using multiple body parts detection: let PACS learn the CT image content," Wang and Lundström, International Journal of Computer Assisted Radiology and Surgery, Vol 11, 2016, Springer Berlin Heidelberg, and "A survey on deep learning in medical image analysis," Litjens et al., Medical Image Analysis, Vol 42, December 2017, Elsevier, the contents of which are hereby incorporated by reference as if recited in full herein.

The system 10 can discard or mark irrelevant stacks to exclude irrelevant stacks from further processing (block 304). The system 10 can identify stack pairs through rule-based logic (block 305R) and/or through a predictive artificial intelligence model (block 305AI). The system 10 can pass on CT stack pairs for user handling and/or further processing (block 307). For example, the system can display the identified stack pairs in a display associated with a GUI.

Figure 12:
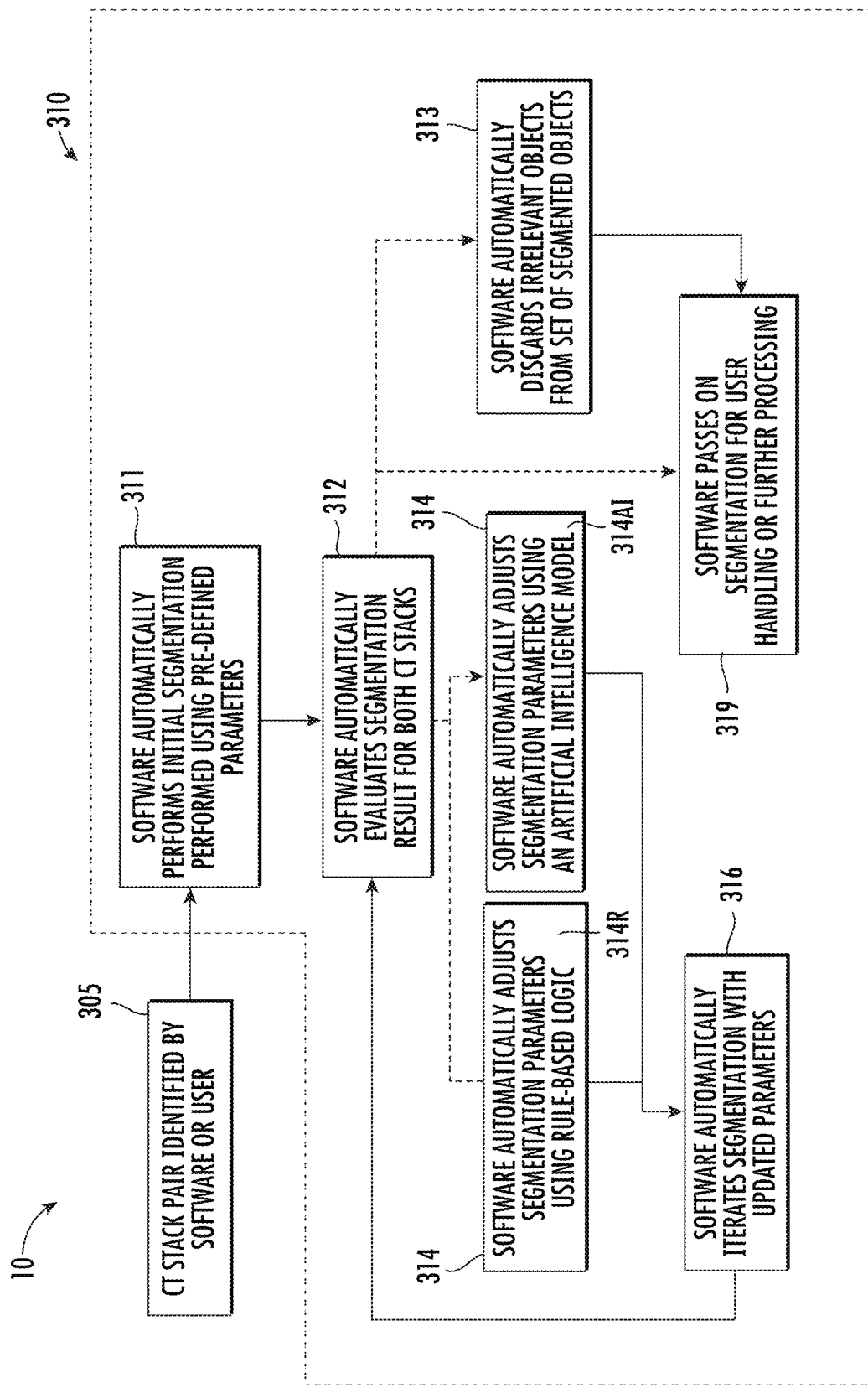
FIG. 12 is an example flow chart of actions for automated thresholding for segmenting CT stacks according to embodiments of the present invention.

FIG. 12 illustrates an example thresholding protocol that can be carried out by the system 10, optionally using the bone and implant segmentation module 310. A CT stack pair is identified by the system (block 305). The system 19 automatically performs initial segmentation performed using pre-defined parameters (block 311). The system 10 automatically evaluates segmentation result for both CT stacks (block 312). The system 10 automatically discards irrelevant objects from each set of segmented objects (block 313). The system automatically adjusts segmentation parameters (block 314) using rule-based logic (block 314R) and/or an artificial intelligence model (block 314AI). The system 10 automatically iterates segmentation with updated (adjusted) segmentation parameters (block 316).

In some embodiments, the initial segmentation can be done using modern machine learning approaches, such as those described in "A survey on deep learning in medical image analysis," Litjens et al., Medical Image Analysis, Vol 42, December 2017, Elsevier the contents of which are hereby incorporated by reference as if recited in full herein.

In some embodiments, the adjustment of segmentation parameters can be performed based on standard image processing techniques such as, for example, region growing (see W. K. Pratt, "Digital Image Processing 4th Edition", John Wiley & Sons, Inc., Los Altos, Calif., 2007) employing a Hounsfield value threshold the contents of which are hereby incorporated by reference as if recited in full herein.

In some embodiments, one option for such an adapted region growing approach may be, given the initial segmentation and a threshold value, to expand the segmented area to include neighboring voxels with Hounsfield values above the threshold and to shrink to exclude values below the threshold. The threshold Hounsfield value to use for the segmentation adjustment may be derived through a regression approach using an artificial intelligence model. The artificial intelligence model may be a convolutional neural network trained with image data having a best threshold value defined by human experts. After the segmentation adjustment, additional post-processing to smooth the resulting shape can be applied, for instance using morphological operations. Though segmentation adjustment utilizing region growing is provided as an example, embodiments of the present invention are not limited to this technique.

The system 10 can automatically pass on segmentation for user handling and/or further processing (block 319).

Figure 13:
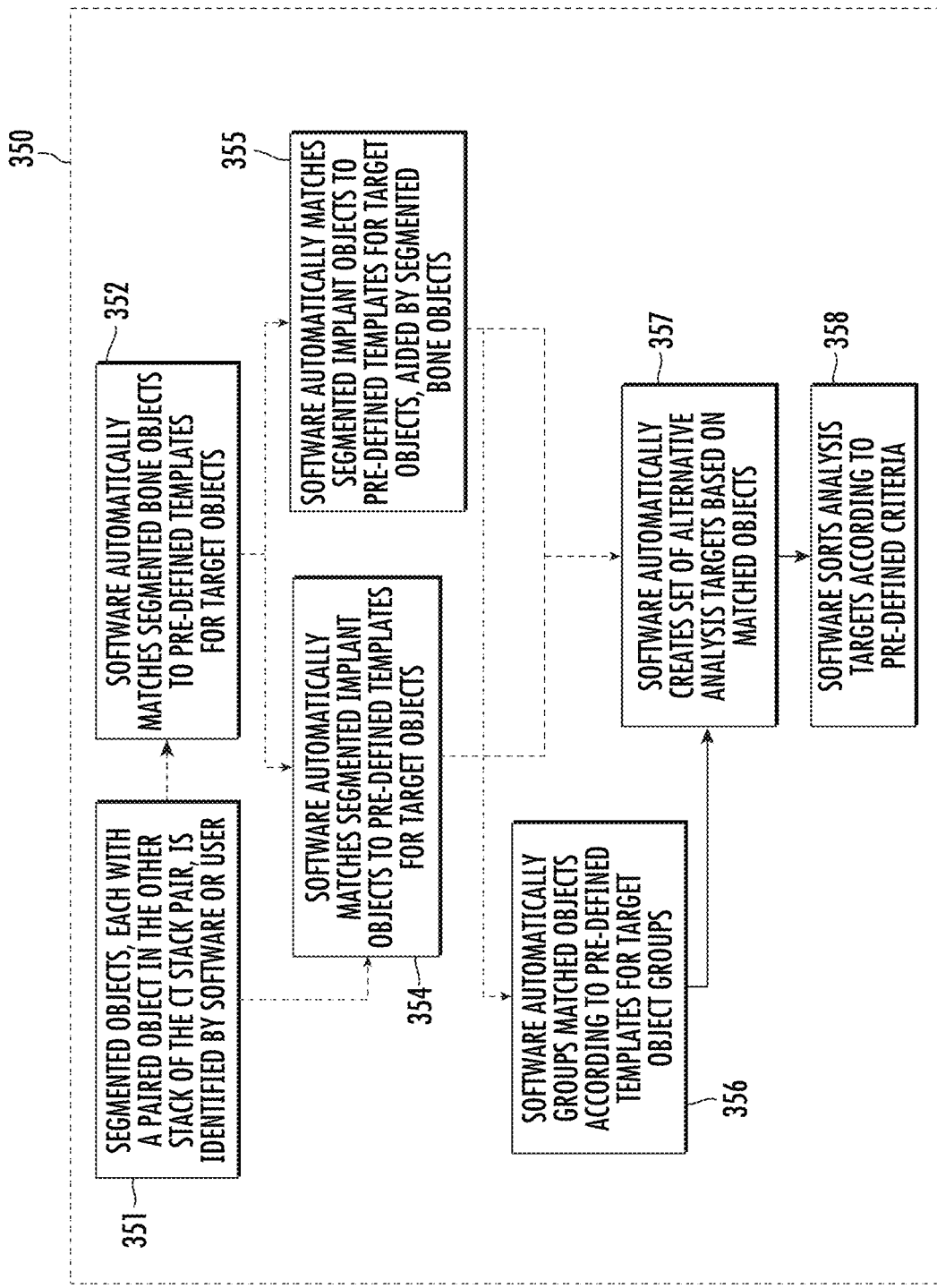
FIG. 13 is an example flow chart of actions for automated object selection of segmented objects according to embodiments of the present invention.

FIG. 13 illustrates an example object selection protocol that can be carried out by the system 10, optionally using an object selection module 350. The system 10 or a user can identify segmented objects, each a paired object in the other stack of the CT stack air (block 351).

The system 10 can automatically match segmented bone objects to pre-defined templates for target objects (block 352). The system 10 can automatically match segmented implant objects to pre-defined templates for target objects (block 354), optionally aided by segmented bone objects (block 355). The system can automatically group matched objects according to pre-defined templates for target object groups (block 356). The system 10 can automatically create sets of alternative analysis targets based on matched objects (block 357). The system 10 can sort analysis targets according to pre-defined criteria (block 358). The system can provide computed movement analysis results for the sets of analysis targets and a user can select an analysis target from the sets of analyzed targets and the system can provide pre-computed analysis results (blocks 285, 290, FIG. 9).

An example workflow is as follows:

1. Automated selection of CT stack pairs.

When a study is sent for movement analysis (by either automatic or manual routing), a computer algorithm sorts through the CT stacks for that examination (there may be many stacks in one exam).

The algorithm couples each stack pair that is relevant for movement analysis.

For instance, relevance can mean that provocation has been done, that the same CT acquisition parameters (such as reconstruction kernel) have been used, and that the time period between the two scans are relevant (1-30 min for IMA, a set number of months for CTMA).

The coupling can be done by rule-based logic or with Artificial Intelligence trained to look at stack meta-data (DICOM information) and/or image data.

2. Automated algorithm for thresholding of bone and metal.

The CT stack pairs from the previous step are sent to an algorithm which automatically performs segmentation of objects consisting of relevant materials, typically metal and bone.

The segmentation can be done in many ways, where a typical method component is thresholding, using ranges of CT voxel values (Hounsfield values) for the materials.

The segmentation can automatically adjust the thresholding to best fit the CT stack pair in question. This can, for instance, be achieved through an artificial intelligence algorithm trained to select the thresholds based on the image content, mimicking a gold standard result that an expert would accomplish.

The segmentation can be performed in parallel for both CT stacks in an image stack pair, to ensure that results are valid for both stacks and that the results are comparable.

The set of segmented objects can be filtered. Reasons to remove objects from further scrutiny could be that they are too small fragments to be relevant, that they reside in medically irrelevant locations, or that there is not a good match in size and shape to an object in the other CT stack in the pair.

3. Automated identification of target objects for analysis.
   The input to this step is that there are a number of segmented objects, each object existing in both CT stacks of a stack pair. In a manual workflow, the user would need to select analysis targets by clicking in the image view.
   According to embodiments of the invention, a list of possible analysis targets is automatically created. A target comprises of an object used for registration, and, optionally (in the quantitative setting), another object used for measurements.
   According to predefined analysis target types, the invention identifies which objects that correspond to the sought predefined targets.
   The identification of objects can be done by first identifying those corresponding to bone anatomy, and then identifying metal components aided by their position relative to anatomical objects (for instance, a metal object in close proximity to a pelvis is more likely to be a hip prosthesis cup than a shoulder implant).
   The object categorization can also include merging objects which should be treated as one object, for example two screws inserted in the same vertebra.
4. Automated initiation of analyses.
   The analyses for which relevant objects were found in the previous step are automatically initiated and their results are stored.
   The list of targets is presented to the user, who can review its results by selecting an item in the list.
   The analysis items can be presented as thumbnail views of images with the respective objects highlighted. The list can be sorted in order of relevance for the CT stacks in question.
When the above functions are in place, with substantially all necessary processing done automatically beforehand and stored as pre-computed analysis results for different target analysis sets, the system can be configured to allow an end user to have select inputs as follows.
   Select a patient case
   Initiate the analysis, for instance by a button/menu option connected to either of the two CT stacks, to the entire study, or to the patient
   Select the object(s) to analyze
      May be carried out through symbolic representations in a list, or by clicking the objects in the CT stack
      For qualitative analysis, a single object can be sufficient (the registration target), for quantitative analysis at least one other, i.e., second reference object is also needed (the measurement target)
   Review the registration results
      Adjustment options are available in case the automated procedure is not sufficient
Thus, embodiments of the invention can provide higher efficiency and precision over conventional systems in performing this type of implant movement analysis.

Figure 14:
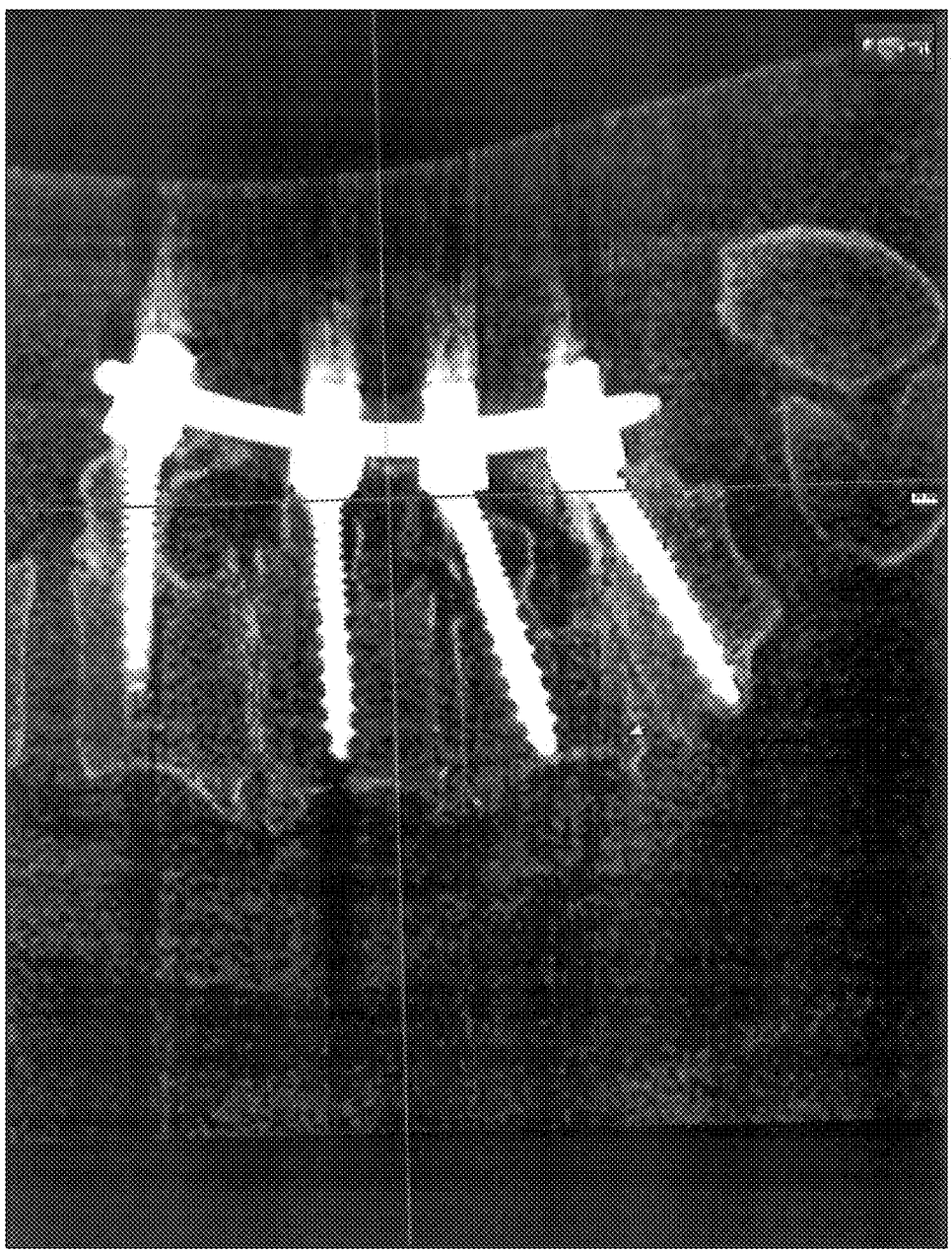
FIG. 14 is a CT image with an example implant, sagittal slice through a CT stack showing larger spine implant with four pedicle screws that can be analyzed by the automated implant movement systems and methods according to embodiments of the present invention.

FIG. 14 is an image of a CT implant example. This is a sagittal slice through a CT stack, showing larger spine implant with four pedicle screws.

FIG. 15 illustrates a plurality of image stacks for stack selection, with stacks numbers S1 and S3 relevant to pair.

FIGS. 16A-16E illustrate example segmentations.

Figure 16A:
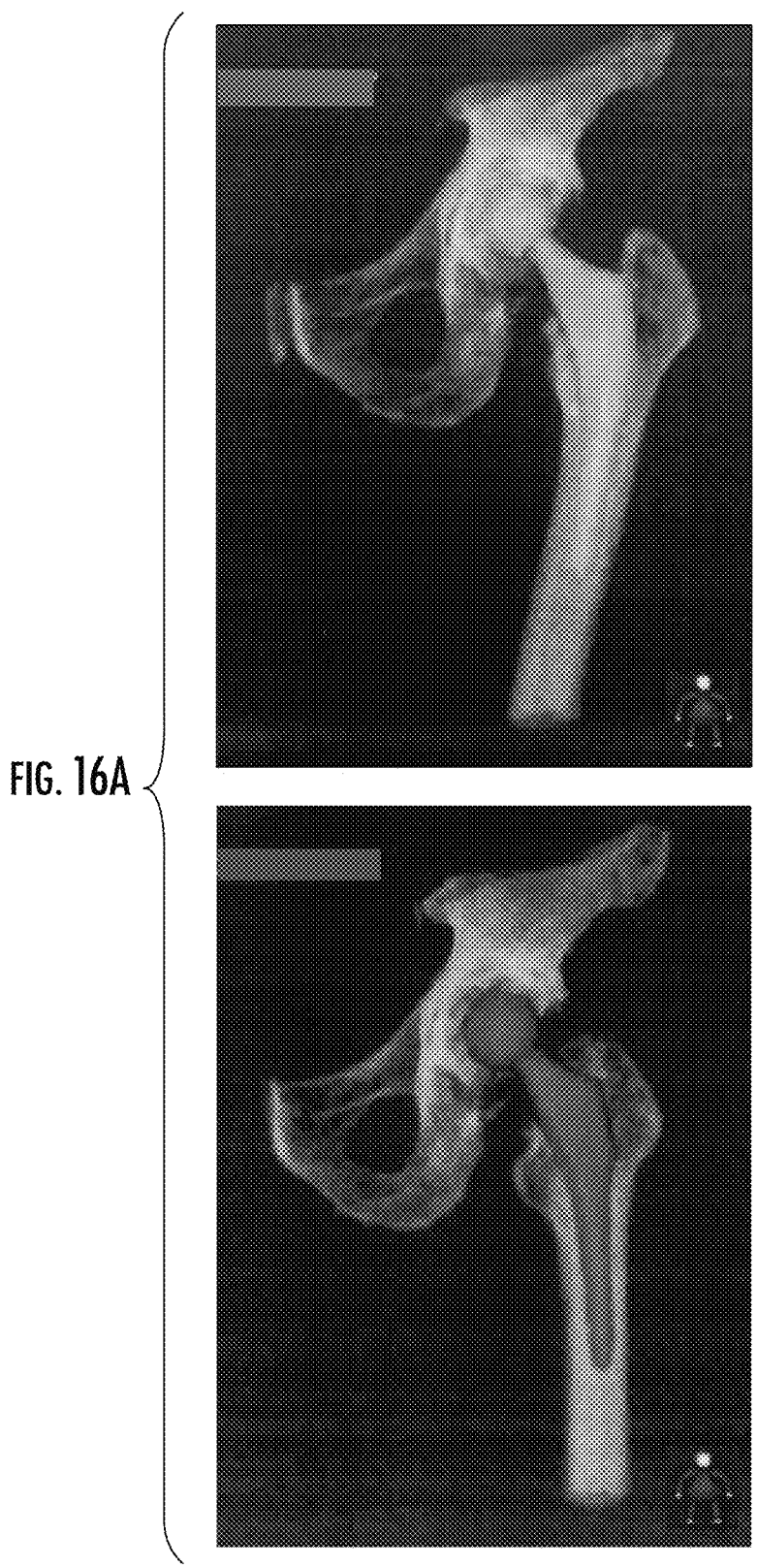
FIG. 16A is an example image of a hip implant having been automatically segmented with the same implant in the pair of CT stacks according to embodiments of the present invention.

FIG. 16A is an example CT stack pair with a hip implant shown as 3D renderings, the top stack with the patient's leg provoked inwards and the bottom stack with the patient's leg provoked outwards, and with the hip implant having been segmented (same patient and implant in both stacks).

Figure 16B:
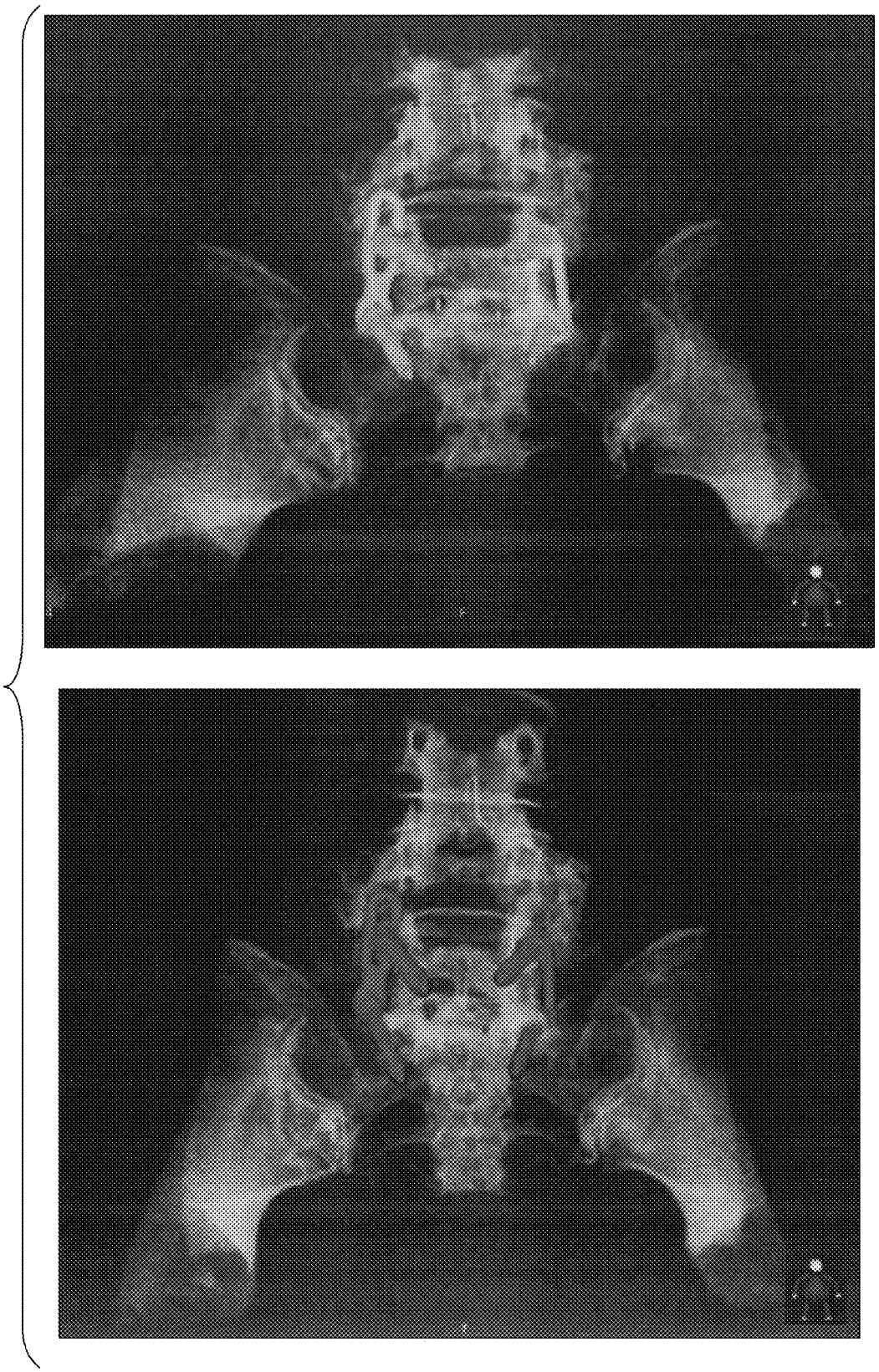
FIG. 16B is an example image of a spine implant having been automatically segmented with the same implant in the pair of CT stacks according to embodiments of the present invention.

FIG. 16B is an example CT stack pair with a spine implant shown as 3D renderings, the top and bottom stack with different provocations of the spine, respectively, and with the spine implant having been segmented (same patient and implant in both stacks).

Figure 16C:
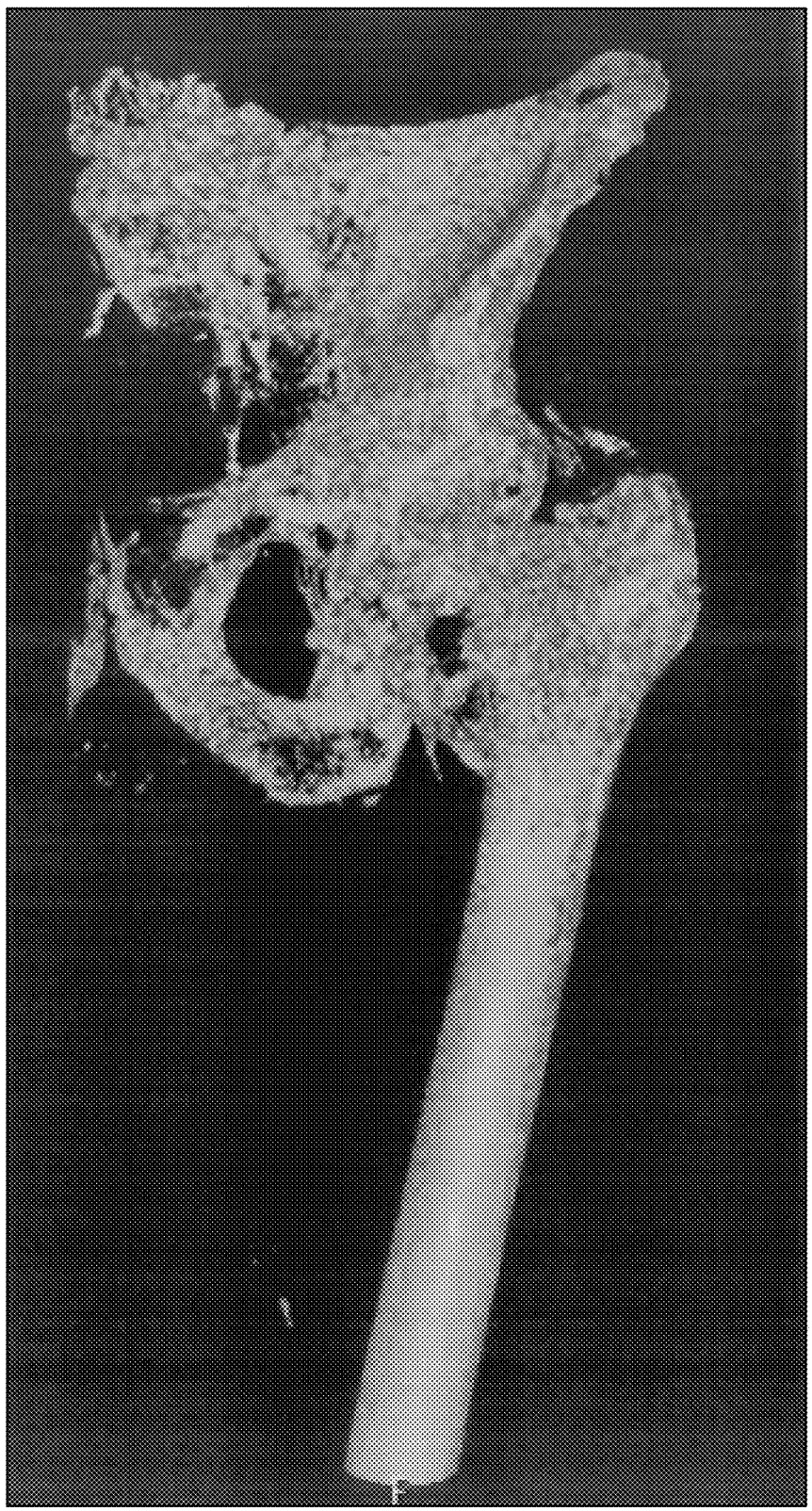
FIG. 16C is an example image automatically segmented at a first defined threshold with bone segmented at a high threshold value (not all bone included) according to embodiments of the present invention.
Figure 16D:
FIG. 16D is an example image automatically segmented at a second defined threshold, with bone segmented at a lower threshold value than in FIG. 16C (most bone included, also shown with some noise/non-bone) according to embodiments of the present invention.
Figure 16E:
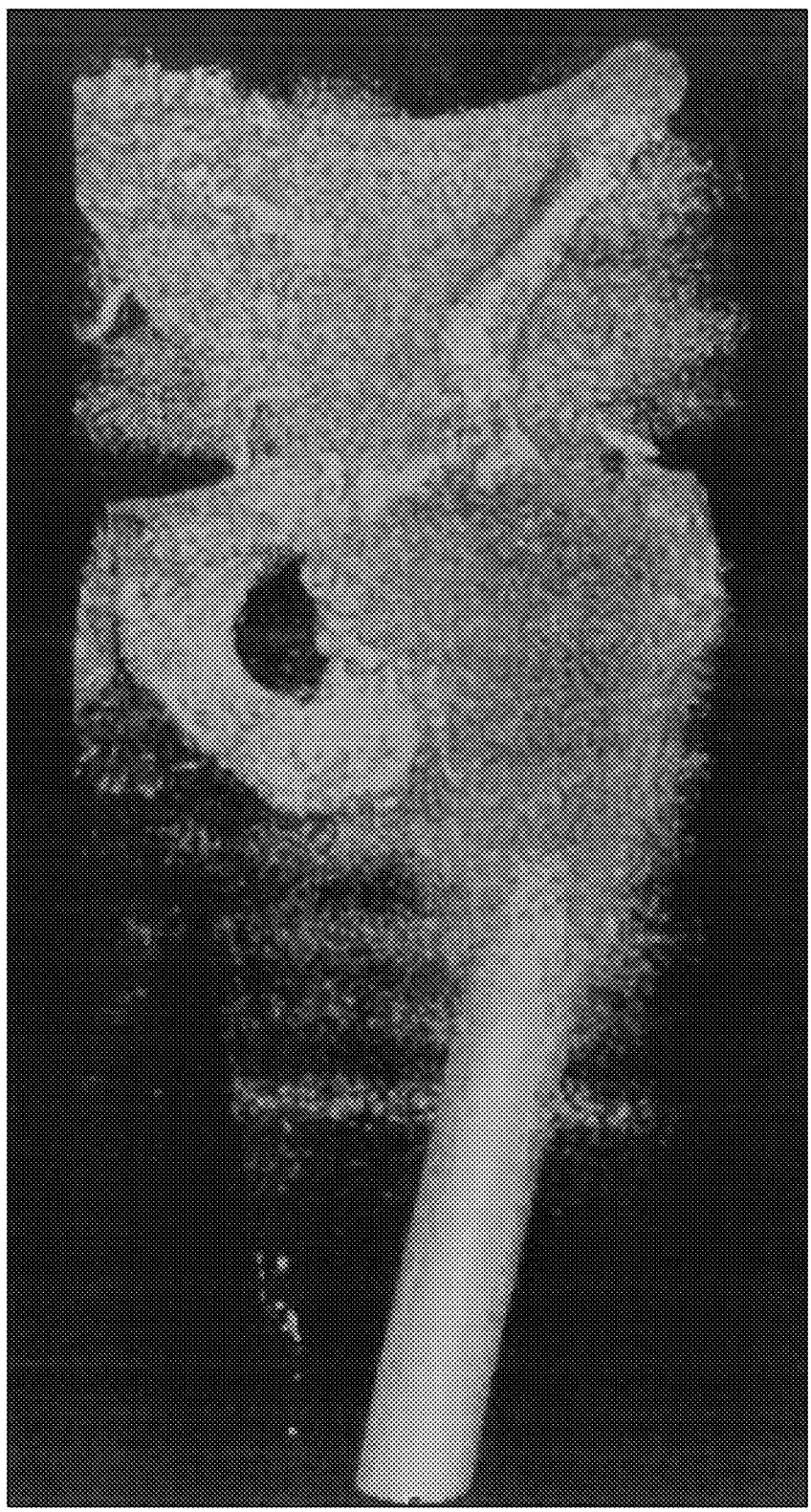
FIG. 16E is an example image automatically segmented at a third defined threshold, with bone segmented at a lower threshold value than in FIG. 16D (all bone included, also shown with increased noise/non-bone relative to FIGS. 16C and 16D) according to embodiments of the present invention.

FIGS. 16C-16E are example images from different thresholding levels defined in the Hounsfield unit scale of the CT image data. FIG. 16C corresponds to bone having been segmented at high value threshold (not all bone included). FIG. 16D corresponds to a lower threshold than the first, higher threshold (most bone included, but also some noise/non-bone). FIG. 16E is an image at a third segmentation threshold, further lower threshold (all bone included, substantial noise/non-bone).

Figure 17A:
FIGS. 17A-17J are images illustrating example automated registration processing according to embodiments of the present invention.

FIGS. 17A-17J illustrate example images of the registration process according to embodiments of the present invention. FIG. 17A is a joint view of two CT stacks showing the segmented hip implant before registration (same implant from paired CT stacks).

Figure 17B:

FIG. 17B shows that a part of the implant (metal rings of prosthesis cup) has been selected as a registration target, the same part selected in both stacks, shown in different colors.

Figure 17C:
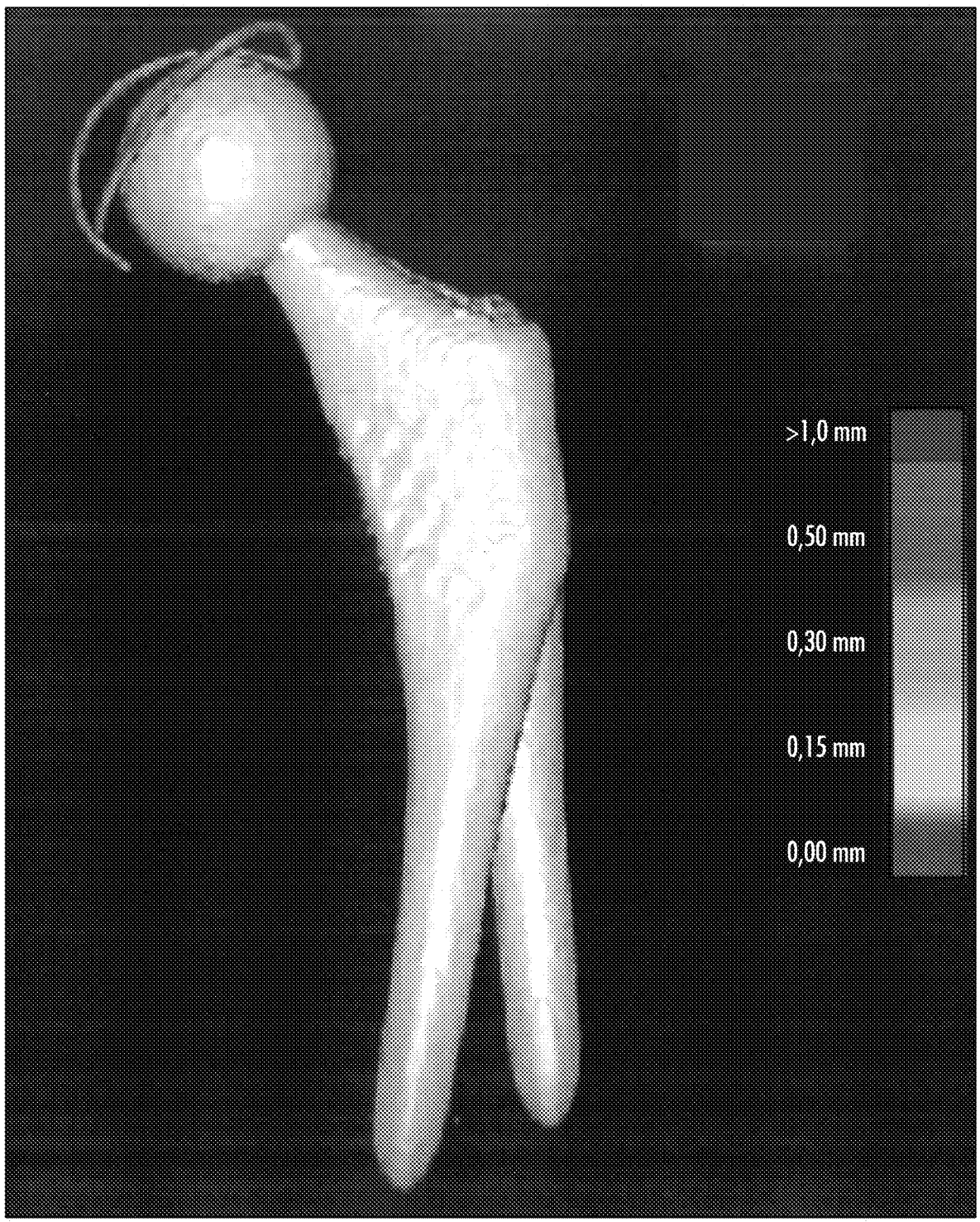

FIG. 17C shows the result of the registration: the matching of the metal rings is complete, color coding in appended scale and on the metal rings refers to spatial distance between object, i.e. registration accuracy, indicating accuracy is below 1.0 mm, primarily between 0.15 mm and 0.00 mm.

Figure 17D:
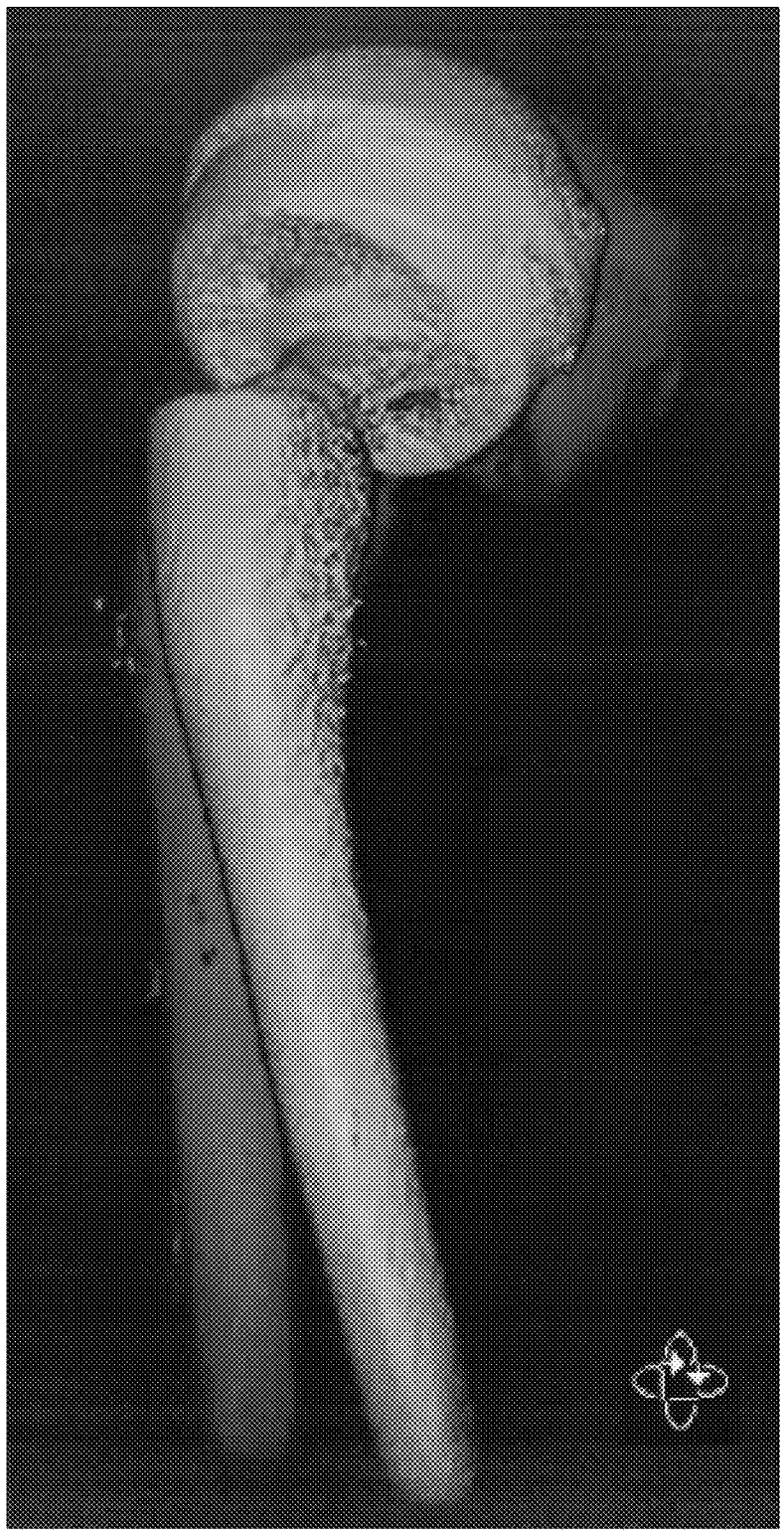

FIG. 17D is an image of an alternative registration target, the full hip implant is selected as registration target.

Figure 17E:
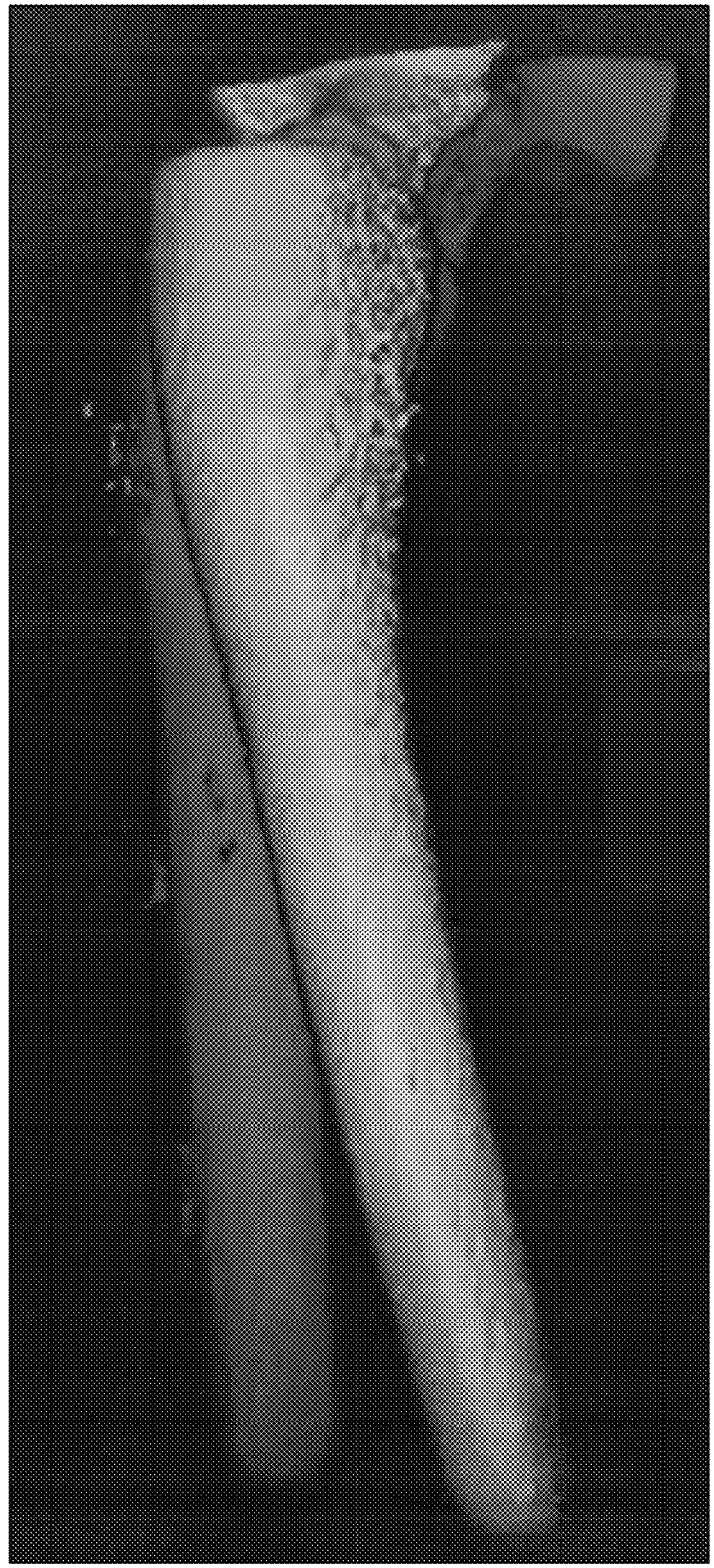

FIG. 17E is an image of another alternative registration target, a clip box can be used to select only stem part of hip implant.

Figure 17F:
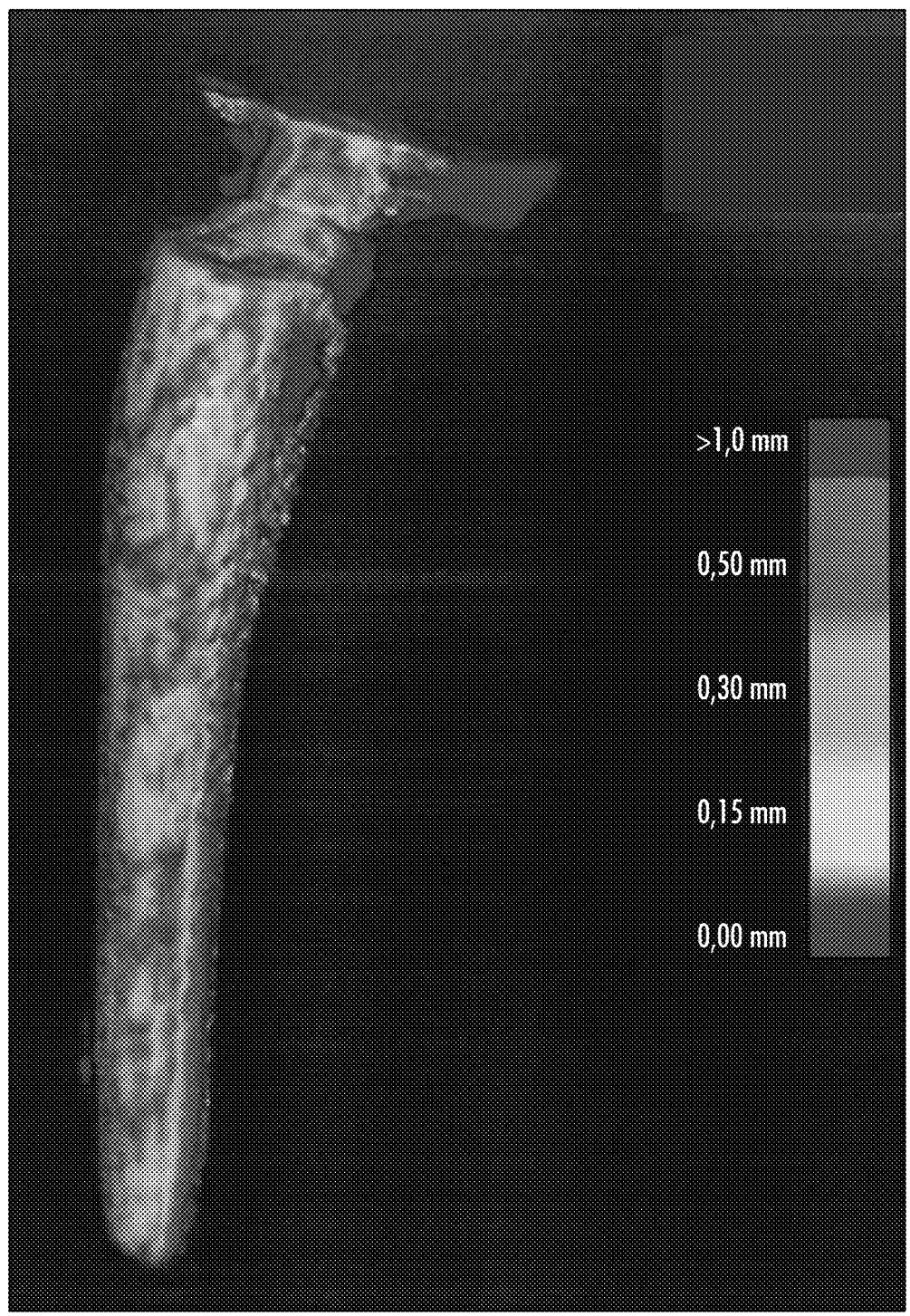

FIG. 17F is an image of a registered result for the target in FIG. 17E: the matching of the stem part is complete, color coded accuracy with color coding in appended scale and stem shown primarily below 1.0 mm and mostly in the 0.00 mm-0.15 mm range.

Figure 17G:
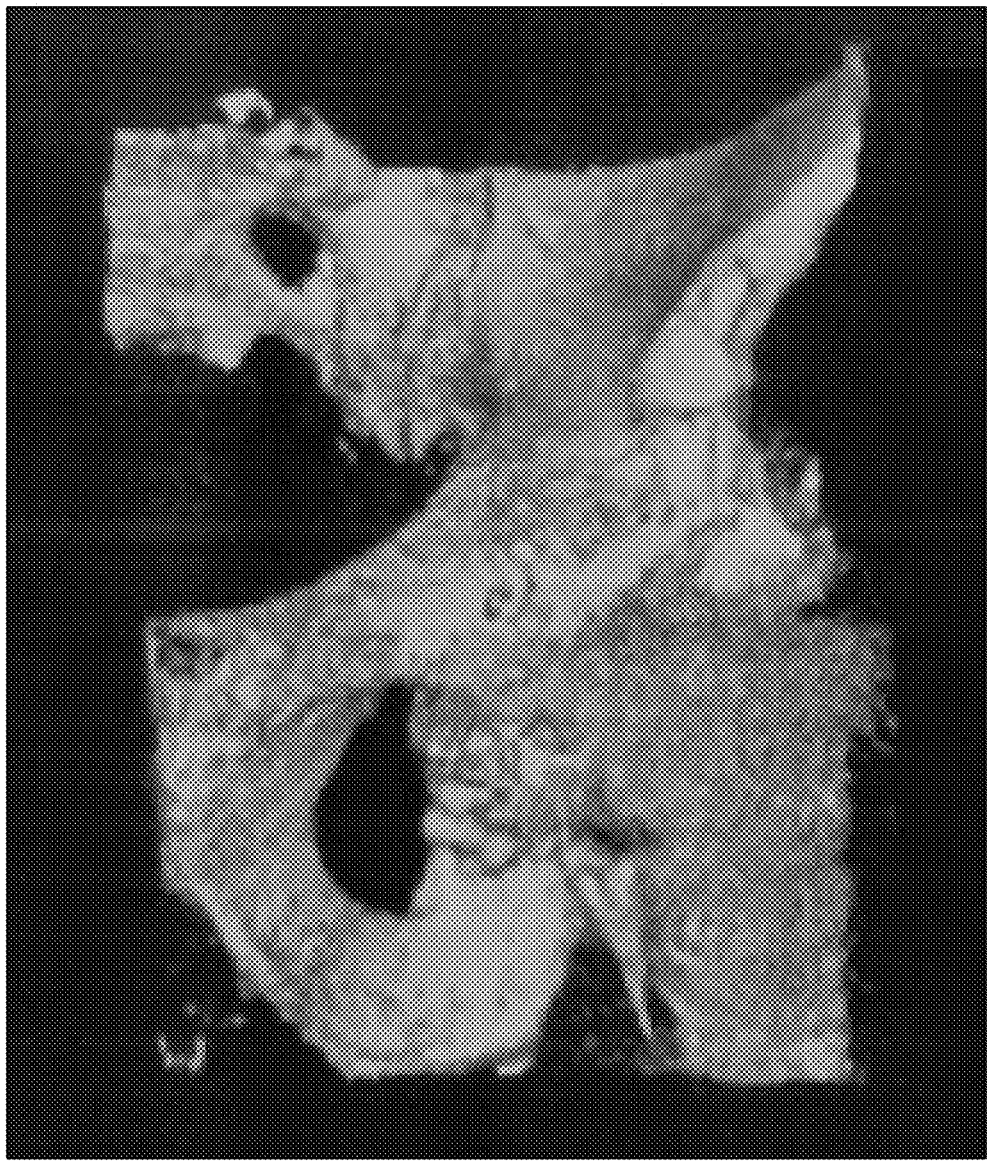

FIG. 17G is an image of another registration target, a bone target: a clip box has been used to select part of pelvis and femur as registration target, only one of the two stacks shown.

Figure 17H:
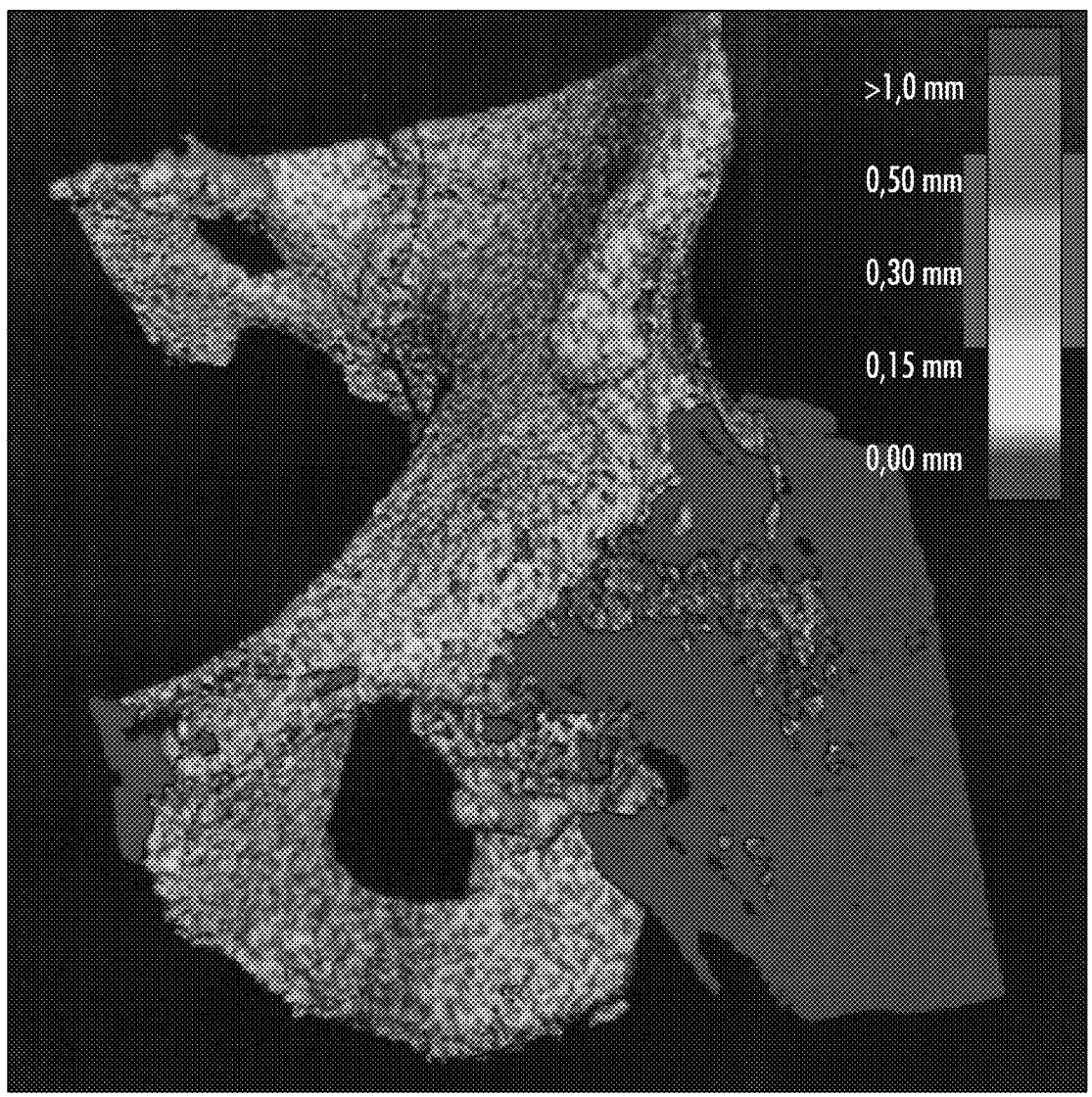

FIG. 17H is an image of the registration result of the bone target in FIG. 17G after also removing the femur from the registration target: the registration is complete, color coded accuracy with color coding in appended scale and stem primarily less than 1.0 mm, mostly between 0.00 mm and 0.15 mm (femur moves between the two stacks and should not match).

Figure 17I:
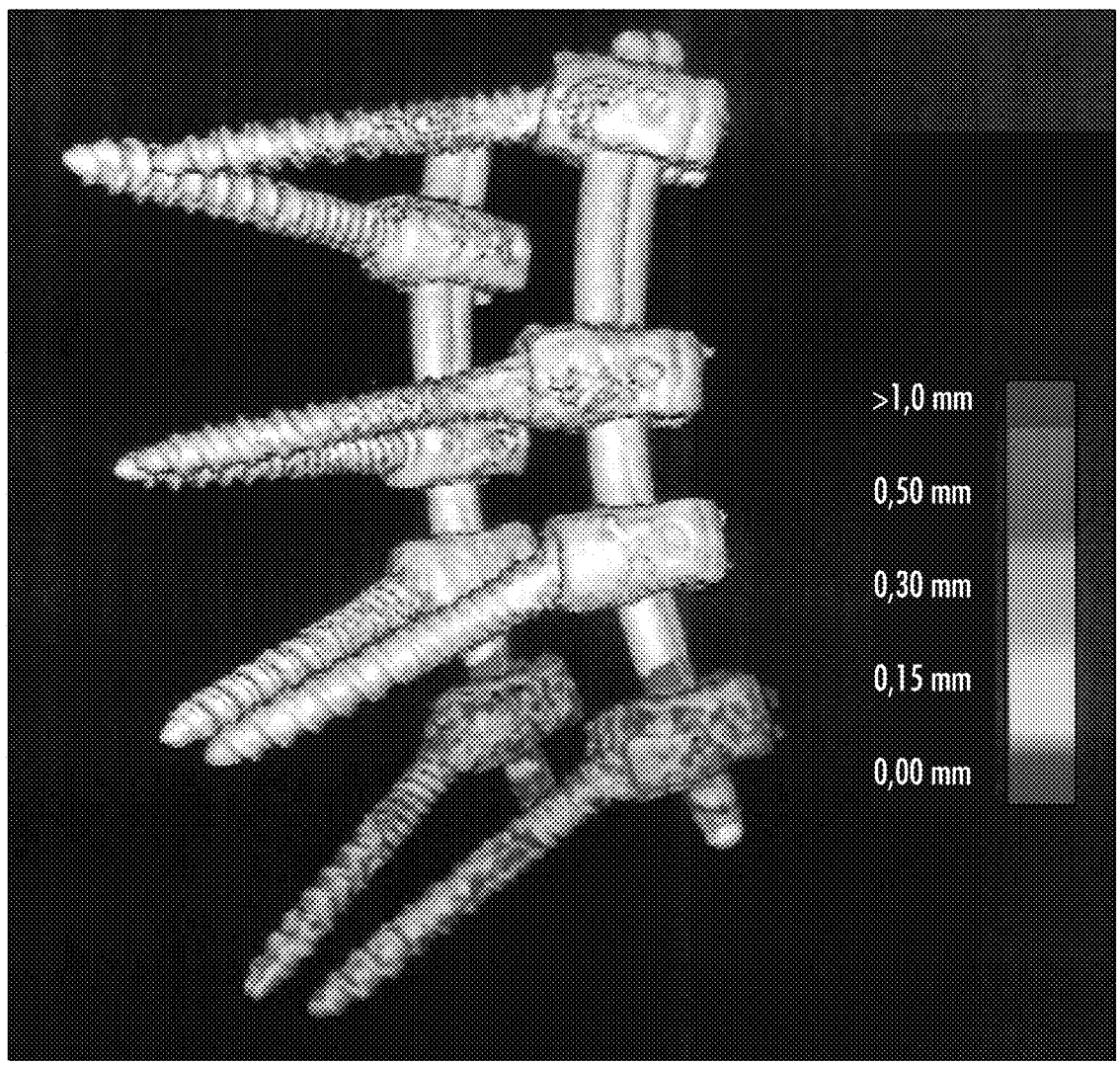

FIG. 17I is an image of another registration target, a spine implant: the image show the resulting registration for only the lower pair of pedicle screws in larger spine implant, color coded accuracy with color coding in appended scale and stem primarily less than 1.0 mm, mostly between 0.00 mm and 0.5 mm.

Figure 17J:
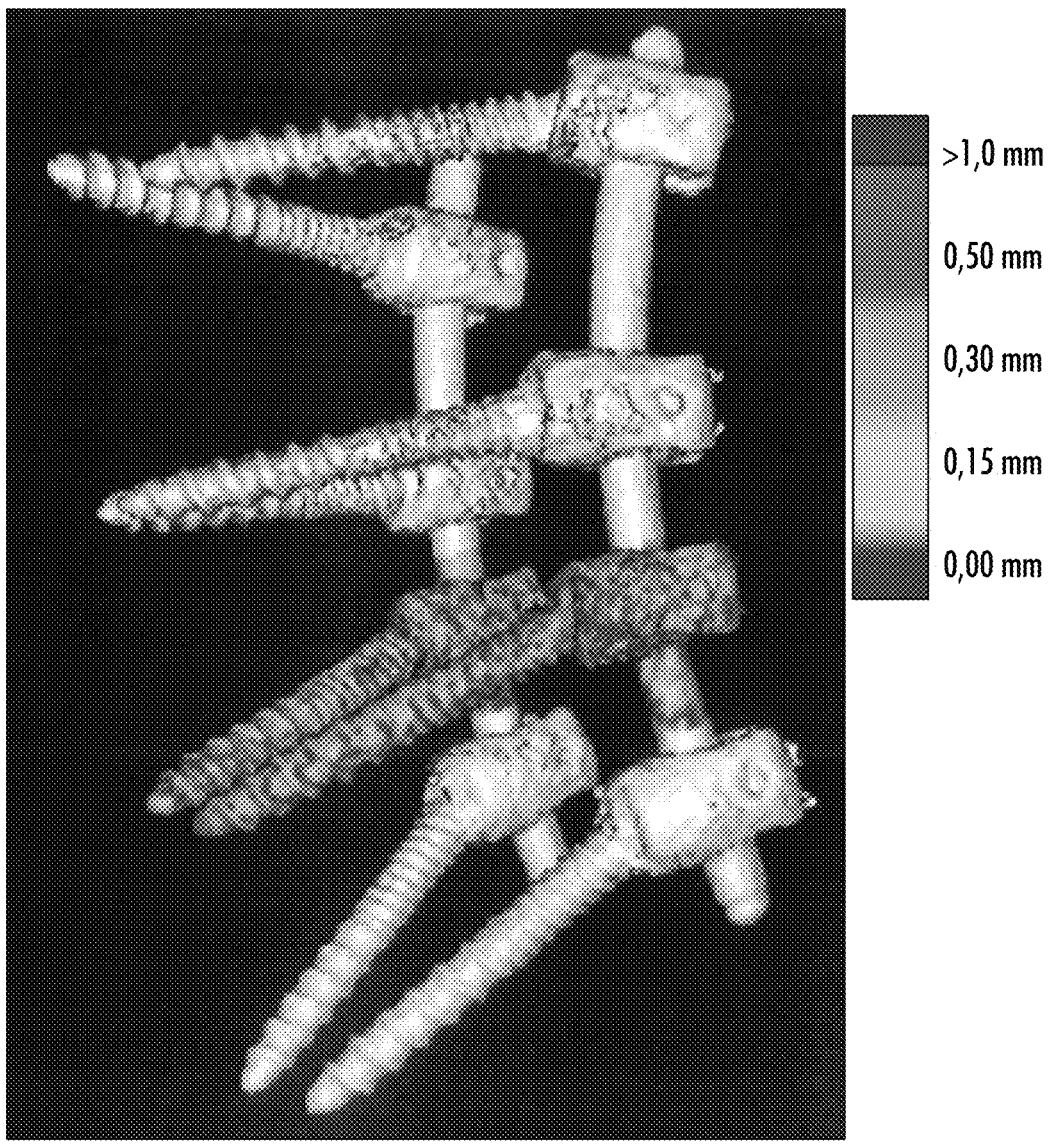

FIG. 17J is an image of another registration target of the spine implant: registration carried out for only the second lowest pair of pedicle screws in larger spine implant, color coded accuracy with color coding in appended scale and stem primarily less than 1.0 mm, mostly between 0.00 mm and 0.5 mm.

Figure 18:
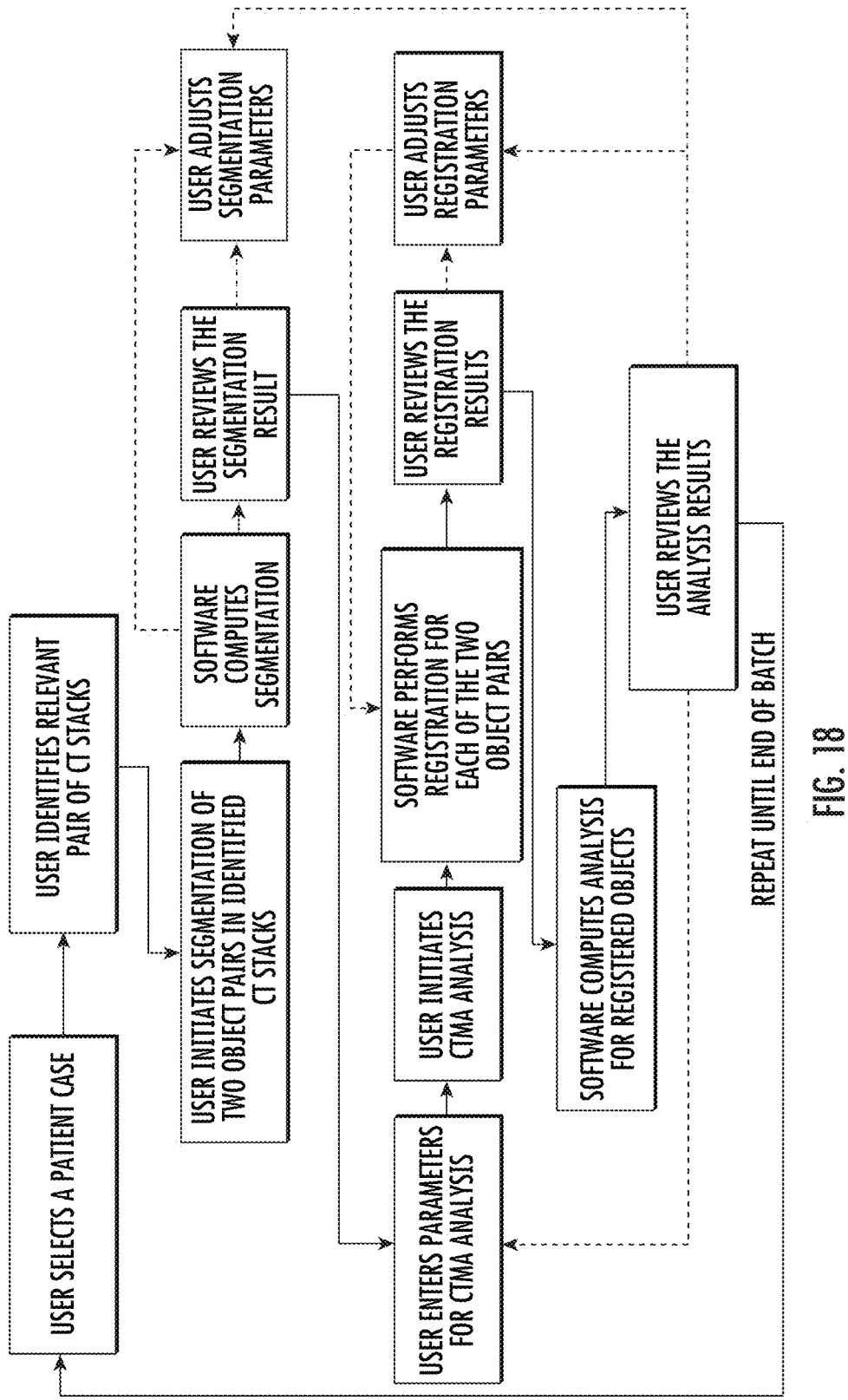
FIG. 18 is a flow chart of an overview of a prior art manual CTMA batch analysis method.

FIG. 18 illustrates an example overview of a prior art manual CTMA batch analysis system. Note the number of required user inputs and that each CT stack comparison is done manually from scratch.

Figure 19:
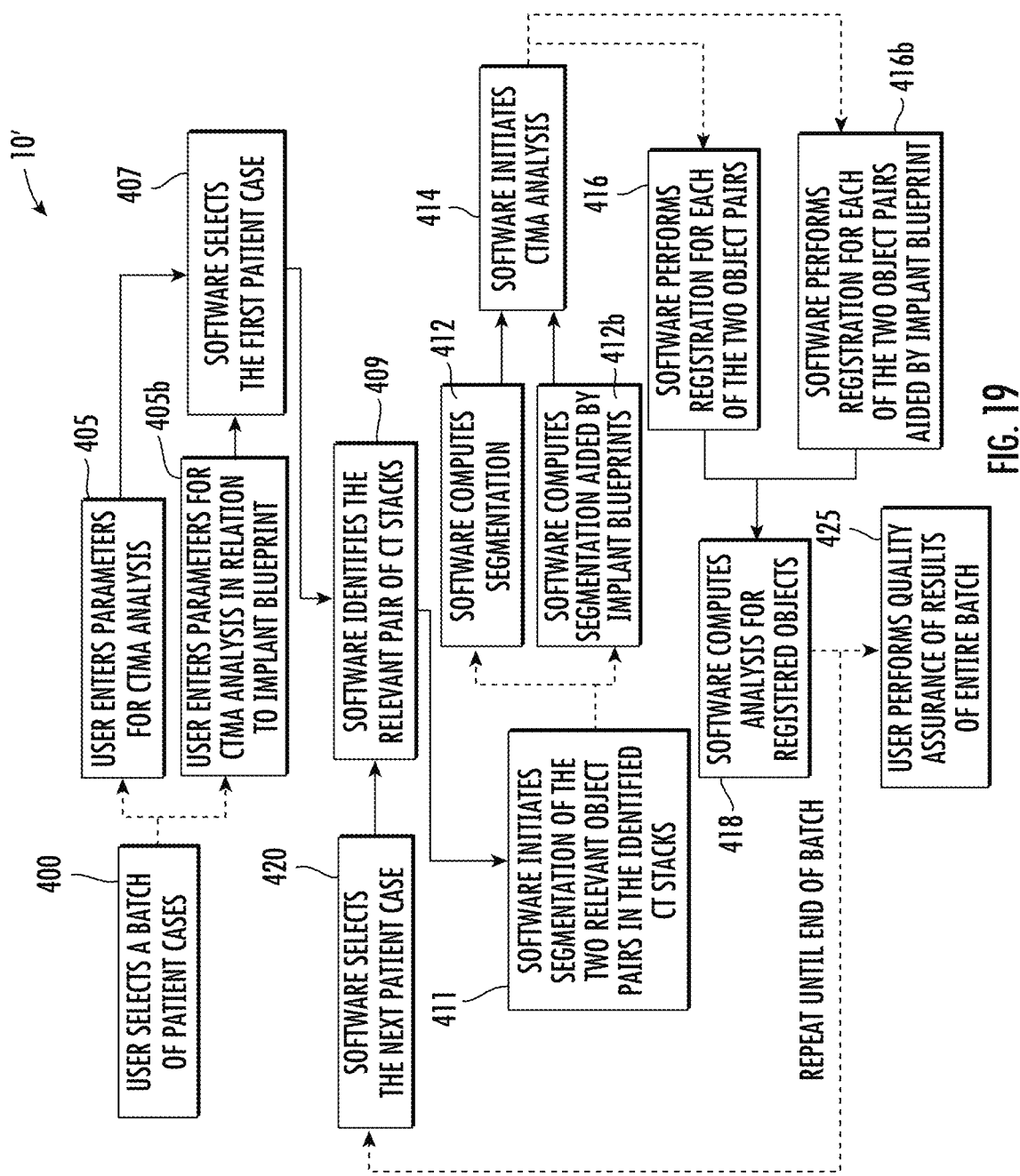
FIG. 19 is a flow chart of an automated batch analysis method according to embodiments of the present invention.

FIG. 19 is an overview of another embodiment of an example implant analysis system 10' which can be configured to evaluate batches of different patient image stacks. This embodiment operates in a batch mode of running CTMA comparisons across an entire cohort. The analysis system 10' can be configured to allow for a semi-automated setting where the user is only required to specify at one input the analysis to be made and the parameter settings to be used across the entire cohort.

As shown, the system 10' can be configured to import or allow a user to select a batch of different patient cases for evaluation (block 400).

This embodiment may be particularly suitable for research studies using CTMA across a patient cohort, typically to evaluate the performance of a specific implant type or drug effect on implant performance. CTMA can be used to make one to four comparisons within a patient (thus, across two to five time points), and repeat this for different patients within a study, such as 10 to 50 patients within a research study. Larger cohorts and more comparisons are also possible.

Within a study, the analysis setup will typically be very standardized, such as comparison target, implant type and scanner parameters. This contrasts with the scenarios targeted by patient-specific analysis discussed above where the setup of the individual comparison is time-consuming handling and the automated analysis systems 10 addresses this problem.

For batch analysis, it can be important that parameter settings of the analysis are identical across all comparisons. Unfortunately, making these settings manually as was done in the past is a time-consuming process which also increases the risk for random errors.

Embodiments of the invention provide an automated batch analysis system 10' that is configured to allow quality control to make sure the automated measurements are done correctly, since the data sets are often noisy, and it can be important that substantial errors in the analyses be identified and corrected.

As also shown in FIG. 19, the system 10' can be configured to select or allow a user to enter parameters for CTMA analysis (block 405). These entries can be in relation to an implant blueprint (block 405*b*). Again, although described as used with CT images for CTMA analysis, other depiction equipment may be used in lieu of CT images.

The parameters selected or used in relation to implant blueprint can include implant blueprint data corresponding to a physical shape and dimensions and implant type of a target implant for review, optionally identifiable via product number, manufacturer, part number, product name in a list of options and/or can be provided via a GUI of visualizations of different implants 35 for selection to define targets for analysis in the image stacks.

The system 10' can select the first patient case for analysis (block 407), which can be in a study ID order, random order, by date, alphabetic order by last name or other order. Alternatively, a user can select which case is the first patient case for analysis or which order is preferred (block 407). The system identifies the relevant pair of CT stacks from the first patient case (block 409).

The system identifies the relevant pair of CT stacks from the first patient case (block 409).

The system 10' initiates segmentation of the two relevant object pairs in the identified pair of CT stacks (block 411).

The system 10' computes segmentation (block 412). The system can optionally compute segmentation aided by data of the implant blueprint (block 412*b*).

The system 10' can initiate CTMA analysis (block 414). The system can perform registration for each of the two object pairs (block 416).

The system 10' can perform registration for each of the two object pairs aided by data from the implant blueprint (block 416*b*).

The system 10' can compute the movement analysis for the registered objects (block 418).

The system 10' can select or otherwise move to the next patient case for analysis (block 420).

The steps 409-418 can be repeated until the end of the batch is reached. The system 10' can be configured to allow a user to perform quality assurance of the results of the entire batch (block 425).

Figure 20:
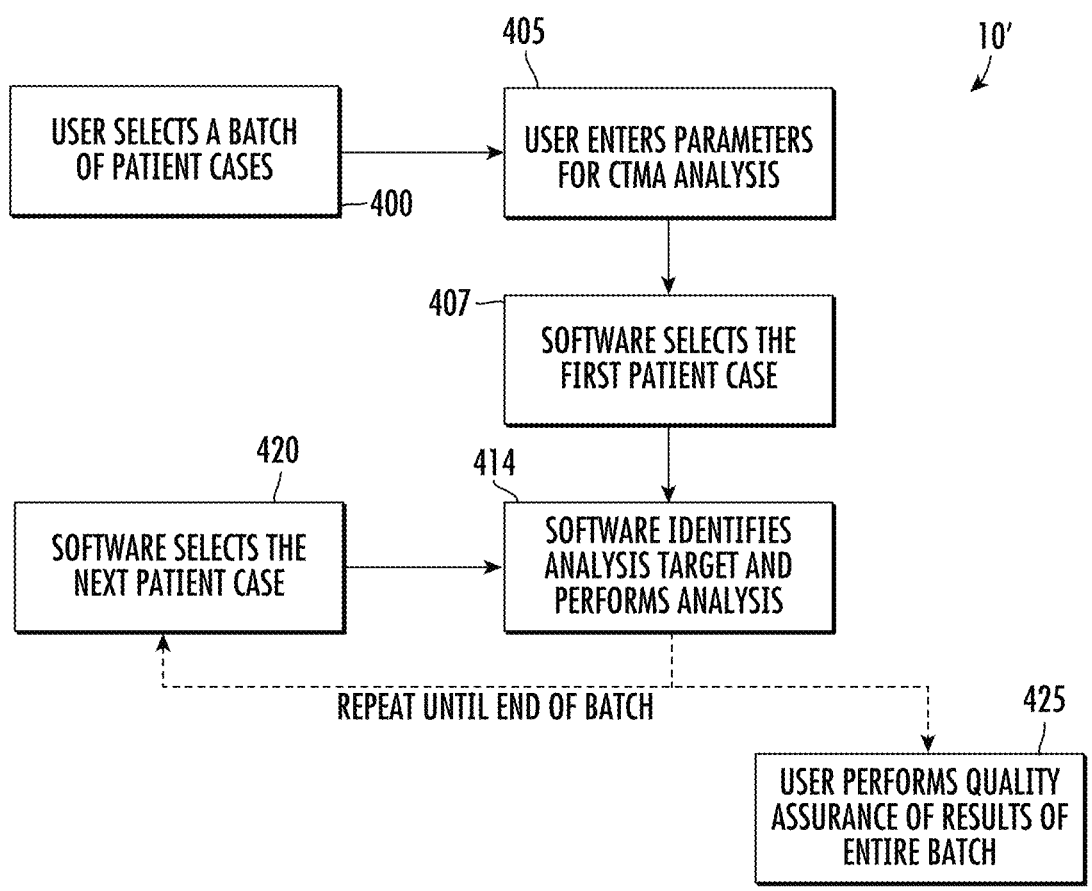
FIG. 20 is a flow chart of an automated batch analysis method that can include cohort propagation according to embodiments of the present invention.

FIG. 20 is an example of a batch analysis system 10' with a cohort propagation aspect according to embodiments of the present invention. Similar to FIG. 19, the system 10' can be configured to import or allow a user to select a batch of different patient cases for evaluation (block 400). The system 10' can be configured to select or allow a user to enter parameters for MA analysis (block 405). The system 10' can select the first patient case for analysis (block 407), which can be in a random order, by date, alphabetic order by last name or other order. Alternatively, a user can select which case is the first patient case for analysis or which order is preferred. The system 10' identifies the analysis target and performs the movement analysis (block 414). The system 10' selects the next patient case (block 420) and repeats the analysis (block 414) until the end of the batch. The system 10' can be configured to allow a user to perform quality assurance of the results of the entire batch (block 425).

The batch analysis system 10' can be configured to automatically propagate settings from one data set to the full cohort. The batch analysis setup can allow a user or the system to specify, provide or obtain the following information: the object to study and the reference object (one of which is the implant), how the coordinate system relates to the reference object, segmentation parameters such as value thresholds, and what measurements that are to be reported (rotation and location of which points of the object of study). A user can make these specifications for a first data set and then the analysis system 10' can propagate these settings to all other data sets in the cohort.

A technical challenge is to automatically find the two objects identified in the first data set in the subsequent data sets. The batch analysis system 10' can address this challenge through registration techniques. For example, for each subsequent data set, a preferred process is to first identify the implant (as this is typically very similar between data sets) and as a second step identify the second object using the implant position as guidance. The implant identification can employ the same registration technique across patients that CTMA uses for registering the implant between time points within a patient case. This can be carried out similar to the automatic identification of target objects discussed above for the patient-specific implant analysis system 10, but with a first data set defining a batch analysis template instead of a generic template.

In most cases, the propagation corresponds to re-applying segmentation, registration, measurement etc as defined for the first patient. But sometimes it could require a different processing step. For instance, an object segmentation of the first patient may be initialized by the user clicking a seed point, whereas the corresponding object segmentation in the rest of the batch is initialized based on registering the shape of the segmented object of the first patient with the object to segment, similar to how the blueprint is used in FIG. 28.

Another type of difference in propagating from first patient to others is that the threshold value for segmentation may be set manually for the first patient, and automatically for subsequent patients, such that the shape and size of the object matches the first patient segmentation, e.g., automatically repeating the segmenting step using different tuning parameters before the registration to thereby provide more accurate segmentation of the first and second objects.

The batch analysis system 10' can provide greater efficiency and precision in performing this type of implant movement analysis studies over conventional systems and methods.

Figure 21:
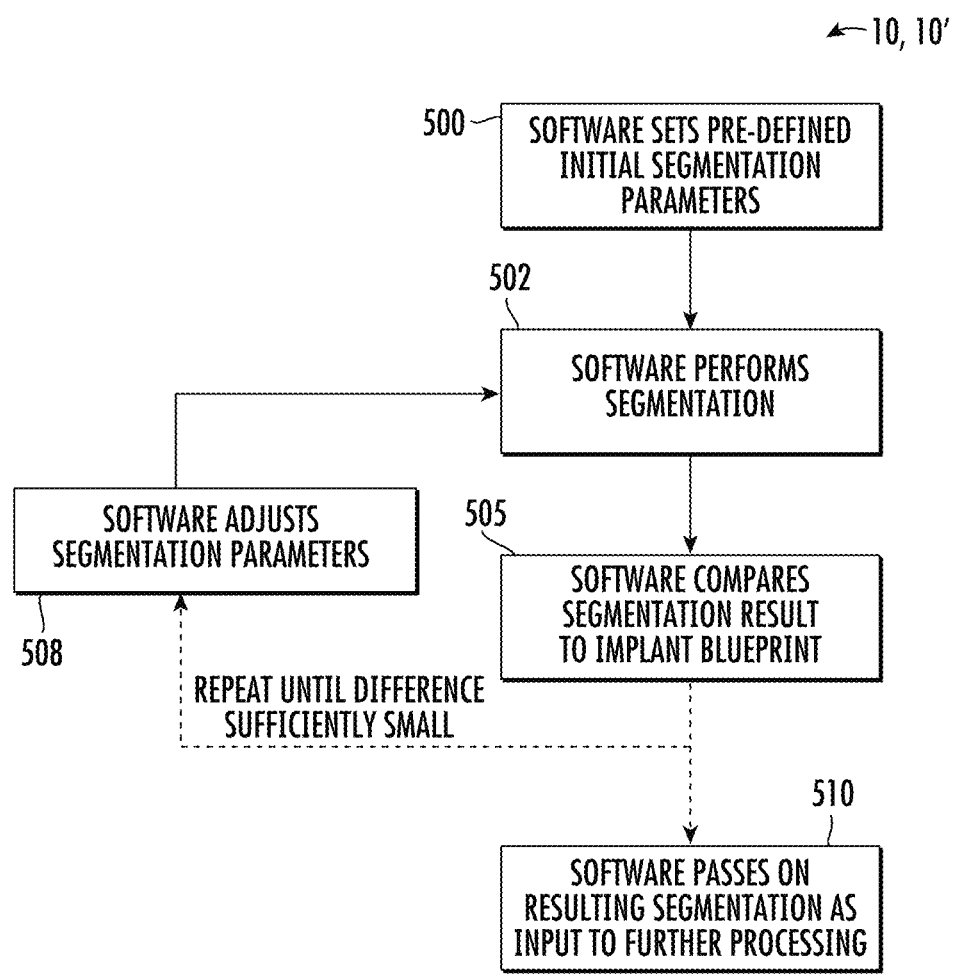
FIG. 21 is a flow chart of a segmentation process that uses an implant blueprint according to embodiments of the present invention.

FIG. 21 illustrates an example of actions for segmentation using implant blueprint data for image (implant) analysis systems 10, 10' according to embodiments of the present invention. The digital implant blueprint can be used to improve segmentation to inform the segmentation of the corresponding object in the CT stack. Generally stated, one way to utilize the implant blueprint is to automatically adjust the segmentation parameters, such as threshold levels, to achieve an as close as possible match between the entire device or a sub-portion of the device in the image blueprint and the segmented object.

Referring to FIG. 21, pre-defined, initial segmentation parameters can be set or selected (block 500). The system then performs segmentation (block 502). The system 10, 10' compares the segmentation result to the shape of the implant blueprint (block 505). If the shape or a boundary of the object does not correspond to the implant blueprint, the system 10, 10' can adjust segmentation parameters (block 508), then repeat the segmentation (block 502). The segmentation is complete when the shape of the implant blueprint is within the defined threshold. The resulting segmentation can be used as input to further processing (block 510).

Figure 34A:
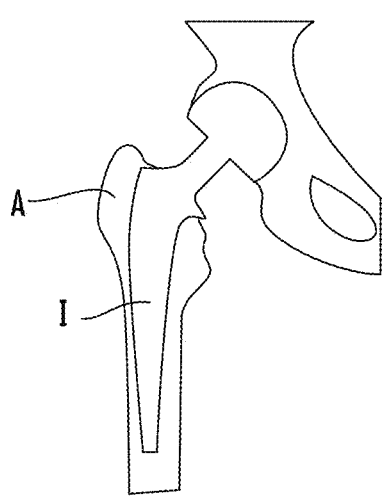
FIGS. 34A-34D are illustrations of an example segmented implant can be used as guidance for segmentation of a related anatomical object according to embodiments of the present invention.
Figure 34B:
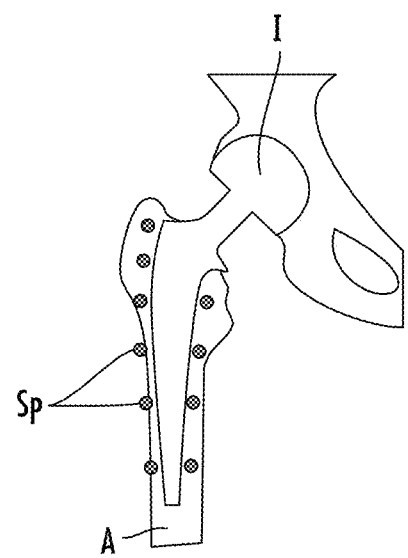
Figure 34C:
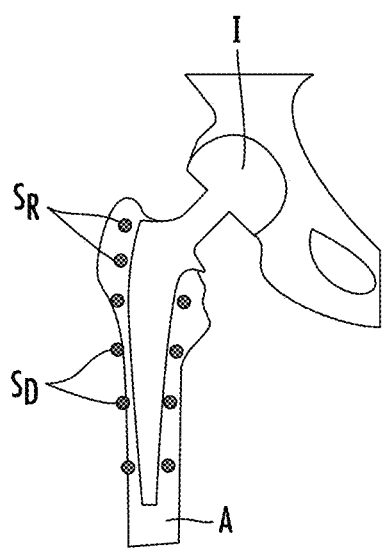
Figure 34D:
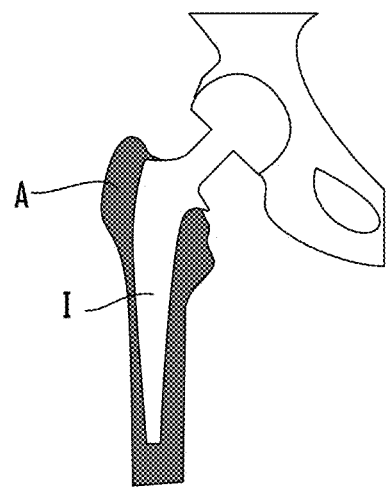

FIGS. 34A-34D illustrate an example of how a segmented implant I can be used as guidance for segmentation of a related anatomical object A. These illustrations are of an example hip implant in two-dimensions for ease of discussion but typical segmentations are in three-dimensions. FIG. 34A illustrates an image with a segmented hip implant I. FIG. 34B illustrates a plurality of seed points Sp for femur segmentation, as defined by their spatial relation to the implant I. FIG. 34C illustrates that some seed points Sp are retained $S_R$ while others are discarded or not used $S_D$, based on their Hounsfield value. FIG. 34D illustrates a resulting segmentation of the anatomical object (femur) based on the retained seed points $S_R$.

Figure 22:
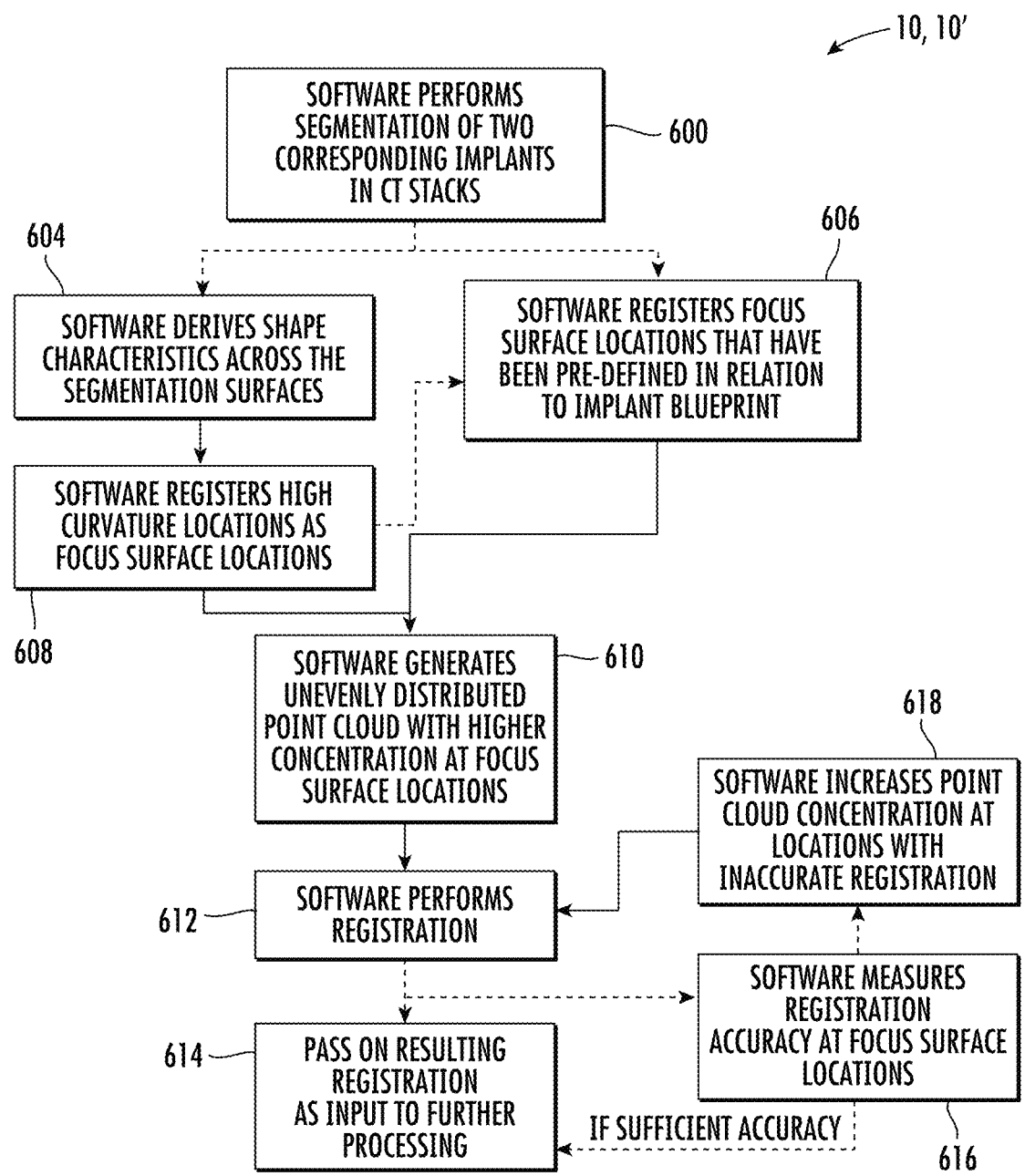
FIG. 22 is a flow chart of actions that can be carried out to improve and/or assess registration accuracy using surfaces of the implant blueprint according to embodiments of the present invention.

FIG. 22 illustrates an example of actions for registration using implant blueprint data for implant analysis systems 10, 10' according to embodiments of the present invention. A digital implant blueprint can be utilized to improve registration. For example, registration can be performed by a matching of point clouds, where the points are generated on the surface of the object. Precision can be improved by making sure that the point cloud is more densely populated at sharp points or edges of the object, such as the tip of the stem of a hip prosthesis. Another possibility to utilize the image blueprint is to define such "sweet spots" for the point cloud generation, to be applied across the entire cohort.

The term "ray casting" is well known to those of skill in the art and refers to electronically casting rays to sample volumetric data sets to solve a variety of problems in computer graphics and computational geometry. The term "point cloud" refers to a set of points distributed in a volumetric space to identify an object in that volumetric space, such as an implant or part of an implant and/or bone bounding a volumetric space. See, by way of example only, Dodin, P., Martel-Pelletier, J., Pelletier, J.-P., Abram, F. (2011) A fully automated human knee 3D MRI bone segmentation using the ray casting technique. Medical & Biological Engineering & Computing, December 2011, Volume 49, Issue 12, pp 1413-1424; and Kronman A., Joskowicz L., Sosna J. (2012) Anatomical Structures Segmentation by Spherical 3D Ray Casting and Gradient Domain Editing. In: Ayache N., Delingette H., Golland P., Mori K. (eds) Medical Image Computing and Computer-Assisted Intervention-MICCAI 2012. MICCAI 2012. Lecture Notes in Computer Science, vol 7511. Springer, Berlin, Heidelberg. The contents of these documents are hereby incorporated by reference as if recited in full herein.

Referring to FIG. 22, the analysis system 10, 10' performs segmentation of two corresponding implants in CT stacks (block 600). The system 10, 10' derives shape characteristics across the segmentation surfaces (block 604).

Alternatively or additionally, the system 10, 10' registers focus surface locations that have been pre-defined in relation to implant blueprint (block 606).

The system 10, 10' can generate unevenly distributed point cloud with higher concentration at focus surface locations (block 610).

The system 10, 10' can perform a registration (block 612).

The system 10, 10' can measure registration accuracy at focus surface locations (block 616). The system 10, 10' can increase point cloud concentration at locations with inaccurate registration (block 618).

If or when there is sufficient accuracy, the resulting registration can be provided as input to further processing (block 614).

Figure 23:
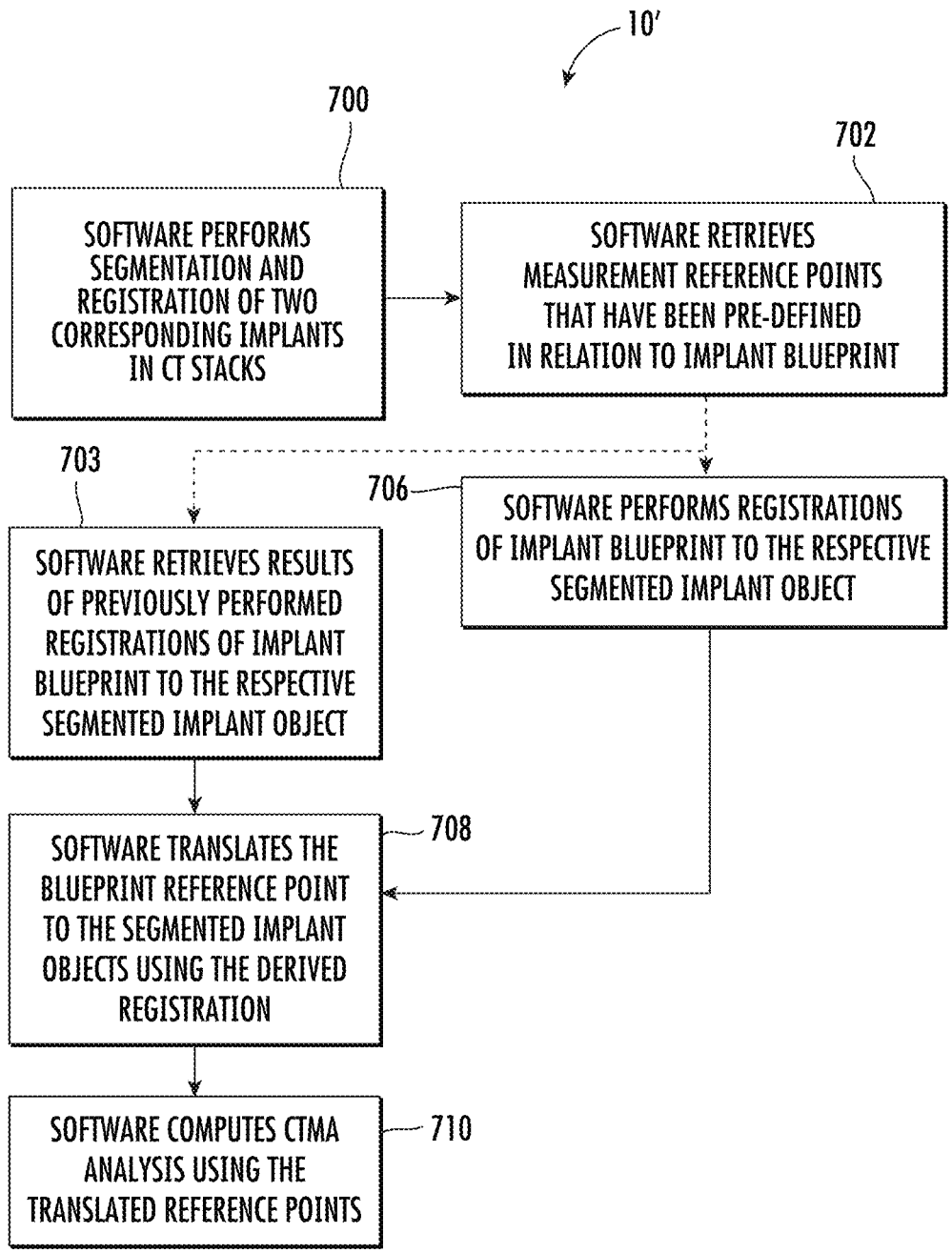
FIG. 23 is a flow chart of actions that can be carried out to improve and/or assess registration accuracy using the implant blueprint for measurement according to embodiments of the present invention.

FIG. 23 illustrates an example of actions for measurement using implant blueprint data for implant analysis systems 10, 10' according to embodiments of the present invention. The digital implant blueprint can be utilized to improve measurements. In order to get a high-precision definition of the points on an implant where measurements are to be made, embodiments of the invention allow them to be identified or selected on the implant blueprint instead of on the implant as depicted in the CT stack. The point definition can then be electronically transferred to the image-domain implant through the registration process.

Referring to FIG. 23, the system 10, 10' can perform segmentation and registration of two corresponding implants in respective CT stacks (stack pairs) (block 700). The system 10, 10' can retrieve measurement reference points that have been pre-defined in relation to the implant blueprint (block 702).

The system can retrieve results of previously performed registrations of implant blueprint to the respective segmented implant object (block 703).

Alternatively or additionally, the software performs registrations of implant blueprint to the respective segmented implant object (block 706).

The system 10, 10' translates the blueprint reference points to the segmented implant objects using the registration (block 708). The system computes CTMA analysis using the translated reference points (block 710).

Figure 24:
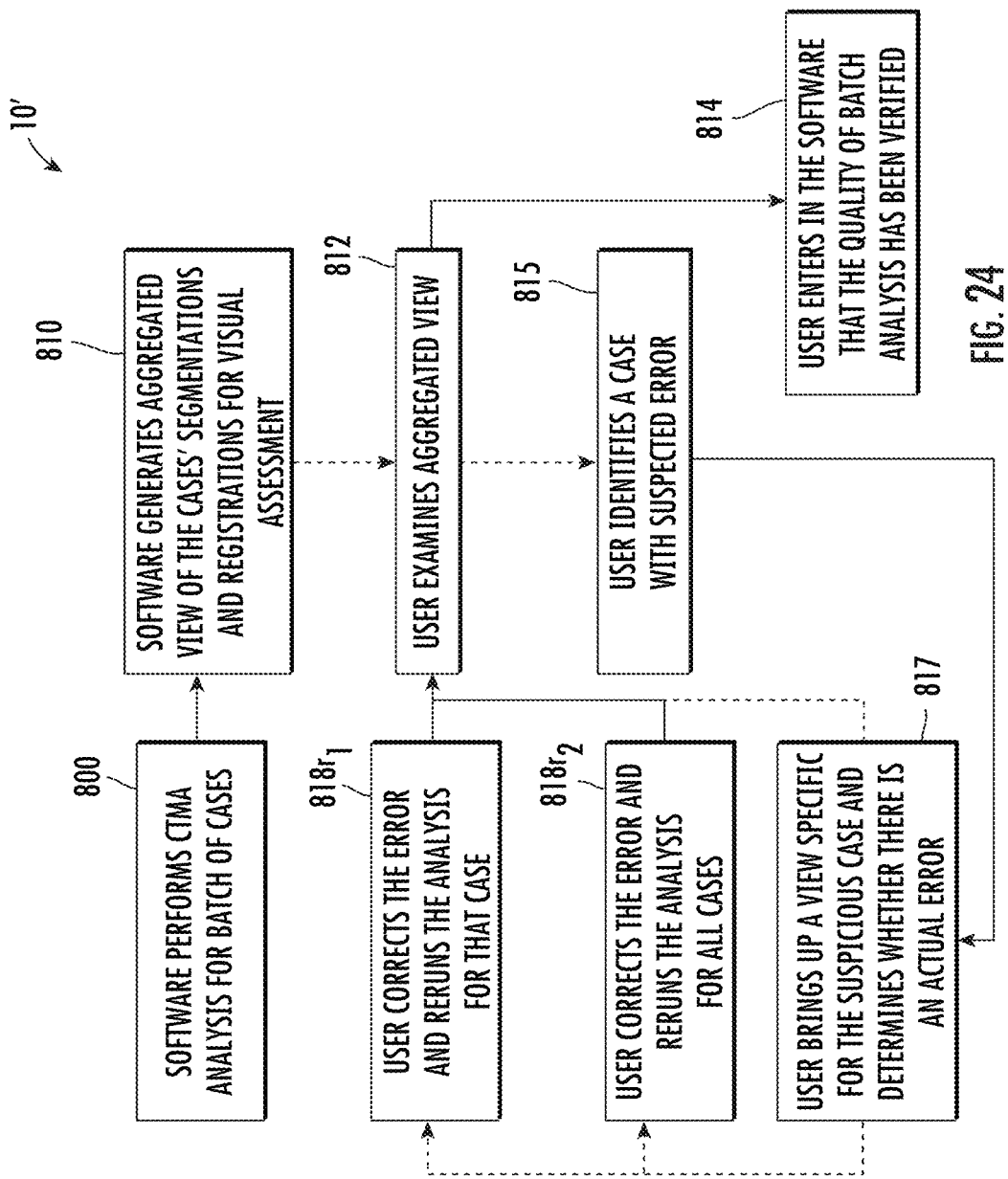
FIG. 24 is a flow chart of actions that can be carried out for performing batch quality assurance according to embodiments of the present invention.

FIG. 24 illustrates example quality assurance actions for batch implant analysis systems 10' according to embodiments of the present invention. The system 10' can be configured to facilitate quality assurance of the analysis of the entire batch. It can be time-consuming to review the quality of the registration for each comparison in the cohort. Embodiments of the invention can provide an aggregated view of all registrations. One component can be to visualize all objects of study, overlaid on each other with location relative to their respective reference object, such that overlapping regions are de-emphasized in order to accentuate outliers. The de-emphasis can be achieved by making transparency or translucency of a sub-region inversely proportional to the number of objects overlapping in that sub-region.

Another aggregated view can be to represent all the comparisons as items in a list, with text and/or thumbnail images, optionally sort them according to amount of movement. The list can be linked to the aggregated view described above, such that clicking in one of the views highlights the corresponding parts of the other view.

FIGS. 33A-33C are examples of a display 20 with a user interface 30 with an aggregated view V that represents corresponding objects (implants and/or implants and relevant anatomy) from the different patient images and thumbnail images 120 with the implant I for each stack, where each row of thumbnail images 120r is for a respective separate patient at different time points, shown as two different time points. This illustration is shown with respect to a very small (atypical) batch of different patients for discussion purposes. FIG. 33B illustrates that a specific patient can be selected by a user using the user interface 30. A border 121 can be used to visually correlate the selected patient image to the corresponding patient's thumbnail images. Selection of an image or images of a patient can be made in both the aggregated view V and the thumbnail views 120 of a particular patient. For example, as shown in FIG. 33B, a user can select either the thumbnail view(s) of a patient which can prompt the display to visually emphasize the corresponding implant in the aggregate view V, shown as by providing a perimeter border in color in the aggregated view V or a user can select an object in the aggregated view V to prompt the system to visually correlate the corresponding patient thumbnail views in the thumbnails 120, optionally by generating a color border in the thumbnail view. FIG. 33C illustrates that for a selected patient image in the aggregated view V, other views can be shown such as the registered implant of the selected patient provided in a color-coded view 175 representing registration quality (such as discussed above with respect to FIGS. 17A-J).

Referring to FIG. 24, the system 10' performs CTMA analysis for the batch of cases (block 800). The system 10' generates aggregated view of the cases' segmentations and registrations for visual assessment (block 810). The system 10' is configured to display the aggregated views and allow a user to examine the aggregated view (block 812). The system 10' is configured to allow a user to flag a case if the user identifies a case with suspected error (block 815).

If errors are not identified, the system 10' can be configured to allow a user to enter a verification that the quality of batch analysis has been verified as valid and approved (block 814).

If the user identifies a suspected error, the system 10' can allow a user to select a view specific for the suspicious case, optionally in an enlarged format relative to the aggregated view, and present that view to the display 20 to allow the user to determine whether there is an actual error (block 817).

Figure 25:
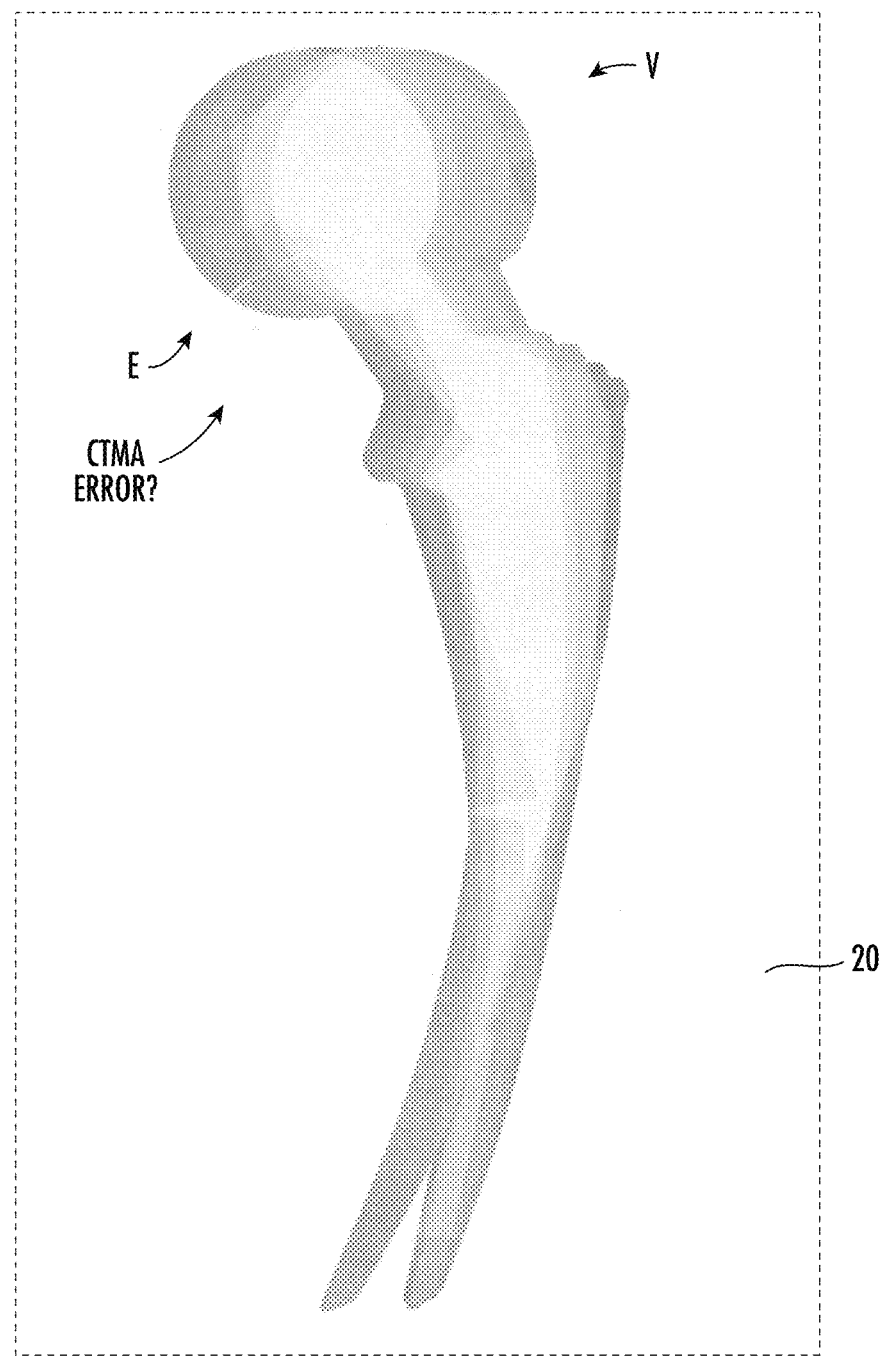
FIG. 25 is an image of an example view of a batch analysis system to investigate suspected CTMA processing errors which can be provided to a user for a quality assurance protocol according to embodiments of the present invention.

As shown in FIG. 25, the aggregated view "V" comprises a plurality of different registered/segmented objects from patient implant images overlaid to visually accentuate outliers that may indicate an error E that can be electronically selected or separate viewing by a user, such as by touch screen, mouse or button input.

The system 10' can allow the user to correct an identified error and the system 10' can then re-run the movement analysis for that patient case (block $818r_1$) and/or for rerun of all cases (block $818r_2$).

Figure 26:
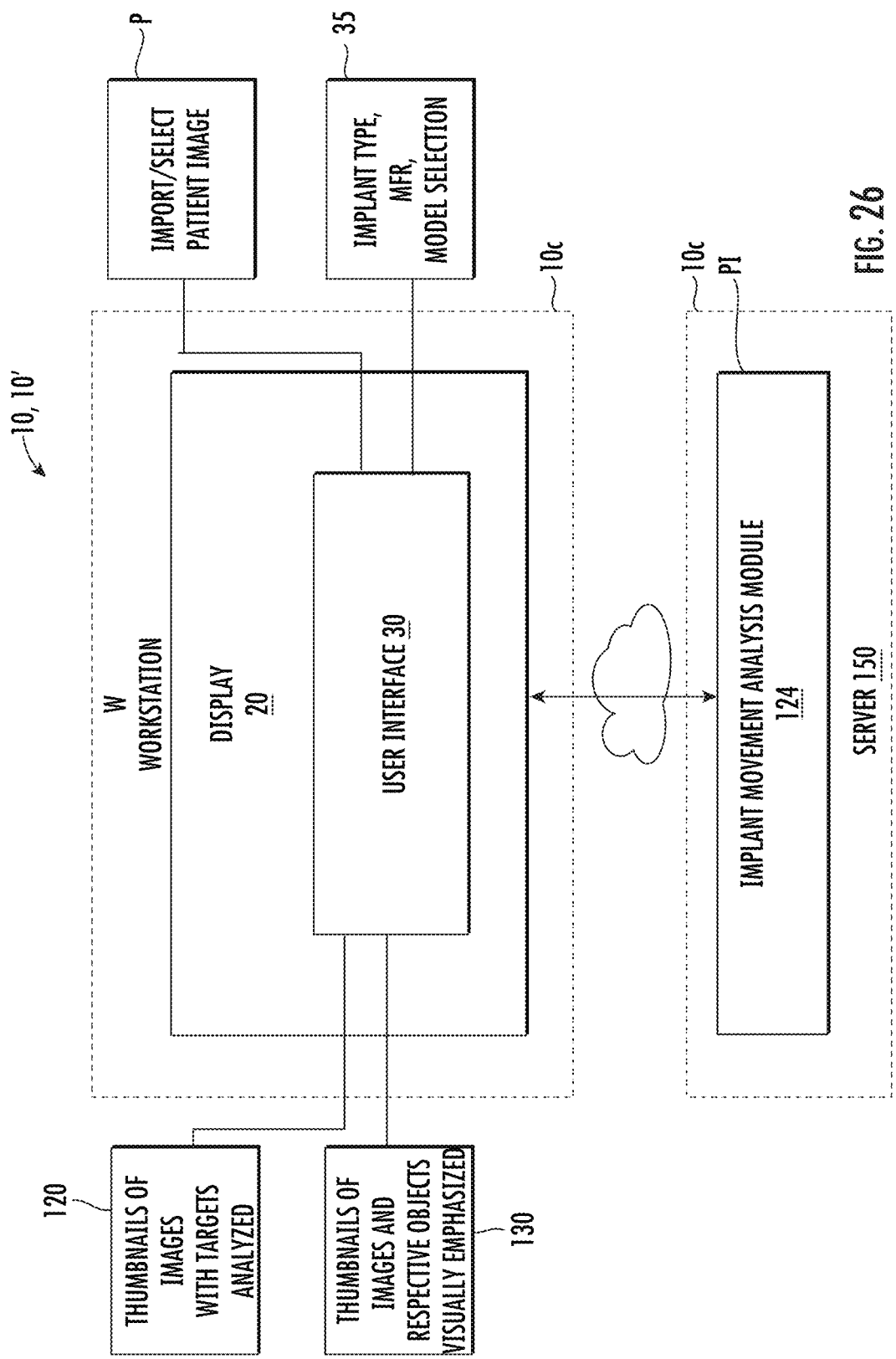
FIG. 26 is a schematic illustration of a system configured for automated image analysis according to embodiments of the present invention.

FIG. 26 is a schematic illustration of an automated image analysis system 10, 10' with a display 20, a user interface 30 and an image processing circuit 10c. The image processing circuit 10c can include one or more processors and can be partially or totally held in a workstation (W) with the display 20 or may be partially or totally remote from a workstation, such as held in one or more servers 150 and accessible via a network (i.e., the Internet) via firewalls. The one or more servers 150 can be integrated into a single server or may be distributed into one or more servers or other circuits or databases at a single physical site or at spatially separate locations. Similarly, the implant movement analysis module 124 can be held by the one or more servers 150 and can be distributed into multiple processors or databases or integrated into one or held entirely at a workstation "W".

The image processing circuit 10c can be configured to provide thumbnails 120 of visualizations of images with targets analyzed across stack pairs to the display 20, optionally connected to the user interface 30, which may be a graphic user interface.

The image processing circuit 10c can be configured to provide thumbnails 130 of images with respective objects from image stack pairs visually emphasized (highlighted). The image processing circuit 10c can be configured to import or select patient images P or batches of images P for analysis.

The systems 10, 10' can be configured to provide defined implant blueprint data 35 (optionally with type, manufacturer, product name, model or the like or a virtual replica image of the implant) that can be selected by a user for analysis in patient images or may be identified by metadata or other patient file data.

The server 150 may be embodied as a standalone server or may be contained as part of other computing infrastructures. The server 150 may be embodied as one or more enterprise, application, personal, pervasive and/or embedded computer systems that may be standalone or interconnected by a public and/or private, real and/or virtual, wired and/or wireless network including the Internet, and may include various types of tangible, non-transitory computer-readable media. The server 150 may also communicate with the network via wired or wireless connections, and may include various types of tangible, non-transitory computer-readable media.

The server 150 can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers.

Users can communicate with the server 150 via a computer network, such as one or more of local area networks (LAN), wide area networks (WAN) and can include a private intranet and/or the public Internet (also known as the World Wide Web or "the web" or "the Internet." The server 150 can include and/or be in communication with the implant movement analysis module 124 using appropriate firewalls for HIPPA or other regulatory compliance.

Embodiments of the present invention may take the form of an entirely software embodiment or an embodiment combining software and hardware aspects, all generally referred to herein as a "circuit" or "module." Furthermore, the present invention may take the form of a computer program product on a (non-transient) computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. As noted above, the functionality of any or all of the program modules may also be implemented using discrete hardware components, one or more application specific integrated circuits (ASICs), or a programmed digital signal processor or microcontroller. The program code may execute entirely on one (e.g., a workstation) computer, partly on one computer, as a stand-alone software package, partly on the workstation's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 27:
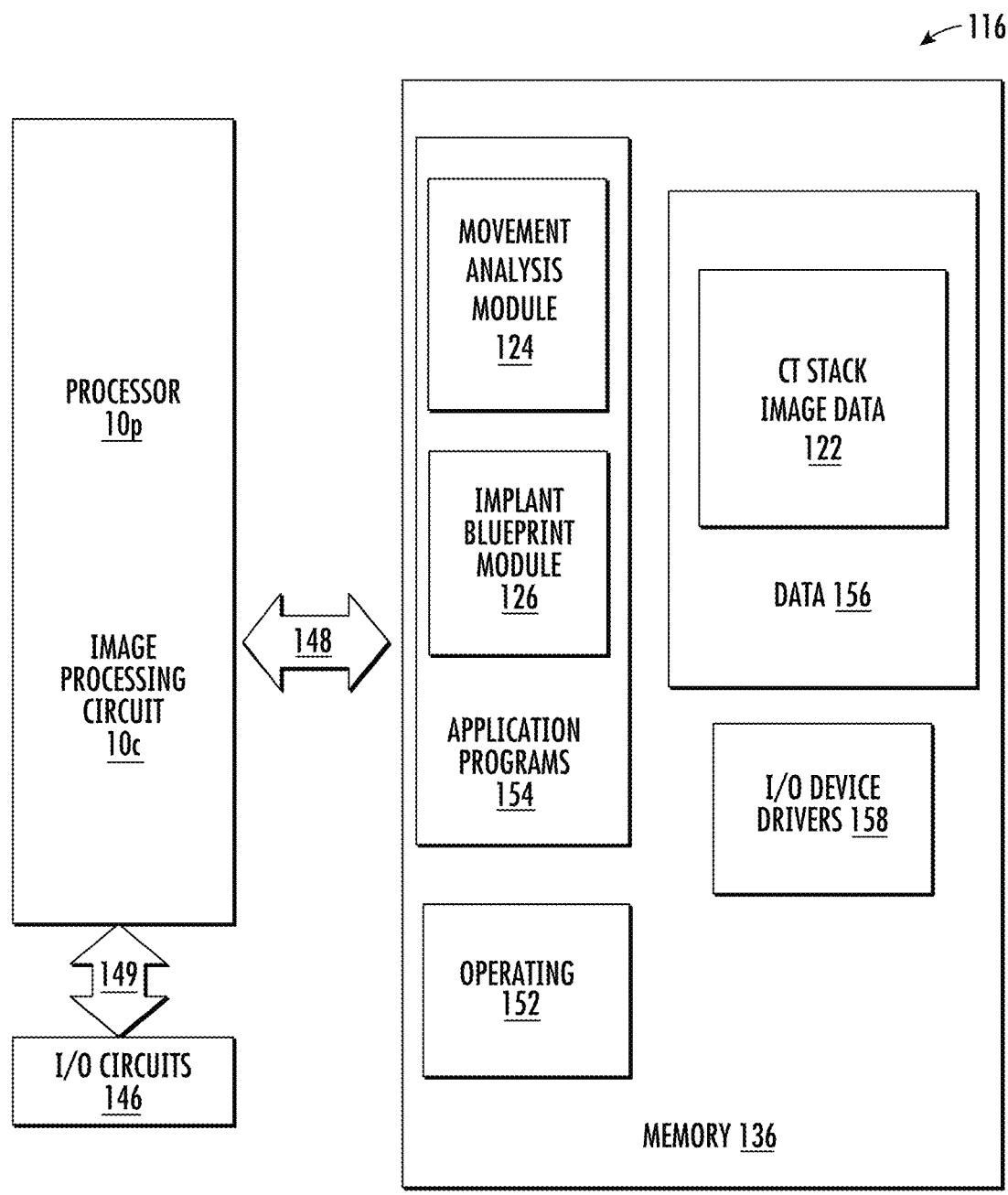
FIG. 27 is a schematic diagram of an example data processing system according to embodiments of the present invention.

As illustrated in FIG. 27, embodiments of the invention may be configured as a data processing system 116, which can include a (one or more) processors 10*p*, a memory 136 and input/output circuits 146. The one or more processors 10*p* can be part of the image processing circuit 10*c*. The data processing system may be incorporated in, for example, one or more of a personal computer, database, workstation W, server, router or the like. The system 116 can reside on one machine or be distributed over a plurality of machines. The processor 10*p* communicates with the memory 136 via an address/data bus 148 and communicates with the input/output circuits 146 via an address/data bus 149. The input/output circuits 146 can be used to transfer information between the memory (memory and/or storage media) 136 and another computer system or a network using, for example, an Internet protocol (IP) connection. These components may be conventional components such as those used in many conventional data processing systems, which may be configured to operate as described herein.

In particular, the processor 10*p* can be commercially available or custom microprocessor, microcontroller, digital signal processor or the like. The memory 136 may include any memory devices and/or storage media containing the software and data used to implement the functionality circuits or modules used in accordance with embodiments of the present invention. The memory 136 can include, but is not limited to, the following types of devices: ROM, PROM, EPROM, EEPROM, flash memory, SRAM, DRAM and magnetic disk. In some embodiments of the present invention, the memory 136 may be a content addressable memory (CAM).

As further illustrated in FIG. 27, the memory (and/or storage media) 136 may include several categories of software and data used in the data processing system: an operating system 152; application programs 154; input/output device drivers 158; and data 156. As will be appreciated by those of skill in the art, the operating system 152 may be any operating system suitable for use with a data processing system, such as IBM®, OS/2®, AIX® or zOS® operating systems or Microsoft® Windows®95, Windows98, Windows2000 or WindowsXP operating systems, Unix or Linux™, IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 158 typically include software routines accessed through the operating system 152 by the application programs 154 to communicate with devices such as the input/output circuits 146 and certain memory 136 components. The application programs 154 are illustrative of the programs that implement the various features of the circuits and modules according to some embodiments of the present invention. Finally, the data 156 represents the static and dynamic data used by the application programs 154 the operating system 152 the input/output device drivers 158 and other software programs that may reside in the memory 136.

The data 156 may include (archived or stored) digital image data sets 122 with metadata correlated to respective patients. As further illustrated in FIG. 27, according to some embodiments of the present invention, the application programs 154 include a movement analysis module 124. The application programs can also include an implant blueprint module 126. The application program 154 may be located in a local server (or processor) and/or database or a remote server (or processor) and/or database, or combinations of local and remote databases and/or servers.

While the present invention is illustrated with reference to the application programs 154, and modules 124 and 126 in FIG. 27, as will be appreciated by those of skill in the art, other configurations fall within the scope of the present invention. For example, rather than being application programs 154 these circuits and modules may also be incorporated into the operating system 152 or other such logical division of the data processing system. Furthermore, while the application programs 124, 126 are illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 27 but may be provided by other arrangements and/or divisions of functions between data processing systems. For example, although FIG. 27 is illustrated as having various circuits and modules, one or more of these circuits or modules may be combined or separated without departing from the scope of the present invention.

Figure 28A:
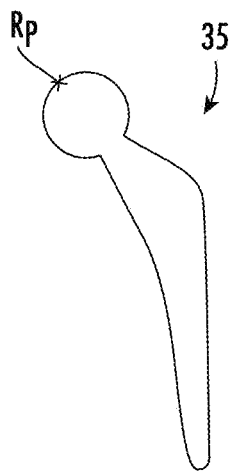
FIGS. 28A-28D are symbolic visualizations of an example reference point on an implant blueprint translated to a corresponding segmented object according to embodiments of the present invention.
Figure 28B:
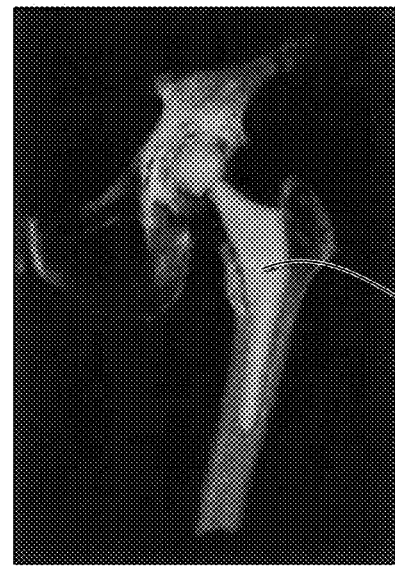
Figure 28C:
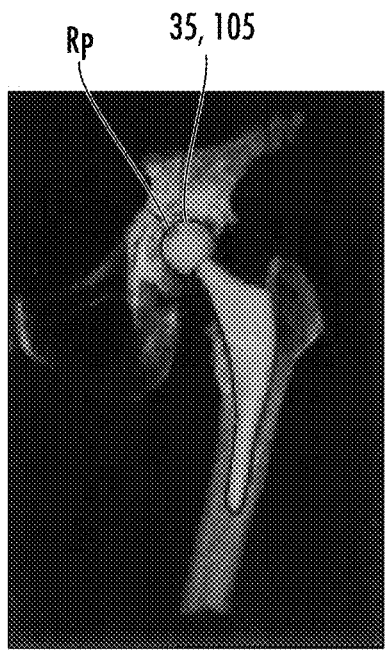
Figure 28D:

FIGS. 28A-28D symbolically illustrate translation of a defined reference point Rp on an implant blueprint 35 that can be translated to a corresponding segmentation object 105 in a medical image of a patient. It is noted that the translation process is typically automatic and not visualized as shown for explanatory purposes. FIG. 28A illustrates a reference point Rp added to an implant blueprint 35. FIG. 28B illustrates an implant object 105 of the same model as the implant blueprint segmented in a CT stack. FIG. 28C illustrates the implant blueprint 35 and segmentation object 105 are registered. FIG. 28D illustrates that due to the registration, the blueprint reference point Rp is connected to a specific point on the segmented implant 105.

FIGS. 29A-29C illustrate example point cloud generation. While shown with respect to an implant, the point cloud generation techniques can be used for other segmented objects such as bones or a combination of target bone and implant objects. FIG. 29A illustrates that a point cloud Pc can be generated to spatially represent an implant, with substantially uniform distribution Pu across the sure external surfaces. That is, the substantially uniform distribution can place points of the point clouds with similar distances between all neighboring points typically within 20% of the same distance between all each neighboring point. FIG. 29B illustrates that focus surface locations Fs can be defined on an implant blueprint 35 (left side) and a point cloud Pc can be placed only at those defined focus surface locations (right side). FIG. 29C illustrate that a point cloud can be generated to spatially represent an implant with higher point concentrations Ph where there is a high curvature of the implant shape relative to surfaces with lower curvatures.

FIGS. 30A-3C illustrate example templates T for measurement targets. The reference points Rp for measurement correspond to the objects used as registration targets. FIG. 30A illustrates a template T with a measurement target Rp for hip implant movement where the point to measure is the tip of the implant stem and movement is relative to reference of the adjacent femur bone $B_f$. FIG. 30B illustrates another template T with another measurement target for hip implant movement, where the point of measure Rp is the point at the top of the cup of the implant and movement is relative to the reference of the pelvic bone $B_p$. FIG. 30C illustrates another template T with a measurement target for spinal implant movement. The point of measure Rp is the tip of the lowest screw $S_1$ and the movement is relative to the reference of the second lowest (adjacent/neighboring) screw $S_2$.

FIGS. 31A-31E illustrate a target template collection Tc of defined (typically pre-defined or default) templates T for measurement and registration targets that can be used as inputs to automatically perform movement analysis. The measurement points P (red or solid dark circle for non-color versions), the measurement reference 900 is shown in green or in cross-hatch shading for non-color versions), and the registration-only targets 910 are shown in blue (slanted markings in non-color versions).

FIGS. 31A and 31B illustrate templates T with respective measurement targets 900. FIG. 31A illustrates the implant stem tip P versus the femur 900. FIG. 31B shows the top of the implant cup P and the pelvis 900. FIGS. 31C-31E illustrate example templates T for registration only (for qualitative analysis, no measurements). FIG. 31C shows the full implant as the registration target 910. FIG. 31D shows the cup of the implant as the registration target 910. FIG. 31E shows the stem of the implant as the registration target 910.

Figure 35A:
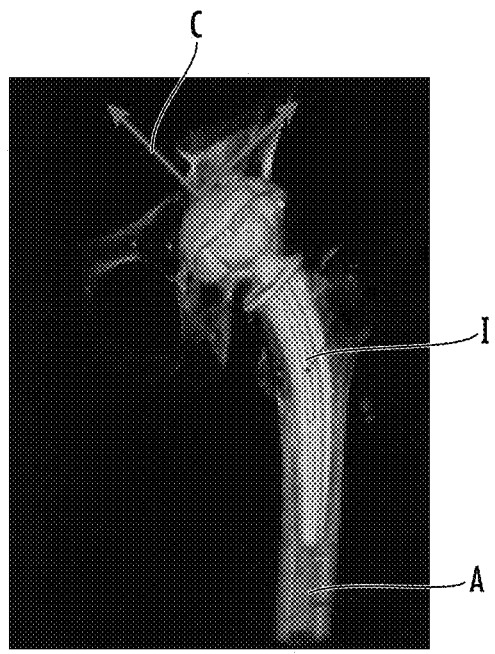
FIGS. 35A-35C are illustrations of example measurement references according to embodiments of the present invention.
Figure 35B:
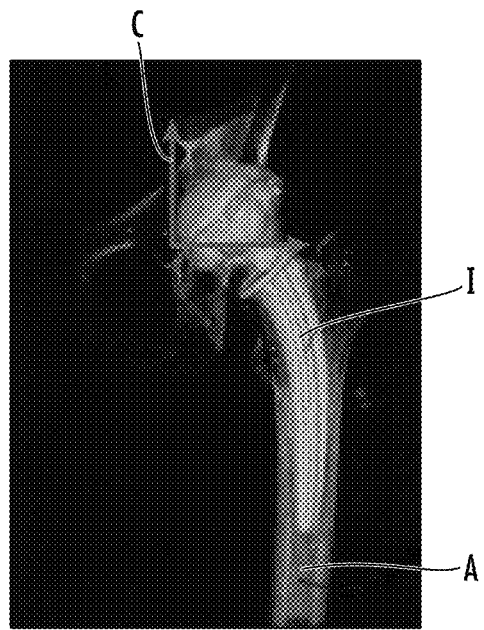
Figure 35C:
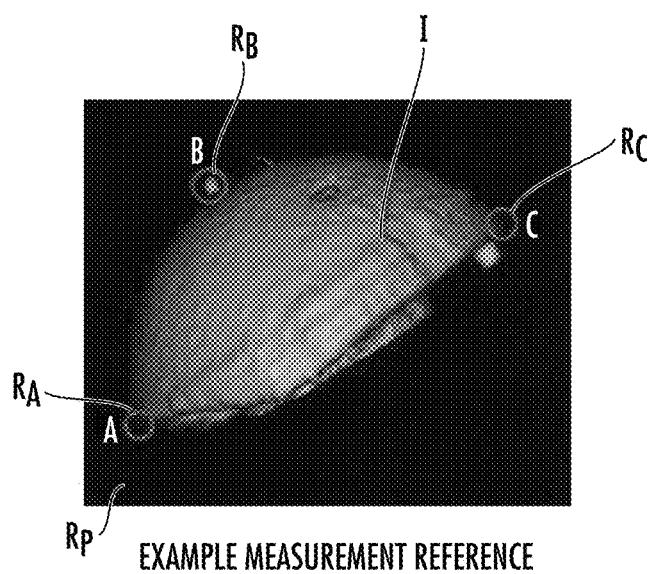

FIGS. 35A-35C illustrate examples of measurement references for analyzing movement. Movement measurements are reported in terms of translation and rotation in 3-dimensional space, in a coordinate system C, shown as a cartesian X, Y, Z coordinate system. This coordinate system C, and therefore all measurements reported therein, are usually defined either relative to the patient anatomy A (FIG. 35B), or relative to the implant I (FIG. 35A). For both, right side or left side variation exists. For measurements to be optimally useful, the coordinate system C is defined in an as repeatable and precise fashion as possible.

Any point of any implant or tissue with enough radiodensity can be used as reference points for measurements and/or coordinate systems. This is done by placing reference points Rp at points of particular interest. Reference points "Rp" can be selected such that the movement analysis is sensitive to specific implant failure modes or migration patterns of interest. Thus, different implants can have different defined reference points Rp. For example, a given implant type might be known to have its front moving whereas the part to the back usually has little migration so more reference points Rp may be provided on the front and less or none on the back. FIG. 35C illustrates three reference points defined on the implant, $R_A$, $R_B$, $R_C$ with $R_A$ at a front, $R_B$ at a top and $R_C$ at a back of the implant I.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. An automated implant analysis method comprising:
obtaining a batch of image data sets of a plurality of different patients having an implant coupled to bone;
providing a first data set of a first patient from the batch of image data sets, the first data set comprising a first image stack and a second image stack;
allowing a user to select parameter settings for implant movement analysis of the implant including selecting a first object of interest and a second reference object;
segmenting the first image stack and the second image stack to identify corresponding object pairs of the first object and the second object;
registering each of the identified object pairs;
automatically calculating measurements of movement of the implant and/or coupled bone after the registration;
automatically propagating the selected parameter settings to other image data sets of other patients of the batch of image data sets; and
electronically automatically repeating the segmentation, registration and calculated measurements for the batch of image data sets of others of the different patients.

2. The method of claim 1, wherein the first object is a target study object, wherein one of the first object and the second reference object is the implant, wherein the parameter settings include relating a coordinate system to the reference object, and identifying which measurements are to be calculated such as rotation and location of selected points of interest of the target study object.

3. The method of claim 1, wherein, after the first data set is analyzed, for identifying the first and second objects in the image data sets of the others of the different patients before a respective registration, the implant and associated position is first automatically electronically identified, then the second object is identified using the implant position as guidance.

4. The method of claim 1, further comprising automatically electronically defining a cohort analysis template based on the user selected parameter settings and the first object and the second reference object of the data set of the first patient, and wherein the cohort analysis template is used to automatically propagate the selected parameter settings to the other image data sets thereby using identical parameter settings across all comparisons provided by the calculated measurements.

5. The method of claim 1, further comprising providing a display of results of the calculated measurement of movement of the implant in the batch of image data sets.

6. The method of claim 1, further comprising providing a visualization of an aggregated view of overlying registered images of image data sets of the different patients with overlapping regions visually deemphasized relative to outliers.

7. The method of claim 6, wherein the overlapping regions have a reduced optical opacity relative to the outliers and/or are presented translucent or transparent.

8. The method of claim 6, wherein the visualization is presented with sub-regions shown with different opacities or contrast, and wherein different sub-regions are shown with an opacity and/or contrast that is inversely proportional to a number of objects overlapping in a respective sub-region.

9. The method of claim 1, further comprising displaying thumbnail images of registered objects of different patients.

10. The method of claim 9, further comprising:
electronically linking the thumbnail images to an aggregated view of all the registered objects of the different patients; and
allowing a user to navigate from a selected thumbnail image to the aggregated view.

11. The method of claim 1, wherein the segmenting step is carried out automatically, and wherein the method further comprises automatically repeating the segmenting step using different tuning parameters before the registering step to thereby provide more accurate segmentation of the first and second objects.

12. The method of claim 1, further comprising, before the segmenting step, automatically selecting relevant image stack pairs from the first and second patient image stacks, wherein the image stack pairs have the first and/or second object.

13. The method of claim 1, further comprising providing an electronic implant blueprint corresponding to the implant, wherein one or more of the segmenting, registering or calculating measurements is carried out using the electronic implant blueprint.

14. The method of claim 1, further comprising providing an electronic implant blueprint corresponding to the implant, wherein the segmenting is carried out a plurality of times for the first data set using a plurality of different threshold levels that varies noise levels to match the blueprint with the segmented first and/or second object.

15. The method of claim 1, further comprising providing an electronic implant blueprint corresponding to the implant, wherein the registration comprises matching point clouds of points generated on one or more surfaces of the first and/or second object.

16. The method of claim 1, further comprising:
providing an electronic implant blueprint corresponding to the implant;
defining points on the electronic implant blueprint where measurements are to be made; and
transferring the defined points to an image-domain implant, wherein the registration is carried out using the defined points.

17. The method of claim 1, further comprising:
providing an electronic implant blueprint corresponding to the implant;
electronically defining reference points on the electronic implant blueprint; then
electronically translating the blueprint reference points to the segmented implant object,
wherein the automatically calculating measurements of movement of the implant and/or coupled bone after the registration is carried out using the translated blueprint reference points.

18. The method of claim 1, further comprising:
providing an electronic implant blueprint corresponding to the implant; and
electronically defining focus surface locations on the electronic implant blueprint,
wherein, before the registration, automatically electronically translating the blueprint focus surface locations to corresponding locations on segmented first and/or second object, then generating an unevenly distributed point cloud with higher concentration at focus surface locations, then performing the registration using the generated point cloud.

19. The method of claim 1, wherein, before the registration, automatically electronically deriving shape characteristics across one or more surfaces of a segmented first and/or second object, then electronically defining high curvature locations as focus surface locations, then electronically generating an unevenly distributed point cloud with higher concentration at focus surface locations, then electronically performing the registration using the generated point cloud.

20. The method of claim 1, further comprising:
providing an electronic implant blueprint corresponding to the implant in the first patient;
electronically comparing a segmented first or second reference object to the implant blueprint; and
adjusting segmentation parameters and repeating the segmentation of the first data set.

21. A workstation comprising or in communication with an image processing circuit configured to carry out the method of claim 1.

22. The method of claim 9, wherein the thumbnail images of registered objects of different patients are sorted by an amount of calculated measurement of movement.

23. The method of claim 10, wherein the selected thumbnail image is visually emphasized in the aggregated view relative to other registered images of other thumbnail images.

* * * * *